United States Patent
Mehrling et al.

(10) Patent No.: US 11,266,631 B2
(45) Date of Patent: Mar. 8, 2022

(54) HODGKIN LYMPHOMA THERAPY

(71) Applicant: Purdue Pharmaceutical Products L.P., Stamford, CT (US)

(72) Inventors: Thomas Mehrling, Basel (CH); Rosaria De Filippi, Naples (IT); Antonio Pinto, Naples (IT)

(73) Assignee: PURDUE PHARMACEUTICAL PRODUCTS L.P., Stamford, CT (US)

( * ) Notice: Subject to any disclaimer, the term of this patent is extended or adjusted under 35 U.S.C. 154(b) by 0 days.

(21) Appl. No.: 16/341,089

(22) PCT Filed: Oct. 11, 2016

(86) PCT No.: PCT/EP2016/074331
§ 371 (c)(1),
(2) Date: Apr. 11, 2019

(87) PCT Pub. No.: WO2018/068832
PCT Pub. Date: Apr. 19, 2018

(65) Prior Publication Data
US 2020/0397759 A1 Dec. 24, 2020

(51) Int. Cl.
*A61K 31/4184* (2006.01)
*A61P 35/00* (2006.01)
*A61K 45/06* (2006.01)

(52) U.S. Cl.
CPC .......... *A61K 31/4184* (2013.01); *A61P 35/00* (2018.01); *A61K 45/06* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,134,127 A | 7/1992 | Stella et al. |
| 5,376,645 A | 12/1994 | Stella et al. |
| 5,571,534 A | 11/1996 | Jalonen et al. |
| 5,874,418 A | 2/1999 | Stella et al. |
| 6,046,177 A | 4/2000 | Stella et al. |
| 6,087,367 A | 7/2000 | Breslow et al. |
| 6,133,248 A | 10/2000 | Stella |
| 6,214,852 B1 | 4/2001 | Kim et al. |
| 6,407,079 B1 | 6/2002 | Muller et al. |
| 8,609,864 B2 | 12/2013 | Chen et al. |
| 8,962,855 B2 | 2/2015 | Chen et al. |
| 9,096,627 B2 | 8/2015 | Chen et al. |
| 9,376,395 B2 | 6/2016 | Chen et al. |
| RE46,144 E | 9/2016 | Chen et al. |
| 9,993,482 B2 | 6/2018 | Mehrling |
| 10,118,901 B2 | 11/2018 | Chen et al. |
| 10,744,120 B2 | 8/2020 | Mehrling et al. |
| 2002/0076409 A1 | 6/2002 | March et al. |
| 2006/0079528 A1 | 4/2006 | Finn et al. |
| 2006/0159713 A1 | 7/2006 | Brittain et al. |
| 2008/0146556 A1 | 6/2008 | Diebold et al. |
| 2010/0022512 A1 | 1/2010 | Wisdom et al. |
| 2010/0216858 A1 | 8/2010 | Popek et al. |
| 2011/0190363 A1 | 8/2011 | Drager et al. |
| 2011/0269706 A1 | 11/2011 | Chen et al. |
| 2011/0311624 A1 | 12/2011 | Loury et al. |
| 2013/0209558 A1 | 8/2013 | Patzak et al. |
| 2015/0086551 A1 | 3/2015 | Chen et al. |
| 2015/0231198 A1 | 8/2015 | Carniti et al. |
| 2017/0095482 A1 | 4/2017 | Mehrling |
| 2017/0151218 A1 | 6/2017 | Mehrling et al. |

(Continued)

FOREIGN PATENT DOCUMENTS

| | | |
|---|---|---|
| CL | 0501-2003 | 3/2003 |
| CL | 2272-2005 | 9/2005 |

(Continued)

OTHER PUBLICATIONS

Ciusani et al., Valproic acid increases the in vitro effects of nitrosureas on human glioma cell lines. Oncol Res. 2007;16(10):453-63.
Advanced Accelerator Applications, Ongoing Clinical Studies with Advanced Accelerator Applications Pipeline Candidates. Retrieved online at: http://www.adacap.com/research-development/clinical-trials/. 6 pages.

(Continued)

*Primary Examiner* — Samantha L Shterengarts
(74) *Attorney, Agent, or Firm* — McCarter & English, LLP

(57) ABSTRACT

There is provided a compound of formula I or a pharmacologically acceptable salt thereof for use in a method of treating Hodgkin lymphoma in a patient in need thereof comprising administering to said patient an effective amount of said compound of formula I or a pharmacologically acceptable salt thereof:

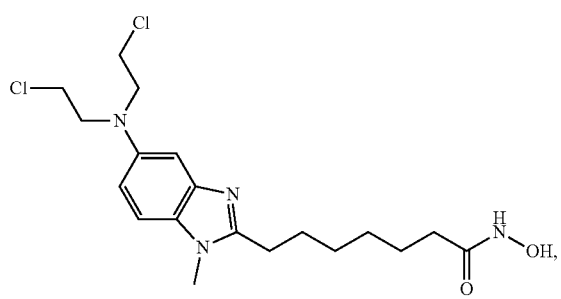

a combination of said compound of formula I or a pharmaceutically acceptable salt thereof with Brentuximab Vedotin and said combination for use in a method of treating Hodgkin lymphoma in a patient in need thereof comprising administering to said patient an effective amount of said combination.

18 Claims, 18 Drawing Sheets

(56) References Cited

U.S. PATENT DOCUMENTS

| | | | |
|---|---|---|---|
| 2017/0189382 | A1 | 7/2017 | Mehrling et al. |
| 2017/0296513 | A1 | 10/2017 | Mehrling et al. |
| 2018/0098969 | A1 | 4/2018 | Mehrling et al. |
| 2018/0369204 | A1 | 12/2018 | Mehrling et al. |
| 2019/0343807 | A1 | 11/2019 | Mehrling et al. |
| 2021/0059989 | A1 | 3/2021 | Mehrling et al. |

FOREIGN PATENT DOCUMENTS

| | | |
|---|---|---|
| CL | 3232-2006 | 11/2006 |
| CN | 1764648 A | 4/2006 |
| CN | 101084876 A | 12/2007 |
| CN | 101928234 A | 12/2010 |
| CN | 102993102 A | 3/2013 |
| DE | 34727 A1 | 12/1964 |
| EP | 0717638 B1 | 3/2002 |
| JP | 2007-531793 A | 11/2007 |
| WO | WO-1995/030442 A1 | 11/1995 |
| WO | WO-2002/010161 A1 | 2/2002 |
| WO | WO-2002/22577 A2 | 3/2002 |
| WO | WO-2002/026696 A1 | 4/2002 |
| WO | WO-2002/055017 A2 | 7/2002 |
| WO | WO-2004/076386 A2 | 9/2004 |
| WO | WO-2005/013958 A1 | 2/2005 |
| WO | WO-2005/097747 A1 | 10/2005 |
| WO | WO-2006/120456 A1 | 11/2006 |
| WO | WO-2007/134169 A2 | 11/2007 |
| WO | WO-2008/050125 A1 | 5/2008 |
| WO | WO-2008/067027 A2 | 6/2008 |
| WO | WO-2009/036016 A1 | 3/2009 |
| WO | WO-2009/067453 A1 | 5/2009 |
| WO | WO-2009/100045 A1 | 8/2009 |
| WO | WO-2010/042568 A1 | 4/2010 |
| WO | WO-2010/075542 A1 | 7/2010 |
| WO | WO-2010/085377 A2 | 7/2010 |
| WO | WO-2010/097700 A1 | 9/2010 |
| WO | WO-2011/017448 A1 | 2/2011 |
| WO | WO-2013/039488 A1 | 3/2013 |
| WO | WO-2013/040286 A2 | 3/2013 |
| WO | WO-2013/113838 A1 | 8/2013 |
| WO | WO-2015/085289 A1 | 6/2015 |
| WO | 2015/181156 A1 | 12/2015 |
| WO | WO-2015/181154 A1 | 12/2015 |
| WO | WO-2015/181157 A1 | 12/2015 |
| WO | WO-2016/087950 A1 | 6/2016 |

OTHER PUBLICATIONS

Aguado Bueno et al., Preliminary Experience of the Spanish Compassionate Use Registry of Bendamustine in Patients with Relapsed and/or Refractory Multiple Myeloma. Blood. 2012;120(21), Abstract 4035.

Al-Ani et al., Changes in urinary metabolomic profile during relapsing renal vasculitis. Sci Rep. Dec. 1, 2016;6:38074. 11 pages.

Alfarouk et al., Resistance to cancer chemotherapy: failure in drug response from ADME to P-gp. Cancer Cell Int. Jul. 15, 2015;15:71.

American Cancer Society, How does chemotherapy affect the risk of second cancers? Retrieved online at: https://www.cancer.org/treatment/treatments-and-side-effects/physical-side-effects/second-cancers-in-adults/chemotherapy.html. 5 pages (2017).

Anastasia et al., Bendamustine for Hodgkin lymphoma patients failing autologous or autologous and allogeneic stem cell transplantation: a retrospective study of the Fondazione Italiana Linfomi. Br J Haematol. Jul. 2014;166(1):140-2.

Andersson et al., Discovery of novel drug sensitivities in T-PLL by high-throughput ex vivo drug testing and mutation profiling. Leukemia. Aug. 14, 2017. pp. 1-14.

Andersson et al., Primary T-Prolymphocytic Leukemia (T-PLL) Cells Are Sensitive To BCL-2 and HDAC Inhibitors: Results From High-Throughput Ex Vivo Drug Testing. Blood. 2013;122:3828. 6 pages.

Angelucci et al., Suberoylanilide hydroxamic acid partly reverses resistance to paclitaxel in human ovarian cancer cell lines. Gynecol Oncol. Dec. 2010;119(3):557-63.

Arun et al., The PARP inhibitor AZD2281 (Olaparib) induces autophagy/mitophagy in BRCA1 and BRCA2 mutant breast cancer cells. Int J Oncol. Jul. 2015;47(1):262-8.

Attal et al., Lenalidomide, Bortezomib, and Dexamethasone with Transplantation for Myeloma. The New England Journal of Medicine. Apr. 6, 2017;376:1311-1320.

Audeh et al., Oral poly(ADP-ribose) polymerase inhibitor olaparib in patients with BRCA1 or BRCA2 mutations and recurrent ovarian cancer: a proof-of-concept trial. Lancet. Jul. 24, 2010;376(9737):245-51.

Bachmann et al., Epigenetic silencing of BIM in glucocorticoid poor-responsive pediatric acute lymphoblastic leukemia, and its reversal by histone deacetylase inhibition. Blood. Oct. 21, 2010;116(16):3013-22.

Bagchi, Bendamustine for advanced sarcoma. Lancet Oncol. Aug. 2007;8(8):674.

Balfour et al., Bendamustine. Drugs. 2001 ;61 (5):631-8.

Barendsen et al., Inhibition of TPA-induced monocytic differentiation in THP-1 human monocytic leukemic cells by staurosporine, a potent protein kinase C inhibitor. Leuk Res. 1990;14(5):467-74.

Berenson et al., Phase I/II trial assessing bendamustine plus bortezomib combination therapy for the treatment of patients with relapsed or refractory multiple myeloma. Br J Haematol. Feb. 2013;160(3):321-30.

Bernhard et al., Quality of life and quality-adjusted survival (Q-TWiST) in patients receiving dose-intensive or standard dose chemotherapy for high-risk primary breast cancer. Br J Cancer. Jan. 15, 2008;98(1):25-33.

Besse et al., The first in class, alkylator-histone-deacetylase-inhibitor fusion molecule EDO-S101 in combination with proteasome inhibitors induces highly synergistic pro-apoptotic signaling through UPR activation and suppression of c-Myc and BCL2 in multiple meyloma. ASH, 2016.

Besse et al., The first-in-class alkylating HDAC inhibitor EDO-S101 is highly synergistic with proteasome inhibition against multiple myeloma through activation of multiple pathways. Blood Cancer J. Jul. 2017;7(7):e589. 4 pages.

Besse et al., The First-in-Class, Alkylator-Histone-Deacetylase-Inhibitor Fusion Molecule EDO-S101 in Combination with Proteasome Inhibitors Induces Highly Synergistic Pro-Apoptotic Signaling through UPR Activation and Suppression of c-MYC and BCL2 in Multiple Myeloma. 58th ASH Annual Meeting, San Diego, Dec. 3-6, 2016, Publication No. 4466. 1 page.

Biete et al., Whole abdominal radiotherapy in ovarian cancer. Rep Pract Oncol Radiother. Mar. 23, 2010;15(2):27-30.

Blattmann et al., Enhancement of radiation response in osteosarcoma and rhabdomyosarcoma cell lines by histone deacetylase inhibition. Int J Radiat Oncol Biol Phys. Sep. 1, 2010;78(1):237-45.

Bose et al., Histone deacetylase inhibitor (HDACI) mechanisms of action: emerging insights. Pharmacol Ther. Sep. 2014;143(3):323-36.

Botrugno et al., Molecular pathways: old drugs define new pathways: non-histone acetylation at the crossroads of the DNA damage response and autophagy. Clin Cancer Res. May 1, 2012;18(9):2436-42.

Braga et al., Crystal Polymorphism and Multiple Crystal Forms. Struct Bond. 2009;132:25-50.

Brewster et al., Cyclodextrins as pharmaceutical solubilizers. Adv Drug Deliv Rev. Jul. 30, 2007;59(7):645-66.

Bruce et al., Glioblastoma Multiforme Treatment & Management. Medscape. Retrieved online at: https://emedicine.medscape.com/article/283252-treatment. 20 pages. Jun. 14, 2017.

Buglio et al., Histone deacetylase inhibitors in Hodgkin lymphoma. Invest New Drugs. Dec. 2010;28 Suppl 1:S21-7.

Buglio et al., Vorinostat inhibits STAT6-mediated TH2 cytokine and TARC production and induces cell death in Hodgkin lymphoma cell lines. Blood. Aug. 15, 2008;112(4):1424-33.

Cai et al., Combination of bendamustine and entinostat synergistically inhibits proliferation of multiple myeloma cells via induction of apoptosis and DNA damage response. Cancer Lett. Jul. 28, 2013;335(2):343-50.

Cai et al., Discovery of 7-(4-(3-ethynylphenylamino)-7-methoxyquinazolin-6-yloxy)-N-hydroxyheptanamide (CUDc-101) as

(56) References Cited

OTHER PUBLICATIONS a potent multi-acting HDAC, EGFR, and HER2 inhibitor for the treatment of cancer. J Med Chem. Mar. 11, 2010 ;53(5):2000-9.
Cai et al., Solubilization of vorinostat by cyclodextrins. J Clin Pharm Ther. Oct. 2010;35(5):521-6.
Campos et al., Expression of nuclear receptor corepressors and class I histone deacetylases in astrocytic gliomas. Cancer Sci. Feb. 2011;102(2):387-92.
Chamberlain et al., Salvage therapy with bendamustine for methotrexate refractory recurrent primary CNS lymphoma: a retrospective case series. J Neurooncol. May 2014;118(1):155-62.
Chen et al., A 71-gene signature of TRAIL sensitivity in cancer cells. Mol Cancer Ther. Jan. 2012;11(1):34-44.
Chen et al., Discovery of a Novel, Efficient, and Scalable Route to Bendamustine Hydrochloride: The API in Treanda. Org Process Res Dev. 2011;15(5):1063-1072.
Chesi et al., Drug response in a genetically engineered mouse model of multiple myeloma is predictive of clinical efficacy. Blood. Jul. 12, 2012;120(2):376-85.
Chesi et al., Identification of Novel Therapeutic Targets in the Clinically Predictive Vk*MYC Mouse Model of Multple Myeloma. ASH, 2 pages. 2014.
Chesi et al., Identification of Novel Therapeutic Targets in the Clinically Predictive Vk*MYC Mouse Model of Multple Myeloma. Blood. 2014;124:415.
Chisholm et al., Emergence of drug tolerance in cancer cell populations: an evolutionary outcome of selection, nongenetic instability, and stress-induced adaptation. Cancer Res. Mar. 15, 2015;75(6):930-9.
Chiu et al., Suberoylanilide hydroxamic acid, an inhibitor of histone deacetylase, enhances radiosensitivity and suppresses lung metastasis in breast cancer in vitro and in vivo. PLoS One. Oct. 10, 2013;8(10):e76340. 12 pages.
Choi et al., Enhanced cytotoxic effect of radiation and temozolomide in malignant glioma cells: targeting PI3K-AKT-mTOR signaling, HSP90 and histone deacetylases. BMC Cancer. Jan. 13, 2014;14:17. 12 pages.
Chow et al., In vitro induction of apoptosis of neoplastic cells in low-grade non-Hodgkin's lymphomas using combinations of established cytotoxic drugs with bendamustine. Haematologica. May 2001;86(5):485-93.
Ciavatta et al., Epigenetic basis for aberrant upregulation of autoantigen genes in humans with ANCA vasculitis. J Clin Invest. Sep. 2010;120(9):3209-19.
ClinicalTrials.gov, A Phase 1 Study to Investigate the Safety, Pharmacokinetic Profiles and the Efficacy of EDO-S101, a First-in-Class Alkylating Histone Deacetylase Inhibition (HDACi) Fusion Molecule, in Relapsed/Refractory Hematologic Malignancies. Clinical Trials Identifier: NCT02576496, Oct. 14, 2015. 5 pages.
ClinicalTrials.gov, Bendamustine, Lenalidomide (Revlimid®) and Dexamethasone (BRd) as 2nd-line Therapy for Patients With Relapsed or Refractory Multiple Myeloma (BRd). Clinical Trials Identifier: NCT01701076, Aug. 24, 2016.
ClinicalTrials.gov, Phase 1 Trial of Dasatinib and Bendamustine in Chronic Lymphocytic Leukemia. ClinicalTrials Identifier: NCT00872976, Apr. 22, 2009. 3 pages.
Connors, Hodgkin lymphoma: special challenges and solutions. Hematol Oncol. Jun. 2015;33 Suppl 1:21-4.
Cooke et al., Spontaneous onset and transplant models of the Vk*MYC mouse show immunological sequelae comparable to human multiple myeloma. J Transl Med. Sep. 6, 2016;14:259. 12 pages.
Corazzelli et al., Efficacy and safety of bendamustine for the treatment of patients with recurring Hodgkin lymphoma. Br J Haematol. Jan. 2013;160(2):207-15.
Curigliano et al., Cardiovascular toxicity induced by chemotherapy, targeted agents and radiotherapy: ESMO Clinical Practice Guidelines. Annals of Oncology. Oct. 2012;23(Suppl. 7):vii155-vii166.
De Filippi et al., "The First-in-Class Alkylating Histone-Deacetylase Inhibitor(HDACi) Fusion Molecule Edo-S101 Exerts Potent Preclinical Activity Against Tumor Cells of Hodgkin Lymphoma (HL) Including Bendamustine-Resistant Clones" ASH, 57th annual meeting and exposition, Dec. 2015, Abstract 2481.
De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Istituto Nazionale Tumor, IRCCS-Fondazione Pascale, Dec. 6, 2015. 1k page.
De Filippi et al., Edo-S101, a Bendamustine (BDM)/Histone-Deacetylase Inhibitor (HDACi) Fusion Molecule, Demonstrates Potent Preclinical Activity Against T-Cell Malignancies and Overcomes BDM-Resistance. ASH, 59th Annual Meeting & Exposition. Dec. 9-12, 2017. Poster 2547. 1 page.
De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. ASH 57th Annual Meeting & Exposition. Abstract No. 2481. Dec. 5-8, 2015 [Downloaded from: [https://ash.confex.com/ash/2015/webprogram/Paper84797.html]. 2 pages.
DeAngelo et al., Phase 1 clinical results with tandutinib (MLN518), a novel FLT3 antagonist, in patients with acute myelogenous leukemia or high-risk myelodysplastic syndrome: safety, pharmacokinetics, and pharmacodynamics. Blood. Dec. 1, 2006;108(12):3674-81.
DeSouza et al., Has the survival of patients with glioblastoma changed over the years? Br J Cancer. Jan. 19, 2016;114(2):146-50.
Diehl, The Evolution of Chemotherapy, Using the A-DAC Principle to Unlock New Treatment Options in Hodgkin Lymphoma. Mundipharma EDO Satellite Symposium, 10th International Symposium on Hodgkin Lymphoma, 6 pages, Oct. 23, 2016.
Dooley et al., Alkylating Histone Deacetylase Inhibitor Treatment in Animal Models of MPO-ANCA Vasculitis. Abstract TH-PO052. ASN, Kidney Week, Nov. 2, 2017, 2 pages.
Drogaris et al., Histone deacetylase inhibitors globally enhance h3/h4 tail acetylation without affecting h3 lysine 56 acetylation. Sci Rep. 2012;2:220. 12 pages.
Döhner et al., Diagnosis and management of acute myeloid leukemia in adults: recommendations from an international expert panel, on behalf of the European LeukemiaNet.Blood. Jan. 21, 2010 ;115(3):453-74.
edoncology.com, The A-DAC Principle: A New Concept in Oncology Treatment. 3 pages, Sep. 2016.
EU Clinical Trials Register, EudraCT No. 2005-002051-41. 13 pages. Dec. 7, 2016.
EU Clinical Trials Register, EudraCT No. 2005-006083-57. 28 pages. Jun. 1, 2016.
Eurordis, Rare Diseases Europe, Why Research on Rare Diseases? Position Paper. Retrieved online at: www.eurordis.org. 14 pages. Oct. 2010.
Fei et al., Development of clinically relevant orthotopic xenograft mouse model of metastatic lung cancer and glioblastoma through surgical tumor tissues injection with trocar. J Exp Clin Cancer Res. Jun. 29, 2010;29:84.
Festuccia et al., Enhancement of radiosensitivity by the novel anticancer quinolone derivative vosaroxin in preclinical glioblastoma models. EJC, European Journal of Cancer. Dec. 2016;69(Suppl 1):S62. Abstract 174, Poster P145.
Festuccia et al., Targeting glioblastoma with UniPR1331, a new and stable bioavailable small molecule inhibiting Ephephrin interaction: In vitro and in vivo evidence. EJC, European Journal of Cancer. Dec. 2016;69(Suppl 1), Abstract 71, Poster P042.
Festuccia et al., The first-in-class alkylating deacetylase inhibitor molecule tinostamustine shows antitumor effects and is synergistic with radiotherapy in preclinical models of glioblastoma. J Hematol Oncol. Feb. 27, 2018;11(1):32. 19 pages.
Frew et al., Enhancing the apoptotic and therapeutic effects of HDAC inhibitors. Cancer Lett. Aug. 8, 2009;280(2):125-33.
Furumai et al., Potent histone deacetylase inhibitors built from trichostatin A and cyclic tetrapeptide antibiotics including trapoxin. Proc Natl Acad Sci U S A. Jan. 2, 2001;98(1):87-92.
Geurink et al., Incorporation of non-natural amino acids improves cell permeability and potency of specific inhibitors of proteasome trypsin-like sites. J Med Chem. Feb. 14, 2013;56(3):1262-75.

(56) References Cited

OTHER PUBLICATIONS

Ghesquières et al., Clinical experience of bendamustine in relapsed or refractory Hodgkin lymphoma: a retrospective analysis of the French compassionate use program in 28 patients. Leuk Lymphoma. Nov. 2013;54(11):2399-404.
Gillis, HDAC Inhibition Appears to Sensitive Triple-Negative Breast Cancer Cells to Certain Treatments. Retrieved online at: https://www.onclive.com/conference-coverage/sabcs-2012/hdac-inhibition-appears-to-sensitize-triplenegative-breast-cancer-cells-to-certain-treatment, 2 pages, (2012).
Golub et al., Molecular classification of cancer: class discovery and class prediction by gene expression monitoring. Science. Oct. 15, 1999;286(5439):531-7.
Graham et al., T-cell prolymphocytic leukemia. Proc (Bayl Univ Med Cent). Jan. 2013;26(1):19-21.
Greaves et al., Clonal evolution in cancer. Nature. Jan. 18, 2012;481(7381):306-13.
Griffith et al., A novel anti-cancer bifunctional platinum drug candidate with dual DNA binding and histone deacetylase inhibitory activity. Chem Commu (Camb). Nov. 28, 2009;(44):6735-7.
Griffith et al., Novel Platinum Pyridinehydroxamic Acid Complexes: Synthesis, Characterisation, X-ray Crystallographic Study of Nitric Oxide Related Properties. Polyhedron. 2007;26:4697-4706.
Groselj et al., Histone deacetylase inhibitors as radiosensitisers: effects on DNA damage signalling and repair. Br J Cancer. Mar. 5, 2013;108(4):748-54.
Hancock et al., HDAC inhibitor therapy in autoimmunity and transplantation. Ann Rheum Dis. Apr. 2012;71 Suppl 2:i46-54.
Harrison et al., High Response Rates with the Combination of Bortezomib. Dexamethasone and the Pan-HistoneDeacetylase Inhibitor Romidepsin in Patients with Relapsed or Refractory Multiple Myeloma in a Phase 1/11 Clinical Trial. Blood. 2008;112, Abstract 3698. ASH Annual Meeting.
Hedgethorne et al., FORETINIB, c-Met and VEGFR-2 Inhibitor Oncolytic. Drugs of the Future. 2010;35(11):893-902.
Hegi et al., MGMT gene silencing and benefit from temozolomide in glioblastoma. N Engl J Med. Mar. 10, 2005;352(10):997-1003.
Her et al., Targeting DNA Double-strand Break Repair in Cancer Therapy. Journal of Molecular and Genetic Medicine. Dec. 31, 2015;9:e106, 1 page.
Herold et al., Bendamustine, vincristine and prednisone (BOP) versus cyclophosphamide, vincristine and prednisone (COP) in advanced indolent non-Hodgkin's lymphoma and mantle cell lymphoma: results of a randomised phase III trial (OSHO# 19). J Cancer Res Clin Oncol. Feb. 2006;132(2):105-12.
Herold et al., BOP versus COP in Advanced Low Grade Non-Hodgkin's Lymphomas—Results of a Randomized Multicenter Study. Blood. 1999;94:262b. Abstract 4382.
Hoffman, Brentuximab Vedotin Plus Bendamustine Active In Heavily Pretreated Hodgkin Lymphoma, ALCL. Cancer Therapy Advisor, Dec. 7, 2015. 2 pages. retreived online at: http://www.cancertherapyadvisor.com/ash-2015/hodgkin-lymphoma-alcl-brentuximab-vedotin-better-treatment-risk/article/458249/.
Hong et al., Complete Durable Response From Carboplatin and Olaparib in a Heavily Pretreated Triple-Negative Metastatic Breast Cancer With Germline BRCA2 and "BRCAness" Mutations. J Oncol Pract. Mar. 2016;12(3):270-2.
Howlader et al., Contributions of Subtypes of Non-Hodgkin Lymphoma to Mortality Trends. Cancer Epidemiol Biomarkers Prev. Jan. 2016;25(1):174-9.
Ihle et al., HR23b expression is a potential predictive biomarker for HDAC inhibitor treatment in mesenchymal tumours and is associated with response to vorinostat. The Journal of Pathology: Clinical Research. 2016;2:59-71.
Jagannath et al., Bortezomib in combination with dexamethasone for the treatment of patients with relapsed and/or refractory multiple myeloma with less than optimal response to bortezomib alone. Haematologica. Jul. 2006;91(7):929-34.
Jawhari et al., In Vitro and In Vivo Preclinical Activity of EDO-S101 in Hodgkin Lymphoma. Haematologica. 2016;101(s5):6-7, Abstract P037.
Jennette et al., Pathogenesis of antineutrophil cytoplasmic autoantibody-mediated disease. Nat Rev Rheumatol. Aug. 2014;10(8):463-73.
Jiang et al., A mammalian functional-genetic approach to characterizing cancer therapeutics. Nature Chemical Biology. Feb. 2011;7:92-100.
Kaddour et al., Transmission of Induced Chromosomal Aberrations through Successive Mitotic Divisions in Human Lymphocytes after In Vitro and ?In? Vivo Radiation. Scientific Reports. Jun. 12, 2017;7:3291, 11 pages.
Kalin et al., Creating zinc monkey wrenches in the treatment of epigenetic disorders. Curr Opin Chem Biol. Jun. 2009;13(3):263-71.
Kallenberg, Pathogenesis and treatment of ANCA-associated vasculitides. Clin Exp Rheumatol. Jul.-Aug. 2015;33(4 Suppl 92):S11-4.
Kallenberg, Pathogenesis of ANCA-associated vasculitides. Ann Rheum Dis. Mar. 2011;70 Suppl 1 :i59-63.
Kalsi et al., The impact of low-grade toxicity in older people with cancer undergoing chemotherapy. Br J Cancer. Dec. 9, 2014;111(12):2224-8.
Kampa-Schittenhelm et al., Quizartinib (AC220) is a potent second generation class III tyrosine kinase inhibitor that displays a distinct inhibition profile against mutant-FLT3, -PDGFRA and -KIT isoforms. Molecular Cancer. 2013; 12:19, 15 pages.
Kaufman et al., Lenalidomide. Bortezomib. and Dexamethasone (RVD) in Combination with Vorinostat As Front-Line Therapy for Patients with Multiple Myeloma (MM): Results of a Phase 1 Study. Blood. 2012;120, Abstract No. 336. 2 pages. ASH Annual Meeting.
Keating et al., Bendamustine. Nat Rev Drug Discov. Jun. 2008;7(6):473-4.
Khot et al., Panobinostat in lymphoid and myeloid malignancies. Expert Opin Investig Drugs. Sep. 2013;22(9):1211-23.
Kigawa, New strategy for overcoming resistance to chemotherapy of ovarian cancer. Yonago Acta Med. Jun. 2013;56(2):43-50.
Kim et al., Histone deacetylase inhibitors: molecular mechanisms of action and clinical trials as anti-cancer drugs. Am J Transl Res. Feb. 2011;3(2):166-79.
Knauf, Bendamustine in the treatment of chronic lymphocytic leukemia. Expert Rev Anticancer Ther. Feb. 2009;9(2):165-74.
Knittel et al., Two mouse models reveal an actionable PARP1 dependence in aggressive chronic lymphocytic leukemia. Nat Commun. Jul. 28, 2017;8(1):153. 13 pages.
Kollmannsberger et al., Phase II study of bendamustine in patients with relapsed or cisplatin-refractory germ cell cancer. Anticancer Drugs. Aug. 2000;11(7):535-9.
Kotzin et al., Reversal of nzb/nzw disease with total lymphoid irradiation. J Exp Med. Aug. 1, 1979;150(2):371-8.
Kraus et al., EDO-S101, A New Alkylating Histone-Deacetylase Inhibitor (HDAC) Fusion Molecule has Superior Activity Against Myeloma and B Cell Lympoma and Strong Synergy, With Proteasome Inhibitors in vitro. ASH, 2014.
Kraus et al., EDO-S101, A New Alkylating Histone-Deacetylase Inhibitor (HDACi) Fusion Molecule, has Superior Activity Against Myeloma and B Cell Lympoma and Strong Synergy With Proteasome Inhibitors in vitro. ASH, 2014. Publication No. 2249.
Kraus et al., EDO-S101, A New Alkylating Histone-Deacetylase Inhibitor (HDACi) Fusion Molecule, Has Superior Activity Against Myeloma and B Cell Lympoma and Strong Synergy with Proteasome Inhibitors in vitro. Blood. 2014;124;2249.
Krause et al., Tyrosine kinases as targets for cancer therapy. N Engl J Med. Jul. 14, 2005;353(2): 172-87.
Kumar et al., Histone deacetylase inhibitors induce cell death in supratentorial primitive neuroectodermal tumor cells. Oncol Rep. Nov. 2006;16(5):1047-52.
Lala et al., Role of nitric oxide in tumor progression: lessons from experimental tumors. Cancer Metastasis Rev. Mar. 1998;17(1):91-106.

(56) References Cited

OTHER PUBLICATIONS

Layman et al., Severe and prolonged lymphopenia observed in patients treated with bendamustine and erlotinib for metastatic triple negative breast cancer. Cancer Chemother Pharmacol. May 2013;71(5):1183-90.

Le Moigne et al., The p97 Inhibitor CB-5083 Is a Unique Disrupter of Protein Homeostasis in Models of Multiple Myeloma. Molecular Cancer Therapeutics. Nov. 2017;16(11):2375-2386.

Lee et al., Phase I/Ib study of olaparib and carboplatin in BRCA1 or BRCA2 mutation-associated breast or ovarian cancer with biomarker analyses. J Natl Cancer Inst. May 19, 2014;106(6):dju089. 11 pages.

Lehmann et al., Refinement of Triple-Negative Breast Cancer Molecular Subtypes: Implications for Neoadjuvant Chemotherapy Selection. PLoS One. Jun. 16, 2016;11(6):e0157368, 22 pages.

Lentzsch et al., Combination of bendamustine, lenalidomide, and dexamethasone (BLD) in patients with relapsed or refractory multiple myeloma is feasible and highly effective: results of phase 1/2 open-label, dose escalation study. Blood. May 17, 2012;119(20):4608-13.

Leoni et al., Bendamustine (Treanda) displays a distinct pattern of cytotoxicity and unique mechanistic features compared with other alkylating agents. Clin Cancer Res. Jan. 1, 2008;14(1):309-17.

Leoni, Bendamustine: rescue of an effective antineoplastic agent from the mid-twentieth century. Semin Hematol. Apr. 2011;48 Suppl 1 :S4-11.

Leung-Hagesteijn et al., Xbp1s-negative tumor B cells and pre-plasmablasts mediate therapeutic proteasome inhibitor resistance in multiple myeloma. Cancer Cell. Sep. 9, 2013;24(3):289-304.

Liby et al., Elevated and Deregulated Expression of HDAC3 in Human Astrocytic Glial Tumours. Folia Biologica (Praha). 2006;52:21-33.

Lin et al., Anti-rheumatic activities of histone deacetylase (HDAC) inhibitors in vivo in collagen-induced arthritis in rodents. Br J Pharmacol. Apr. 2007;150(7):862-72.

Lin et al., Treatment of Brain Metastases. J Clin Oncol. Oct. 20, 2015;33(30):3475-84.

Little et al., Experimental autoimmune vasculitis: an animal model of anti-neutrophil cytoplasmic autoantibody-associated systemic vasculitis. Am J Pathol. Apr. 2009;174(4):1212-20.

Little et al., Therapeutic effect of anti-TNF-alpha antibodies in an experimental model of anti-neutrophil cytoplasm antibody-associated systemic vasculitis. J Am Soc Nephrol. Jan. 2006;17(1):160-9.

Liu et al., A DNA/HDAC dual-targeting drug CY190602 with significantly enhanced anticancer potency. EMBO Mol Med. 12 pages, Published online: Mar. 9, 2015.

Liu, Characterization of TCL1-Tg:P53- / -Mice that Resemble Human Chronic Lymphocytic Leukemia with 17P-Deletion. UT GSBS Thesis, Graduate School of Biomedical Sciences, Digital Commons@The Texas Medical Center, May 2013. 142 pages.

Loftsson et al., Historical Perspectives: Cyclodextrins and their pharmaceutical applications. International Journal of Pharmaceutics. 2007;329:1-11.

Lombardi et al., Predictors of survival and effect of short (40 Gy) or standard-course (60 Gy) irradiation plus concomitant temozolomide in elderly patients with glioblastoma: a multicenter retrospective study of AINO (Italian Association of Neuro-Oncology). J Neurooncol. Nov. 2015;125(2):359-67.

Lopez-Iglesias et al., Preclinical anti-myeloma activity of EDO-S101, a new bendamustine-derived molecule with added HDACi activity, through potent DNA damage induction and impairment of DNA repair. J Hematol Oncol. Jun. 20, 2017;10(1):127. 14 pages.

Lopez-Iglesias et al., Preclinical anti-myeloma activity of the alkylating-HDACi molecule EDO-S101 through DNA-damaging and HDACi effects. EDO, http://mundipharma-edo.com. Poster Jun. 1, 2014.

Lopez-Iglesias et al., Preclinical Anti-Myeloma Activity of the Alkylating-HDACi Molecule EDO-S101 Through DNA-Damaging and HDACi Effects. EHA 2014 Poster, Jun. 12, 2014.

Lopez-Iglesias et al., Preclinical antimyeloma activity of EDO-S101 (bendamustine-vorinostat fusion molecule) through DNA-damaging and HDACi effects. 15th International Myeloma Workshop. Sep. 23-26, 2015. Rome, Italy. Clinical Lymphoma, Myeloma & Leukemia. Sep. 2015;15(3 Suppl. 3):e218, Abstract P0-238.

Lopez-Iglesias et al., The Alkylating Histone Deacetylase Inhibitor Fusion Molecule Edo-S101 Displays Full Bi-Functional Properties in Preclinical Models of Hematological Malignancies. Blood. 2014;124:2100.

Lopez-Iglesias et al., The Hybrid Molecule, Edo-S101, Impairs Double Strand Breaks Repair in Multiple Myeloma and Synergizes with Bortezomib and Dexamethasone. Blood. 2015;126(23):5354-5354.

Lucio-Eterovic et al., Differential expression of 12 histone deacetylase (HDAC) genes in astrocytomas and normal brain tissue: class II and IV are hypoexpressed in glioblastomas. BMC Cancer. Aug. 19, 2008;8:243.

Ludwig et al., Bendamustine-bortezomib-dexamethasone is an active and well-tolerated regimen in patients with relapsed or refractory multiple myeloma. Blood. Feb. 13, 2014;123(7):985-91.

Marchion et al., Development of histone deacetylase inhibitors for cancer treatment. Expert Rev Anticancer Ther. Apr. 2007;7(4):583-98.

Marks, Discovery and development of SAHA as an anticancer agent. Oncogene. Feb. 26, 2007;26(9):1351-6.

Marmion et al., Hydroxamic Acids—An Intriguing Family of Enzyme Inhibitors and Biomedical Ligands. Eur J Inorg Chem. 2004(15):3003-3016.

McInnis et al., Dysregulation of autoantigen genes in ANCA-associated vasculitis involves alternative transcripts and new protein synthesis. J Am Soc Nephrol. Feb. 2015;26(2):390-9.

Meanwell, Synopsis of some recent tactical application of bioisosteres in drug design. J Med Chem. Apr. 28, 2011;54(8):2529-91.

Medline AN-NLM24103869, Chen et al., Dexamethasone and Vorinostat Cooperatively Promote Differentiation and Apoptosis in Kasumi-1 Leukemia Cells Through Ubiquitination and Degradation of AML1-ETO. 2 pages.

Medline/NLM AN: NLM24998648, 1 page.

Mehrling et al., Activity of the alkylating histone-deacetylase inhibition fusion molecule EDO-S-101 in preclinical models of human glioblastoma independent from MGMT expression. Journal of Clinical Oncology. May 29, 2017;33(Suppl. 15), Abstract e13031.

Mehrling et al., Is there hope to treat glioblastoma effectively? CNS Oncol. 2015;4(6):377-9.

Mehrling et al., The Alkylating-HDAC Inhibition Fusion Principle: Taking Chemotherapy to the Next Level with the First in Class Molecule EDO-S101. Anticancer Agents Med Chem. 2016;16(1):20-8.

Mehrling, Chemotherapy is getting 'smarter'. Future Oncol. 2015;11 (4):549-52.

Mehrling, First in human clinical trails to commence Q3 2015. Mundipharma EDO GmbH. Retrieved online at: http://mundipharma-edo.com. Jul. 31, 2015. 2 pages.

Mehrling, First-in-human clinical trial of its lead compound, EDO-S101. Mundipharma EDO GmbH. Retrieved online at: http://mundipharma-edo.com. May 31, 2016. 2 pages.

Mehrling, Fusion Therapy, a New Approach to Combining Treatments. Drug Discovery World. 2016;71-76.

Mey et al., Bendamustine, lenalidomide and dexamethasone (BRd) has high activity as 2(nd)-line therapy for relapsed and refractory multiple myeloma—a phase II trial. Br J Haematol. Mar. 2017;176(5):770-782.

Miller et al., Histone deacetylase inhibitors. J Med Chem. Nov. 20, 2003;46(24):5097-116.

Minucci et al., Histone deacetylase inhibitors and the promise of epigenetic (and more) treatments for cancer. Nat Rev Cancer. Jan. 2006;6(1):38-51.

Mishra et al., Histone deacetylase inhibitors modulate renal disease in the MRL-Ipr/Ipr mouse. J Clin Invest. Feb. 2003;111 (4):539-52.

Moosman et al., Weekly treatment with a combination of bortezomib and bendamustine in relapsed or refractory indolent non-Hodgkin lymphoma. Leuk Lymphoma. Jan. 2010;51 (1):149-52.

Moradei et al., Histone deacetylase inhibitors: latest developments, trends and prospects. Curr Med Chem Anticancer Agents. Sep. 2005;5(5):529-60.

(56) References Cited

OTHER PUBLICATIONS

Moreau et al., Phase 1b Dose Escalation Study Of Oral Quisinostat, a Histone Deacetylase Inhibitor (HDACi), In Combination With Velcade (Bortezomib) and Dexamethasone For Patients With Relapsed Multiple Myeloma (MM). Blood. Nov. 15, 2013;122(21):1932.
Moreau et al., Proteasome inhibitors in multiple myeloma: 10 years later. Blood. Aug. 2, 2012;120(5):947-59.
Moscovitch et al., Successful treatment of autoimmune manifestations in MRL/I and MRL/n mice using total lymphoid irradiation (TLI). Exp Mol Pathol. Feb. 1983;38(1):33-47.
Moskowitz et al., Phase II study of bendamustine in relapsed and refractory Hodgkin lymphoma. J Clin Oncol. Feb. 1, 2013;31(4):456-60.
Moskowitz, Bendamustine: a bridge to longer term solutions in heavily treated Hodgkin lymphoma. Leuk Lymphoma. Nov. 2013;54(11):2339-40.
MRF, Melanoma Research Foundation, Melanoma Central Nervous System Metastases, Current Approaches, Challenges and Opportunities. 5 pages (2015).
Munker et al., Activity of Tyrosine Kinase Inhibitors in Multiple Myeloma. Blood. 2007; 110(11):274B, Abstract 4804.
National Institute of Health, Cancer. MedlinePlus. Retrieved online at: http://www.nlm.nih.gov/medlineplus/cancer.html. 10 pages. Apr. 16, 2007.
O'Donnell et al., Cancer pharmacoethnicity: ethnic differences in susceptibility to the effects of chemotherapy. Clin Cancer Res. Aug. 1, 2009;15(15):4806-14.
O'Reilly et al., Urinary Soluble CD163 in Active Renal Vasculitis. J Am Soc Nephrol. Sep. 2016;27(9):2906-16.
Ocio et al., Deacetylase Inhibition in Haematological Malignancies—Advanced T-cell Lymphoma, Hodgkin's Lymphoma, Multiple Myeloma, Acute Myelogenous Leukaemia and Myelodysplastic Syndrome. European Haematology. 2010;4:47-50.
Ocio et al., In vitro and in vivo rationale for the triple combination of panobinostat (LBH589) and dexamethasone with either bortezomib or lenalidomide in multiple myeloma. Haematologica. May 2010;95(5):794-803.
Ocio et al., Phase I study of plitidepsin in combination with bortezomib and dexamethasone in patients with relapsed and/or refractory multiple myeloma. Journal of Clinical Oncology. 2016;34:Abstract 8006, 1 page.
Ocio et al., Triple Combinations of the HDAC Inhibitor Panobinostat (LBH589) Plus Dexamethasone with Either Lenalidomide or Bortezomib are Highly Effective in a Multiple Myeloma Mouse Model. Blood. 2007;110:Abstract 1514. ASH Annual Meeting.
Ocio, Epigenetic regulation and HAC inhibitors, Still a role for these agents in MM? Institute of Biomedical Research of Salamanca, University of Salamanca, Cancer Research Center, Slideshow. 32 pages, (2016).
Offidani et al., Efficacy and tolerability of bendamustine, bortezomib and dexamethasone in patients with relapsed-refractory multiple myeloma: a phase II study. Blood Cancer J. Nov. 22, 2013;3:e162.
Oken et al., Toxicity and response criteria of the Eastern Cooperative Oncology Group. Am J Clin Oncol. Dec. 1982;5(6):649-55.
Oriol et al., Outcome after relapse of acute lymphoblastic leukemia in adult patients included in four consecutive risk-adapted trials by the PETHEMA Study Group. Haematologica. Apr. 2010;95(4):589-596.
Paris et al., Histone deacetylase inhibitors: from bench to clinic. J Med Chem. Mar. 27, 2008;51(6):1505-29.
Phan et al., An update on ethnic differences in drug metabolism and toxicity from anti-cancer drugs. Expert Opin Drug Metab Toxicol. Nov. 2011;7(11):1395-410.
Phiel et al., Histone deacetylase is a direct target of valproic acid, a potent anticonvulsant, mood stabilizer, and teratogen. J Biol Chem. Sep. 28, 2001;276(39):36734-41.
Pitha et al., Parenteral hydroxypropyl cyclodextrins: intravenous and intracerebral administration of lipophiles. J Pharm Sci. Jun. 1994;83(6):833-7.
Poenisch et al., Bendamustine/Prednisone Versus Melphalane/Prednisone in the Primary Treatment of Multiple Myeloma: an Updated Analysis of the 94BP01 Protocol. Blood. 2000;96(Suppl 1:759a), Abstract 3284, Poster Board Session 748-111.
Puetzer et al., Towards novel strategies of targeting specific vulnerabilities of T-PLL cells. AACR Annual Meeting. Jul. 2017;77(Suppl 13), Abstract 1372.
Pönisch et al., Combined bendamustine, prednisone and bortezomib (BPV) in patients with relapsed or refractory multiple myeloma. J Cancer Res Clin Oncol. Mar. 2013;139(3):499-508.
Pönisch et al., Treatment of bendamustine and prednisone in patients with newly diagnosed multiple myeloma results in superior complete response rate, prolonged time to treatment failure and improved quality of life compared to treatment with melphalan and prednisone—a randomized phase III study of the East German Study Group of Hematology and Oncology (OSHO). J Cancer Res Clin Oncol. Apr. 2006;132(4):205-12.
Qian et al., Activity of PXD101, a histone deacetylase inhibitor, in preclinical ovarian cancer studies. Mol Cancer Ther. Aug. 2006;5(8):2086-95.
Rajewski et al., Preliminary safety evaluation of parenterally administered sulfoalkyl ether beta-cyclodextrin derivatives. J Pharm Sci. Aug. 1995;84(8):927-32.
Rang et al., Glucocorticoids. Rang and Dale's Pharmacology, Sixth Edition. Elsevier, Limited, 3 pages, (2007).
Rasheed et al., Histone deacetylase inhibitors in cancer therapy. Expert Opin Investig Drugs. May 2007;16(5):659-78.
Rasschaert et al., A phase I study of bendamustine hydrochloride administered day 1+2 every 3 weeks in patients with solid tumours. Br J Cancer. Jun. 4, 2007;96(11):1692-8.
Rasschaert et al., A phase I study of bendamustine hydrochloride administered once every 3 weeks in patients with solid tumors. Anticancer Drugs. Jun. 2007;18(5):587-95.
Regna et al., HDAC expression and activity is upregulated in diseased lupus-prone mice. Int Immunopharmacol. Dec. 2015;29(2):494-503.
Reilly et al., Modulation of renal disease in MRL/Ipr mice by suberoylanilide hydroxamic acid. J Immunol. Sep. 15, 2004;173(6):4171-8.
Rengstl et al., Small and big Hodgkin-Reed-Sternberg cells of Hodgkin lymphoma cell lines L-428 and L-1236 lack consistent differences in gene expression profiles and are capable to reconstitute each other. PLoS One. May 15, 2017;12(5):e0177378.
Rodriguez-Tenreiro Y Sanchez, Hydrogels of Cyclodextrin Co-crosslinked and Interpenetrated for Controlled Drug Release. University of Santiago de Compostela, School of Pharmacy. pp. 29-32, (2006).
Ryu et al., Valproic acid downregulates the expression of MGMT and sensitizes temozolomide-resistant glioma cells. J Biomed Biotechnol. 2012;2012:987495. 9 pages.
Sampson et al., Vorinostat Enhances Cytotoxicity of SN-38 and Temozolomide in Ewing Sarcoma Cells and Activates STAT3/AKT/MAPK Pathways. PLoS One. Nov. 16, 2015;10(11):e0142704, 19 pages.
Sanchez et al., Anti-Myeloma Effects of Carfilzomib with Cyclophosphamide (CY) or Bendamustine (Ben). Blood. 2012;120(21), Abstract 2952. 54th ASH Annual Meeting adn Exposition.
Santacruz et al., The prognostic impact of minimal residual disease in patients with chronic lymphocytic leukemia requiring first-line therapy. Haematologica. May 2014;99(5):873-80.
Sarkaria et al., Mechanisms of chemoresistance to alkylating agents in malignant glioma. Clin Cancer Res. May 15, 2008;14(10):2900-8.
Saulnier et al., An Efficient Method for the Synthesis of Guanidino Prodrugs. Bioorganic & Medicinal Chemistry Letters. 1994;4(16):1985-1990.
Sawas et al., The Combination of Brentuximab Vedotin (Bv) and Bendamustine (B) Demonstrates Marked Activity in Heavily Treated Patients with Relapsed or Refractory Hodgkin Lymphoma (HL) and Anaplastic Large T-Cell Lymphoma (ALCL): Results of an International Multi Center Phase I/II Experience. Blood. 2015;126:586.

(56) References Cited

OTHER PUBLICATIONS

Schöffski et al., Repeated administration of short infusions of bendamustine: a phase I study in patients with advanced progressive solid tumours. J Cancer Res Clin Oncol. Jan. 2000;126(1):41-7.
Schöffski et al., Weekly administration of bendamustine: a phase I study in patients with advanced progressive solid tumours. Ann Oncol. Jun. 2000;11(6):729-34.
Shah et al., Comprehensive analysis of MGMT promoter methylation: correlation with MGMT expression and clinical response in GBM. PLoS One. Jan. 7, 2011;6(1):e16146.
Shipley et al., Acute myelogenous leukemia. Exp Hematol. Jun. 2009;37(6):649-58.
Simon, Optimal two-stage designs for phase II clinical trials. Control Clin Trials. Mar. 1989;10(1):1-10.
Song et al., Increased expression of histone deacetylase 2 is found in human gastric cancer. APMIS. 2005;113:264-8.
Stiborová et al., The synergistic effects of DNA-targeted chemotherapeutics and histone deacetylase inhibitors as therapeutic strategies for cancer treatment. Curr Med Chem. 2012;19(25):4218-38.
Storer, Design and analysis of phase I clinical trials. Biometrics. Sep. 1989;45(3):925-37.
Sturn et al., Genesis: cluster analysis of microarray data. Bioinformatics. Jan. 2002;18(1):207-8.
Tago et al., Repeated 0.5-Gy gamma irradiation attenuates autoimmune disease in MRL-Ipr/Ipr mice with suppression of CD3+CD4-CD8-B220+ T-cell proliferation and with up-regulation of CD4+CD25+Foxp3+ regulatory T cells. Radiat Res. Jan. 2008;169(1):59-66.
Takai et al., Human ovarian carcinoma cells: histone deacetylase inhibitors exhibit antiproliferative activity and potently induce apoptosis. Cancer. Dec. 15, 2004;101(12):2760-70.
Tesar et al., Limitations of standard immunosuppressive treatment in ANCA-associated vasculitis and lupus nephritis. Nephron Clin Pract. 2014;128(3-4):205-15.
Thurn et al., Rational therapeutic combinations with histone deacetylase inhibitors for the treatment of cancer. Future Oncol. Feb. 2011;7(2):263-83.
Topalian et al., Immune checkpoint blockade: a common denominator approach to cancer therapy. Cancer Cell. Apr. 13, 2015;27(4):450-61.
Trivedi et al., Management of Chemotherapy-Induced Peripheral Neuropathy. American Journal of Hematology / Oncology. Jan. 2015;11(1):4-10.
Tutt et al., Oral poly(ADP-ribose) polymerase inhibitor olaparib in patients with BRCA1 or BRCA2 mutations and advanced breast cancer: a proof-of-concept trial. Lancet. Jul. 24, 2010;376(9737):235-44.
Valdez et al., Synergistic cytotoxicity of the DNA alkylating agent busulfan, nucleoside analogs and suberoylanilide hydroxamic acid in lymphoma cell lines. Leuk Lymphoma. May 2012;53(5):973-81.
Van Krieken, New developments in the pathology of malignant lymphoma. A review of the literature published from Jan.-Apr. 2016. J Hematop. Jun. 13, 2016;9(2):73-83.
Viel et al., Optimizing glioblastoma temozolomide chemotherapy employing lentiviral-based anti-MGMT shRNA technology. Mol Ther. Mar. 2013;21(3):570-9.
Vippagunta et al., Crystalline Solids. Advanced Drug Delivery Reviews. 2001;48:3-26.
Vlachostergios et al., Bortezomib overcomes MGMT-related resistance of glioblastoma cell lines to temozolomide in a schedule-dependent manner. Invest New Drugs. Oct. 2013;31(5):1169-81.
Von Tresckow et al., An update on emerging drugs for Hodgkin lymphoma. Expert Opin Emerg Drugs. Jun. 2014;19(2):215-24.
Vyas et al., Cyclodextrin based novel drug delivery systems. J Incl Phenom Macrocycl Chem. 2008;62:23-42.
Wang et al., Effect of histone deacetylase inhibitor NL101 on rat neurons. Zhejiang Da Xue Bao Yi Xue Ban. May 2014;43(3):265-272. Abstract Only. 2 pages.

Wang et al., Independent validation of a model using cell line chemosensitivity to predict response to therapy. J Natl Cancer Inst. Sep. 4, 2013;105(17):1284-91.
Wang et al., Phase 1 trial of linifanib (ABT-869) in patients with refractory or relapsed acute myeloid leukemia. Leuk Lymphoma. Aug. 2012;53(8):1543-51.
Wang et al., Toward selective histone deacetylase inhibitor design: homology modeling, docking studies, and molecular dynamics simulations of human class I histone deacetylases. J Med Chem. Nov. 3, 2005;48(22):6936-47.
Watanabe et al., Modulation of renal disease in MRL/Ipr mice genetically deficient in the alternative complement pathway factor B. J Immunol. Jan. 15, 2000;164(2):786-94.
Weil et al., Breast cancer metastasis to the central nervous system. Am J Pathol. Oct. 2005;167(4):913-20.
Wiegmans et al., Differences in Expression of Key DNA Damage Repair Genes after Epigenetic-Induced BRCAness Dictate Synthetic Lethality with PARP1 Inhibition. Mol Cancer Ther. Oct. 2015;14(10):2321-31.
Wilson et al., Histone deacetylase 3 (HDAC3) and other class I HDACs regulate colon cell maturation and p21 expression and are deregulated in human colon cancer. J Biol Chem. May 12, 2006;281(19):13548-58.
Wilson et al., Relationship of p53, bcl-2, and tumor proliferation to clinical drug resistance in non-Hodgkin's lymphomas. Blood. Jan. 15, 1997;89(2):601-9.
Witzel et al., Long-term tumor remission under trastuzumab treatment for HER2 positive metastatic breast cancer—results from the HER-OS patient registry. BMC Cancer. Nov. 4, 2014;14:806. 7 pages.
Xiao et al., Antineutrophil cytoplasmic autoantibodies specific for myeloperoxidase cause glomerulonephritis and vasculitis in mice. J Clin Invest. Oct. 2002;110(7):955-63.
Xie et al., Quantitative structure-activity relationship study of histone deacetylase inhibitors. Curr Med Chem Anticancer Agents. May 2004;4(3):273-99.
Yan et al., Synergistic Inhibition of Tumor Growth and Overcoming Chemo-Resistance by Simultaneously Targeting Key Components in DNA Damage/Repair, Epigenetic, and Putative Cancer Stem Cell Signaling Pathways Using Novel Dual-Functional DNA-Alkylating/HDAC Inhibitor and Tumor Suppressor Gene Nanoparticles in Cancer Research. Cancer Research. Apr. 15, 2012;72(8, Suppl. 1) Proceedings: AACR 103rd Annual Meeting. Abstract 2741. 2 pages.
Yardley, Drug resistance and the role of combination chemotherapy in improving patient outcomes. Int J Breast Cancer. 2013;2013:137414. 15 pages.
Zaja et al., Bendamustine salvage therapy for T cell neoplasms. Ann Hematol. Sep. 2013;92(9):1249-54.
Zhang et al., A novel suberoylanilide hydroxamic acid histone deacetylase inhibitor derivative, N25, exhibiting improved antitumor activity in both human U251 and H460 cells. Asian Pac J Cancer Prev. 2014;15(10):4331-8.
Zhu et al., Histone deacetylase 3 implicated in the pathogenesis of children glioma by promoting glioma cell proliferation and migration. Brain Res. Jul. 3, 2013;1520:15-22.
Zinzani et al., Brentuximab Vedotin in Transplant-Naïve Relapsed/Refractory Hodgkin Lymphoma: Experience in 30 Patients. Oncologist. Dec. 2015;20(12):1413-6.
Zulkowski et al., Regression of brain metastases from breast carcinoma after chemotherapy with bendamustine. J Cancer Res Clin Oncol. Feb. 2002;128(2):111-3.
Hideshima et al., Mechanism of action of proteasome inhibitors and deacetylase inhibitors and the biological basis of synergy in multiple myeloma. Mol Cancer Ther. Nov. 2011;10(11):2034-42.
Munakata et al., The discovery and the development of bendamustine for the treatment of non-Hodgkin lymphoma. Expert Opin Drug Discov. Nov. 2016;11(11):1123-1130.
Ogura et al., A multicentre phase II study of vorinostat in patients with relapsed or refractory indolent B-cell non-Hodgkin lymphoma and mantle cell lymphoma. Br J Haematol. Jun. 2014;165(6):768-76.

(56) References Cited

OTHER PUBLICATIONS

Richardson et al., PANORAMA 2: panobinostat in combination with bortezomib and dexamethasone in patients with relapsed and bortezomib-refractory myeloma. Blood. Oct. 3, 2013;122(14):2331-7.

Chamberlain et al., Salvage therapy with single agent bendamustine for recurrent glioblastoma. J Neurooncol. Dec. 2011;105(3):523-30.

ClinicalTrials.gov, Study of EDO-S101, A First-in-Class Alkylating HDACi Fusion Molecule, in Relapsed/Refractory Hematologic Malignancies ClinicalTrials.gov Identifier: NTC02576496, 4 pages, Oct. 2015.

Mehrling, Mundipharma EDO GmbH Announces FDA Investigational New Drug Approval of its First anti-Cancer Compound, EDO-S101, for the Treatment of Patients with Relapsed/Refractory Haematologic Malignancies and Solid Tumours. EDO, http://mundipharma-edo.com/2015/07/31/mundipharma-edo-gmbh-announces-fda-investigational-new-drug-approval-of-its-first-anti-cancer-compound-edo-s101-for-the-treatment-of-patients-with-relapsedrefractory-haematologic-malignancies-and-s/. 2 pages, Jul. 31, 2015.

Mehrling, Mundipharma EDO GmbH announces first-in-human clinical trial of its lead compound, EDO-S101. EDO, http://mundipharma-edo.com/2016/07/20/mundipharma-edo-gmbh-announces-first-in-human-clinical-trial-of-lead-compound-edo-s101/. 2 pages, May 31, 2016.

Zinzani et al., Dose Escalation of Tinostamustine in Patients with Relapsed/Refractory (R/R) Lymphoid Malignancies. Retrieved online at: https://library.ehaweb.org/eha/2019/24th/266100/delphine.remmy.dose.escalation.of.tinostamustine.in.patients.with.relapsed.html?f=listing=3*browseby=8*sortby=1*media=1. 1 page, poster presentation. Jun. 1, 2019.

L428

L428-s

KMH2

L1236

L540

KMH2

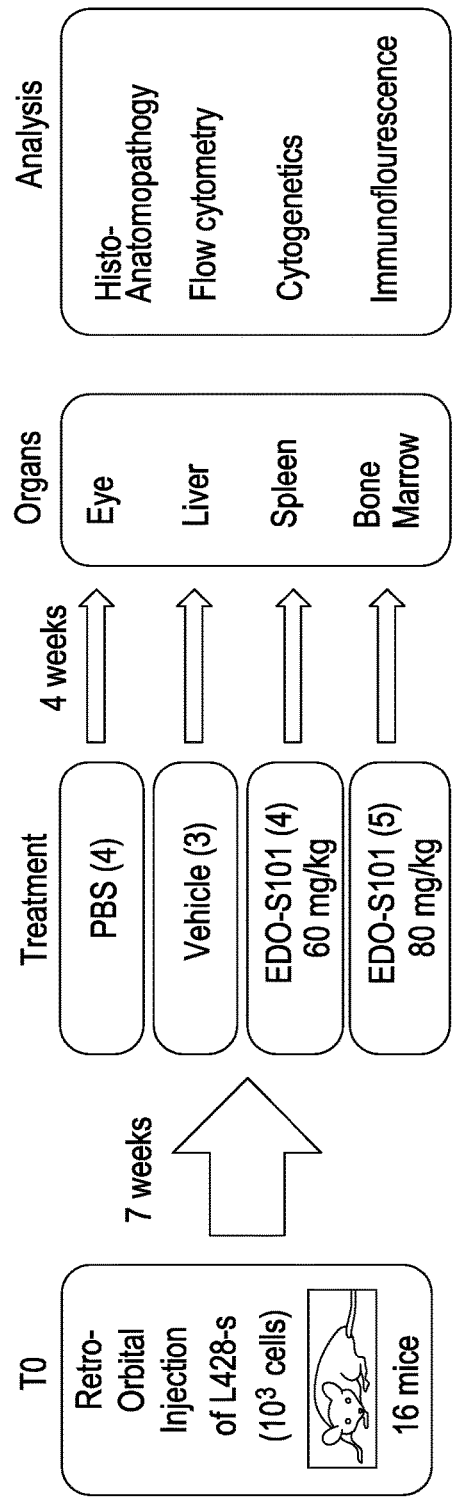
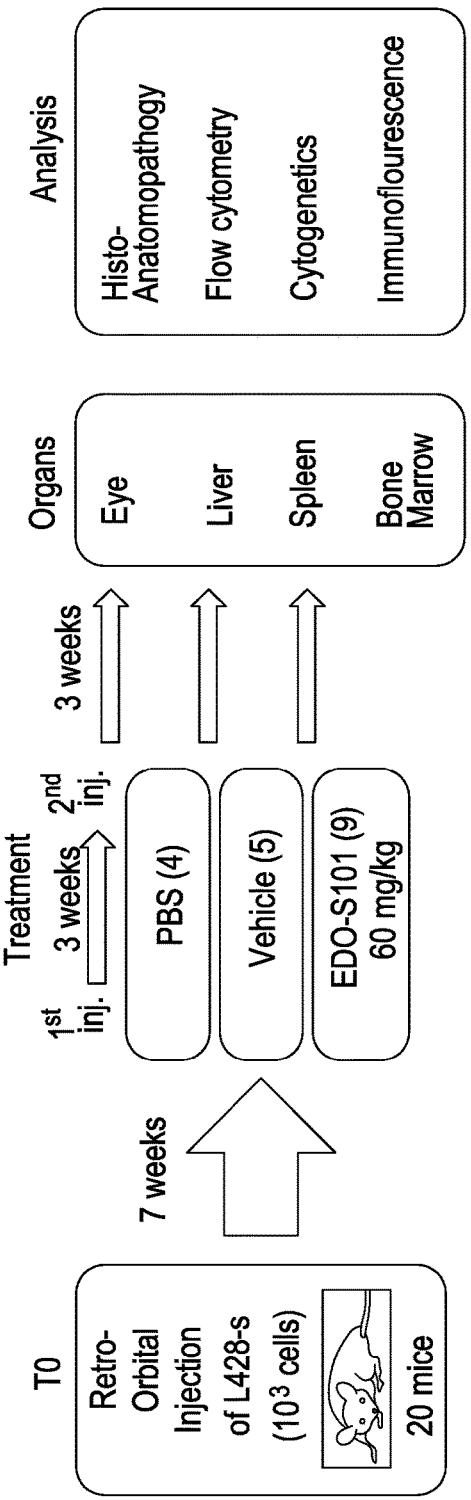
Figure 8a
Figure 8b

HODGKIN LYMPHOMA THERAPY

CROSS-REFERENCE TO RELATED APPLICATIONS

This application is a 35 U.S.C. § 371 national stage filing of International Application No. PCT/EP2016/074331, filed on Oct. 11, 2016, the entire contents of which are incorporated herein by reference.

TECHNICAL FIELD

The present invention relates to a method of treating Hodgkin lymphoma and to a combination and kit useful in a method of treating Hodgkin lymphoma.

BACKGROUND TO THE INVENTION

Cancer is one of the most life threatening diseases. Cancer is a condition in which cells in a part of the body experience out-of-control growth. According to latest data from American Cancer Society, it is estimated there will be 1.69 million new cases of cancer in USA in 2016. Cancer is the second leading cause of death in the United States (second only to heart disease) and will claim more than 595,000 lives in 2016. In fact, it is estimated that 50% of all men and 33% of all women living in the United States will develop some type of cancer in their lifetime. Therefore cancer constitutes a major public health burden and represents a significant cost in the United States. These figures are reflected elsewhere across most countries globally, although the types of cancer and relative proportions of the population developing the cancers vary depending upon many different factors such including genetics and diet.

For decades surgery, chemotherapy, and radiation were the established treatments for various cancers. Patients usually receive a combination of these treatments depending upon the type and extent of their disease. But chemotherapy is the most important option for cancer patients when surgical treatment (i.e. the removal of diseased tissue) is impossible. While surgery is sometimes effective in removing tumours located at certain sites, for example, in the breast, colon, and skin, it cannot be used in the treatment of tumours located in other areas, such as the backbone, nor in the treatment of disseminated hematologic cancers include cancers of the blood and blood-forming tissues (such as the bone marrow). They include multiple myeloma, lymphoma and leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism. It is used most often in the treatment of breast, lung, and testicular cancer. One of the main causes of failure in this treatment of cancer is the development of drug resistance by the cancer cells, a serious problem that may lead to recurrence of disease or even death. Thus, more effective cancer treatments are needed.

Lymphoma is a cancer of the lymphatic system. There are two main types of lymphoma, namely Hodgkin lymphoma and non Hodgkin lymphoma.

Non Hodgkin lymphoma is the more common form of lymphoma. The lymphatic system runs throughout the body, and it is therefore possible to find non Hodgkin lymphoma in almost all parts of the body. In patients with non Hodgkin lymphoma, some of their white blood cells (lymphocytes) divide abnormally. They do not have any resting time like normal cells and they start to divide continuously, so too many are produced. They do not naturally die off as they usually do. These cells start to divide before they are fully mature and therefore cannot fight infection as normal white blood cells do. All the abnormal lymphocytes start to collect in the lymph nodes or other places such as the bone marrow or spleen. They can then grow into tumours and begin to cause problems within the lymphatic system or the organ in which they are growing. For example, if a lymphoma starts in the thyroid gland it can affect the normal production of thyroid hormones. There are many different types of non Hodgkin lymphoma. They can be classified in several different ways. One way is by the type of cell affected. In non Hodgkin lymphoma two types of lymphocyte can be affected—B cells and T cells. This is classified as B cell lymphoma or a T cell lymphoma. Most people with non Hodgkin lymphoma have B cell lymphomas. T cell lymphomas are more common in teenagers and young adults.

Hodgkin lymphoma can occur in both children and adults, but it is most commonly diagnosed in young adults between 20 and 34 years of age. Approximately 9,000 new cases are diagnosed in the US each year. The cells of Hodgkin lymphoma have a particular appearance under the microscope. These cells are called Reed Sternberg cells. Non Hodgkin lymphomas do not have Reed Sternberg cells. It is important for doctors to be able to tell the difference between Hodgkin lymphoma and non Hodgkin lymphoma cells as they are two different diseases. In Hodgkin lymphoma, it is cells in the lymph nodes that have become cancerous.

Hodgkin lymphoma has been divided into two main classifications: classical Hodgkin lymphoma, which accounts for 90 to 95 percent of cases, and nodular lymphocyte predominant Hodgkin lymphoma. The type of Hodgkin lymphoma a patient may affect their treatment choices.

Classical Hodgkin Lymphoma

Nodular Sclerosis classical Hodgkin lymphoma is the most common subtype of classical Hodgkin lymphoma, accounting for 60 to 80 percent of all classical Hodgkin lymphoma cases. In nodular (knot-like) sclerosis classical Hodgkin lymphoma, the involved lymph nodes contain Reed Sternberg cells mixed with normal white blood cells. The lymph nodes often contain a lot of scar tissue, which is where the name nodular sclerosis (scarring) originates. The disease is more common in women than in men, and it usually affects adolescents and adults under the age of 50. The majority of patients are cured with current treatments.

Mixed cellularity classical Hodgkin lymphoma accounts for about 15 to 30 percent of all Hodgkin lymphoma cases. The disease is found more commonly in men than in women, and it primarily affects older adults. With this type of classical Hodgkin lymphoma, the lymph nodes contain many Reed Sternberg cells in addition to several other cell types. More advanced disease is usually present by the time this subtype is diagnosed.

Lymphocyte-Depletion classical Hodgkin lymphoma is rarely diagnosed. Abundant Reed Sternberg cells and few normal lymphocytes are present in the lymph nodes of patients with this subtype, which is aggressive and usually not diagnosed until it is widespread throughout the body.

Lymphocyte-Rich classical Hodgkin lymphoma accounts for less than five percent of Hodgkin lymphoma cases. The disease may be diffuse or nodular in form and is characterized by the presence of numerous normal-appearing lymphocytes and classic Reed Sternberg cells. This subtype of Hodgkin lymphoma is usually diagnosed at an early stage in adults and has a low relapse rate.

Lymphocyte Predominant Hodgkin Lymphoma

Nodular Lymphocyte Predominant Hodgkin lymphoma accounts for five to 10 percent of all Hodgkin lymphoma cases. It affects men more often than women and is usually diagnosed before the age of 35. In nodular lymphocyte predominant Hodgkin lymphoma, most of the lymphocytes found in the lymph nodes are normal (not cancerous). Typical Reed Sternberg cells are usually not found in this subtype, but large, abnormal B cells (sometimes referred to as popcorn cells) can be seen as well as small B cells, which may be distributed in a nodular pattern within the tissues. This subtype is usually diagnosed at an early stage and is not very aggressive. In many ways, this form of Hodgkin lymphoma resembles indolent B-cell non Hodgkin lymphoma with late recurrences.

The % survival rate over 5 years in 2015 for patients with non Hodgkin lymphoma was 63%, while the survival rate for those with Hodgkin lymphoma over the same period was 83%. Over 80 percent of patients with Hodgkin lymphoma survive for five years, and many are cured. Most patients treated for Hodgkin lymphoma will receive some form of chemotherapy, and sometimes radiation therapy, as their first treatment. The recommended first-line therapy for Hodgkin lymphoma is ABVD (adriamycin, bleomycin, vinblastine, and dacarbazine) with or without radiation therapy or other agents, depending on the patient's type and stage of Hodgkin lymphoma as well as their overall health status. Other chemotherapy regimens adopted include mechlorethamine, vincristine, prednisone, and procarbazine. Brentuximab vedotin (Adcetris) was approved in 2011 by the U.S. Food and Drug Administration for the treatment of relapsed/refractory Hodgkin lymphoma after stem cell transplantation or after failure of two previous chemotherapy regimens in patients who are not eligible for stem cell transplantation.

In WO-A-2010/085377, the compound of formula I below is disclosed. It is a first-in-class dual-functional alkylating-HDACi fusion molecule which potently inhibits the HDAC pathway.

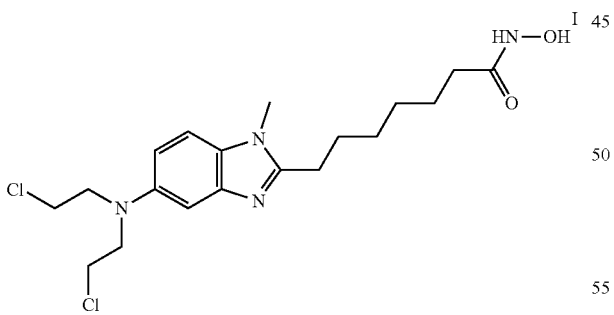

Biological assays showed that the compound of formula I potently inhibits HDAC enzyme (HDAC1 $IC_{50}$ of 9 nM).

There is a need for more effective treatments of Hodgkin lymphoma as many of the existing chemotherapy treatments are less than satisfactory.

SUMMARY OF THE INVENTION

In a first aspect of the present invention there is provided a method of treating Hodgkin lymphoma in a patient in need thereof comprising administering to said patient an effective amount of a compound of formula I or a pharmacologically acceptable salt thereof:

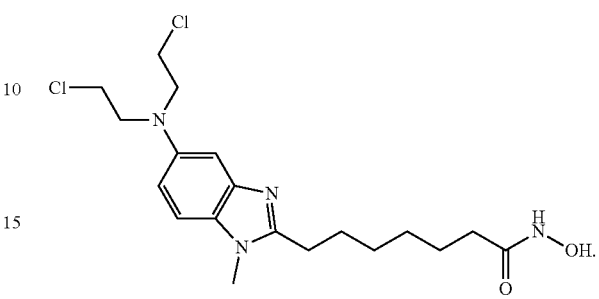

It has surprisingly been discovered that the compound of formula I or a pharmaceutically acceptable salt thereof is particularly effective in the treatment of Hodgkin lymphoma, with activity data showing strong sensitivity of all tested Hodgkin lymphoma cell lines to treatment with this compound. Thus, the need for a new and effective treatment of Hodgkin lymphoma is met by the present invention.

In a second aspect there is provided a compound of formula I or a pharmacologically acceptable salt thereof for use in a method of treating Hodgkin lymphoma in a patient in need thereof comprising administering to said patient an effective amount of said compound of formula I or a pharmacologically acceptable salt thereof.

In a third aspect of the present invention there is provided a combination comprising Brentuximab Vedotin and a compound of formula I or a pharmaceutically acceptable salt thereof.

In a fourth aspect of the present invention there is provided a kit comprising a combination according to the third aspect of the present invention, and optionally, instructions for treating a patient.

In a fifth aspect of the present invention there is provided a combination according to the third aspect of the present invention for use in therapy.

In a sixth aspect of the present invention there is provided a combination according to the third aspect of the present invention for use in a method of treating Hodgkin lymphoma in a patient in need thereof.

In a seventh aspect of the present invention there is provided a method of treating Hodgkin lymphoma in a patient in need thereof comprising administering to said patient a combination according to the third aspect of the present invention or a kit according to the fourth aspect of the invention.

DESCRIPTION OF THE DRAWINGS

FIGS. 8a and 8b show the two different dosage regimens used to test the NSG mice after xenografting with L428s Hodgkin lymphoma cells;

DETAILED DESCRIPTION OF THE INVENTION

Figure 1:
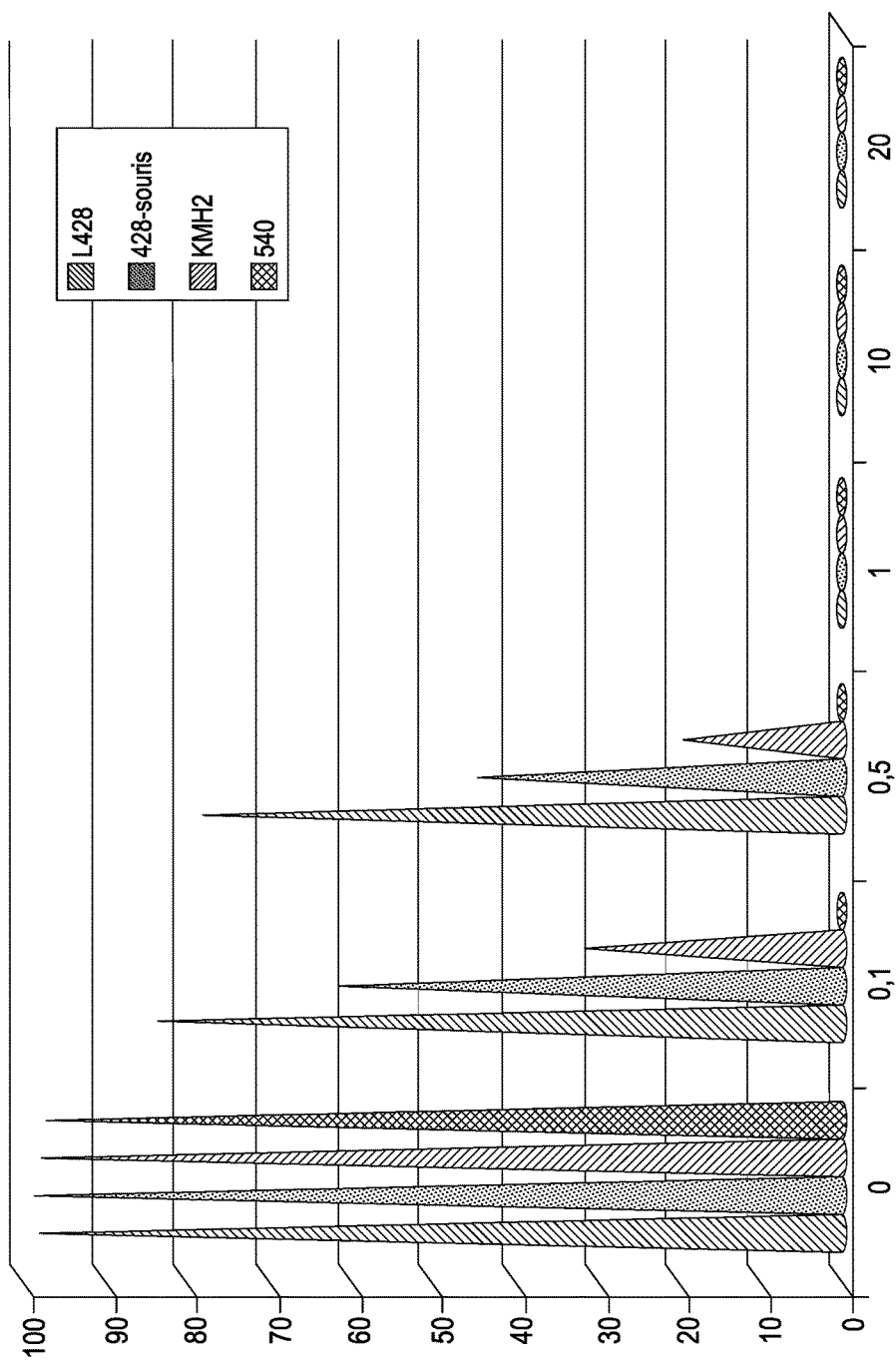
FIG. 1 is a plot of number of clones of four different Hodgkin lymphoma cell lines observed after culturing with the compound of formula I at six different concentrations.

In the present application, a number of general terms and phrases are used, which should be interpreted as follows.

"Patient" includes humans, non-human mammals (e.g., dogs, cats, rabbits, cattle, horses, sheep, goats, swine, deer, and the like) and non-mammals (e.g., birds, and the like).

"Pharmaceutically acceptable salts" means salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulfate, bisulfate, sulfamate, nitrate, phosphate, and organic acid addition salts such as, for example, acetate, trifluoroacetate, maleate, fumarate, citrate, oxalate, succinate, tartrate, salicylate, tosylate, lactate, naphthalenesulphonae, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

"Hodgkin lymphoma" is a cancer of the lymphatic system and it is characterized by particular appearance under the microscope. These cells are called Reed Sternberg cells. In Hodgkin lymphoma, it is cells in the lymph nodes that have become cancerous. Hodgkin lymphoma is divided into two main classifications: classical Hodgkin lymphoma, which accounts for 90 to 95 percent of cases, and lymphocyte predominant Hodgkin lymphoma.

The compound of formula I or a pharmaceutically acceptable salt thereof may be used in the treatment of Hodgkin lymphoma, either alone or in combination with Brentuximab Vedotin.

In one aspect of the first, second, sixth and seventh aspects of the present invention, the methods of the present invention may be used in the treatment of relapsed/refractory Hodgkin lymphoma. It is known from the art that bendamustine is a very active agent in the treatment of relapsed-refractory Hodgkin lymphoma (see, for example, Moskowitz et al, J. Clin. Oncol. 2013, 31, 456-60), with a reported complete response rate of 29 to 35% and an overall response rate of 50 to 58%. As previously explained, the compound of formula I or a pharmaceutically acceptable salt thereof includes a bendamustine alkylating moiety as part of its molecular structure. However, it is known that about 40% of relapsed/refractory Hodgkin lymphoma patients are resistant to bendamustine. Evidence included herein shows that the activity shown against relapsed/refractory Hodgkin lymphoma by known alkylating agents such as bendamustine is also demonstrated by the compound of formula I or a pharmaceutically acceptable salt thereof, either alone or in combination with Brentuximab Vedotin while the resistance that is shown to bendamustine is not experienced with the compound of formula I. The compound of formula I or a pharmaceutically acceptable salt thereof, alone or in combination with Brentuximab Vedotin is consequently a very promising therapy for the treatment of relapsed/refractory Hodgkin lymphoma.

In the method of the first aspect and second aspect of the present invention, the compound of formula I or a pharmaceutically acceptable salt thereof is not administered in combination with a compound selected from proteasome inhibitors, glucocorticoids and class III receptor tyrosine kinase inhibitors. In another embodiment of the first and second aspect of the present invention, the method of treating Hodgkin lymphoma is a monotheraputic treatment consisting of the administration of the compound of formula I or a pharmacologically acceptable salt thereof to the patient in need thereof.

In one preferred aspect of the third, fourth, fifth, sixth and seventh aspects of the present invention, the composition, kit or method is synergistic.

In the present invention, the pharmaceutically acceptable salt of the compound of formula I may preferably be the hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, oxalate, succinate, fumarate, tartrate, tosylate, mandelate, salicylate, lactate, p-toluenesulfonate, naphthalenesulfonate or acetate, and more preferably the acetate.

In the method of the first, second, sixth and seventh aspects of the present invention, the Hodgkin lymphoma is either classical Hodgkin lymphoma or lymphocyte predominant Hodgkin lymphoma.

The methods of the present invention are preferably directed to the treatment of classical Hodgkin lymphoma including nodular sclerosis classical Hodgkin lymphoma, mixed cellularity classical Hodgkin lymphoma, lymphocyte-depletion classical Hodgkin lymphoma and lymphocyte-rich classical Hodgkin lymphoma, and preferably nodular sclerosis classical Hodgkin lymphoma.

The methods of the present invention are alternatively directed to the treatment of lymphocyte predominant Hodgkin lymphoma such as nodular lymphocyte predominant Hodgkin lymphoma.

The therapeutically effective amount of the compound of formula I or a pharmacologically acceptable salt administered to the patient according to the methods of the first, second, sixth and seventh aspects of the present invention is an amount which confers a therapeutic effect in accordance with the present invention on the treated subject, at a reasonable benefit/risk ratio applicable to any medical treatment. The therapeutic effect may be objective (i.e. measurable by some test or marker) or subjective (i.e. subject gives an indication of or feels an effect). An effective amount of the compound of formula I or a pharmacologically acceptable salt thereof according to the first and second aspects of the present invention is believed to be one wherein the compound of formula I or a pharmacologically acceptable salt thereof is included at a dosage range of from 0.3 mg/m$^2$ to 300 mg/m$^2$ body surface area of the patient, preferably 1.5 mg/m$^2$ to 250 mg/m$^2$ body surface area of the patient, more preferably from 20 mg/m$^2$ to 150 mg/m$^2$ body surface area of the patient and most preferably from 40 mg/m$^2$ to 100 mg/m$^2$ body surface area of the patient, e.g. 40, 50, 60, 70, 80, 90 or 100 mg/m$^2$ body surface area of the patient.

In the combination according to the third aspect of the invention, the kit according to the fourth aspect of the present invention and the methods according to the fifth, sixth and seventh aspects of the present invention the compound of formula I or a pharmacologically acceptable salt thereof is included at a dosage range of from 0.3 mg/m$^2$ to 300 mg/m$^2$ body surface area of the patient, preferably 1.5 mg/m$^2$ to 150 mg/m$^2$ body surface area of the patient, more preferably from 10 mg/m$^2$ to 100 mg/m$^2$ body surface area of the patient and most preferably from 20 mg/m$^2$ to 80 mg/m$^2$ body surface area of the patient, e.g. 20, 30, 40, 50, 60, 70 or 80 mg/m$^2$ body surface area of the patient.

In the combination according to the third aspect of the invention, the kit according to the fourth aspect of the present invention and the methods according to the fifth, sixth and seventh aspects of the invention, BrentuximabVedotin is included at a dosage range of from 0.3 mg/m$^2$ to 300 mg/m$^2$ body surface area of the patient, more preferably from 0.5 mg/m$^2$ to 150 mg/m$^2$ body surface area of the patient and most preferably from 5 mg/m$^2$ to 100 mg/m$^2$ body surface area of the patient, e.g. 10, 20, 30, 40, 50, 60, 70, 80, 90 or 100 mg/m$^2$ body surface area of the patient.

The specific therapeutically effective dose level for any particular patient will depend upon a variety of factors including the specific form of Hodgkin lymphoma being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

Suitable examples of the administration form of the compound of formula I or a pharmacologically acceptable salt thereof and medicament comprising the same according, either alone or in combination with Brentuximab Vedotin to the present invention include without limitation oral, topical, parenteral, sublingual, rectal, vaginal, ocular, and intranasal. Parenteral administration includes subcutaneous injections, intravenous, intramuscular, intrasternal injection or infusion techniques. Preferably, the compound of formula I or a pharmacologically acceptable salt thereof and medicament comprising the same, either alone or in combination with Brentuximab Vedotin are administered parenterally, and most preferably intravenously.

Preferably, the compound of formula I or a pharmacologically acceptable salt thereof is administered intravenously in monotherapy in accordance with the methods of the first and second aspects of the present invention to the patient in need thereof at a dosage level to the patient in need thereof of from 0.3 to 100 mg/m$^2$ body surface area of the patient, preferably intravenously to the patient in need thereof at a dosage level to the patient in need thereof of from 1.5 mg/m$^2$ to 250 mg/m$^2$ body surface area of the patient, more preferably intravenously to the patient in need thereof at a dosage level to the patient in need thereof of from 20 mg/m$^2$ to 150 mg/m$^2$ body surface area of the patient and most preferably intravenously to the patient in need thereof at a dosage level to the patient in need thereof of from 40 mg/m$^2$ to 100 mg/m$^2$ body surface area of the patient, e.g. 40, 50, 60, 70, 80, 90 or 100 mg/m$^2$ body surface area of the patient.

Preferably, the compound of formula I or a pharmacologically acceptable salt thereof is administered in combination therapy according to the fifth, sixth and seventh aspects of the present invention intravenously to the patient in need thereof at a dosage level to the patient in need thereof of from 0.3 mg/m$^2$ to 300 mg/m$^2$ body surface area of the patient, preferably intravenously to the patient in need thereof at a dosage level to the patient in need thereof of from 1.5 mg/m$^2$ to 150 mg/m$^2$ body surface area of the patient and most preferably intravenously to the patient in need thereof at a dosage level to the patient in need thereof of from 20 mg/m$^2$ to 80 mg/m$^2$ body surface area of the patient, e.g. 20, 30, 40, 50, 60, 70 or 80 mg/m$^2$ body surface area of the patient.

Preferably, BrentuximabVedotin administered in combination therapy according to the fifth, sixth and seventh aspects of the present invention intravenously to the patient in need thereof at a dosage level to the patient in need thereof of from 0.3 mg/m$^2$ to 300 mg/m$^2$ body surface area of the patient, more preferably from 0.5 mg/m$^2$ to 150 mg/m$^2$ body surface area of the patient and most preferably from 5 mg/m$^2$ to 100 mg/m² body surface area of the patient, e.g. 10, 20, 30, 40, 50, 60, 70, 80, 90 or 100 mg/m² body surface area of the patient.

In the first and second aspects of the present invention, the compound of formula I or a pharmacologically acceptable salt thereof or medicament comprising said compound is preferably administered to a patient in need thereof on days 1, 8 and 15 of a treatment cycle, i.e. one treatment per week. This cycle lasts for 4 to 6 weeks, depending upon the patient, followed by a break of 1 to 3 weeks. In an alternative treatment cycle, the compound of formula I or a pharmacologically acceptable salt thereof or medicament comprising said compound is administered to a patient in need thereof on days 1 and 22 of the treatment cycle, i.e. one treatment every third week. There are altogether 3 to 12 cycles of treatment, preferably 5-8, and most preferably 6, depending upon the patient. In another alternative treatment cycle, the compound of formula I or a pharmacologically acceptable salt thereof or medicament comprising said compound is administered to a patient in need thereof on days 1 and 8 of the treatment cycle. Thus, one cycle lasts for one week and is repeated for 4 cycles. There is a fourth alternative treatment cycle, in which the compound of formula I or a pharmacologically acceptable salt thereof or medicament comprising said compound is administered to a patient in need thereof on days 1 and 15 of the treatment cycle. Each cycle last for two weeks and is repeated for 4 cycles.

In the methods of the fifth, sixth and seventh aspects of the present invention, the compound of formula I or a pharmaceutically acceptable salt thereof and Brentuximab Vedotin are also preferably administered according to the same treatment cycles as in the method of the first and second aspects of the present invention. However, within these cycles, the compound of formula I or a pharmaceutically acceptable salt thereof and Brentuximab Vedotin may be administered concurrently, sequentially or separately. If they are administered separately they are preferably administered from 1 to 6 hours apart, preferably 2 to 3 hours apart.

In one preferred embodiment of the first and second aspects of the invention, the compound of formula I or a pharmacologically acceptable salt thereof is administered intravenously to the patient in need thereof at a dosage level of from 40 mg/m² to 100 mg/m² body surface area of the patient on days 1, 8 and 15 of a treatment cycle, for 4 to 6 weeks, followed by a break of 1 to 3 weeks.

In an alternative embodiment of the first and second aspects of the invention, the compound of formula I or a pharmacologically acceptable salt thereof is administered intravenously to the patient in need thereof at a dosage level of from 40 mg/m² to 100 mg/m² body surface area of the patient on days 1 and 22 of a treatment cycle, for 3-12 consecutive cycles, more preferably 5-8 cycles and most preferably 6 cycles.

In one preferred embodiment of the first and second aspects of the invention, the compound of formula I or a pharmacologically acceptable salt thereof is administered intravenously to the patient in need thereof at a dosage level of 40 mg/m² to 100 mg/m² body surface area of the patient on days 1 and 15 of a treatment cycle, for 4 consecutive cycles.

In another preferred embodiment of the first and second aspects of the invention, the compound of formula I or a pharmacologically acceptable salt thereof is administered intravenously to the patient in need thereof at a dosage level of 40 mg/m² to 100 mg/m² body surface area of the patient on days 1 and 8 of a treatment cycle, for 4 consecutive cycles.

In one preferred embodiment of the fifth, sixth and seventh aspects of the present invention, the molar ratio of the compound of formula I or a pharmaceutically acceptable salt thereof to Brentuximab Vedotin is from 1:0.1 to 1:5, preferably 1:0.25 to 1:2.

In one preferred embodiment of the fifth, sixth and seventh aspects of the present invention, the compound of formula I or a pharmacologically acceptable salt thereof and Brentuximab Vedotin are administered separately over a period of 2 to 3 hours intravenously to the patient in need thereof on days 1, 8 and 15 of a treatment cycle, for 4 to 6 weeks, followed by a break of 1 to 3 weeks.

In an alternative embodiment of the fifth, sixth and seventh aspects of the present invention, the compound of formula I or a pharmacologically acceptable salt thereof and Brentuximab Vedotin are administered separately over a period of 2 to 3 hours intravenously to the patient in need thereof on days 1 and 22 of the treatment cycle, for 3 to 12 cycles of treatment, preferably 5 to 8 cycles , and most preferably 6 cycles.

In a further alternative embodiment of the fifth, sixth and seventh aspects of the present invention, the compound of formula I or a pharmacologically acceptable salt thereof and Brentuximab Vedotin are administered separately over a period of 2 to 3 hours intravenously to the patient in need thereof on days 1 and 8 of the treatment cycle, and this is repeated for 4 cycles.

In another embodiment of the fifth, sixth and seventh aspects of the present invention, the compound of formula I or a pharmacologically acceptable salt thereof and Brentuximab Vedotin are administered separately over a period of 2 to 3 hours intravenously to the patient in need thereof on days 1 and 15 of the treatment cycle, and this is repeated for 4 cycles.

In one preferred embodiment of the fifth, sixth and seventh aspects of the present invention, the compound of the compound of formula I or a pharmacologically acceptable salt thereof and Brentuximab Vedotin are administered intravenously to the patient in need thereof, wherein the compound of formula I or a pharmacologically acceptable salt thereof is administered intravenously at a dosage level of from 20 mg/m² to 80 mg/m² body surface area of the patient and Brentuximab Vedotin is administered intravenously to the patient in need thereof at a dosage level of from 5 mg/m² to 100 mg/m² body surface area of the patient on days 1, 8 and 15 of a treatment cycle, wherein the compound of formula I or a pharmaceutically acceptable salt thereof and Brentuximab Vedotin are administered separately over a period of 2 to 3 hours, and wherein the administration cycle is performed over a period of 4 to 6 weeks, followed by a break of 1 to 3 weeks.

In an alternative embodiment the fifth, sixth and seventh aspects of the present invention, the compound of the compound of formula I or a pharmacologically acceptable salt thereof and Brentuximab Vedotin are administered intravenously to the patient in need thereof, wherein the Substitute Specification compound of formula I or a pharmacologically acceptable salt thereof is administered intravenously at a dosage level of from 20 mg/m² to 80 mg/m² body surface area of the patient and Brentuximab Vedotin is administered intravenously to the patient in need thereof at a dosage level of from 5 mg/m² to 100 mg/m² body surface area of the patient on days 1 and 22 of a treatment cycle, wherein the compound of formula I or a pharmaceutically acceptable salt thereof and Brentuximab Vedotin are administered separately over a period of 2 to 3 hours, and wherein the administration cycle is performed over 3-12 consecutive cycles, more preferably 5-8 cycles and most preferably 6 cycles.

In another preferred embodiment of the fifth, sixth and seventh aspects of the present invention, the compound of formula I or a pharmacologically acceptable salt thereof and Brentuximab Vedotin are administered intravenously to the patient in need thereof, wherein the compound of formula I or a pharmacologically acceptable salt thereof is administered intravenously at a dosage level of from 20 mg/m$^2$ to 80 mg/m$^2$ body surface area of the patient and Brentuximab Vedotin is administered intravenously to the patient in need thereof at a dosage level of from 5 mg/m$^2$ to 100 mg/m$^2$ body surface area of the patient, wherein the compound of formula I or a pharmaceutically acceptable salt thereof and Brentuximab Vedotin are administered separately over a period of 2 to 3 hours, and wherein the administration cycle is performed on days 1 and 15 of a treatment cycle, for 4 consecutive cycles.

In another preferred embodiment of the fifth, sixth and seventh aspects of the present invention, the compound of formula I or a pharmacologically acceptable salt thereof and Brentuximab Vedotin are administered intravenously to the patient in need thereof, wherein the compound of formula I or a pharmacologically acceptable salt thereof is administered intravenously at a dosage level of from 20 mg/m$^2$ to 80 mg/m$^2$ body surface area of the patient and Brentuximab Vedotin is administered intravenously to the patient in need thereof at a dosage level of from 5 mg/m$^2$ to 100 mg/m$^2$ body surface area of the patient, wherein the compound of formula I or a pharmaceutically acceptable salt thereof and Brentuximab Vedotin are administered separately over a period of 2 to 3 hours, and wherein the administration cycle is performed on days 1 and 8 of a treatment cycle, for 4 consecutive cycles.

In the fourth aspect of the present invention, there is provided a kit comprising a combination according to the second aspect of the present invention and, optionally, instructions for treating a patient. Typically, a kit can comprise a compound of formula I or pharmaceutically acceptable Substitute Specification salt thereof and Brentuximab Vedotin together with instructions for treating a patient. Each active agent can be provided in a suitable container. The kit may further comprise a delivery system, e.g. for the compound of formula I or pharmaceutically acceptable salt thereof and Brentuximab Vedotin.

The instructions may advise administering BrentuximabVedotin and the compound of formula I or a pharmaceutically acceptable salt thereof concurrently, sequentially or separately according to variables such as the state of the Hodgkin lymphoma being treated; the activity of the specific compounds employed; the age, body weight, general health, sex and diet of the patient; the time of administration, route of administration, and rate of excretion of the specific compounds employed; the duration of the treatment; drugs used in combination or contemporaneously with the specific compounds employed; and like factors well known in the medical arts. Preferred kits according to the fourth aspect of the present invention include those comprising the preferred combinations of the present invention as described and exemplified above.

In a further embodiment of the methods of the first, second, fifth, sixth and seventh aspects of the present invention, the patient in need of said treatment is given radiotherapy prior to or after treatment of the Hodgkin lymphoma with the compound of formula I or a pharmacologically acceptable salt thereof (and, in the fourth aspect the Brentuximab Vedotin). Preferably, the patient is given radiotherapy treatment prior to the treatment with the compound of formula I or a pharmacologically acceptable salt thereof (and, in the fourth aspect the Brentuximab Vedotin) or the medicament comprising the same. The radiotherapy may be given at a dose of 1 to 5 Gy over 5 consecutive days and preferably 2 Gy over 5 consecutive days.

When intended for oral administration, the compound of formula I or a pharmacologically acceptable salt thereof or medicament comprising the same for use in the methods of treating Hodgkin lymphoma of the present invention or the combination of the third aspect of the present invention or in the kit according to the fourth aspect of the present invention may be in solid or liquid form, where semi-solid, semi-liquid, suspension and gel forms are included within the forms considered herein as either solid or liquid.

The compound of formula I or a pharmacologically acceptable salt thereof or medicament comprising the same for use in the methods of treating Hodgkin lymphoma of the present invention or the combination of the third aspect of the present invention or in the kit according to the fourth aspect of the present invention can be prepared for administration using methodology Substitute Specification well known in the pharmaceutical art. Examples of suitable pharmaceutical formulations and carriers are described in "Remington's Pharmaceutical Sciences" by E. W. Martin.

As a solid composition for oral administration, the compound of formula I or a pharmaceutically acceptable salt thereof or medicament comprising the same for use in the methods of treating Hodgkin lymphoma of the present invention or the combination of the second aspect of the present invention or in the kit according to the third aspect of the present invention can be formulated into a powder, granule, compressed tablet, pill, capsule, chewing gum, wafer or the like form. Such a solid composition typically contains one or more inert diluents, either as a single tablet comprising all active agents or as a number of separate solid compositions, each comprising a single active agent of the combination of the present invention (in the case of the kit). In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

When the compound of formula I or a pharmacologically acceptable salt thereof or medicament comprising the same for use in the methods of treating Hodgkin lymphoma of the present invention or the combination of the third aspect of the present invention or in the kit according to the fourth aspect of the present invention is in the form of a capsule (e. g. a gelatin capsule), it can contain, in addition to materials of the above type, a liquid carrier such as polyethylene glycol, cyclodextrin or a fatty oil.

The compound of formula I or a pharmacologically acceptable salt thereof or medicament comprising the same for use in the methods of treating Hodgkin lymphoma of the present invention or the combination of the third aspect of the present invention or in the kit according to the fourth aspect of the present invention can be in the form of a liquid, e. g. an elixir, syrup, solution, emulsion or suspension. The liquid can be useful for oral administration or for delivery by injection. When intended for oral administration, a compound of formula I or a pharmacologically acceptable salt thereof or medicament comprising the same for use in the methods of treating Hodgkin lymphoma of the present invention or the combination of the third aspect of the present invention or in the kit according to the fourth aspect of the present Substitute Specification invention can comprise one or more of a sweetening agent, preservatives, dye/colorant and flavor enhancer. In a compound of formula I or a pharmacologically acceptable salt thereof or medicament comprising the same for use in the method of treating Hodgkin lymphoma of the present invention for administration by injection, one or more of a surfactant, preservative, wetting agent, dispersing agent, suspending agent, buffer, stabilizer and isotonic agent can also be included.

Brentuximab Vedotin (trade name Adcetris®) is formulated for delivery by injection. It is stored as a white concentrated powder which is reconstituted with a sodium chloride solution for delivery to the desired concentration.

The preferred route of administration is parenteral administration including, but not limited to, intradermal, intramuscular, intraperitoneal, intravenous, subcutaneous, intranasal, epidural, intranasal, intracerebral, intraventricular, intrathecal, intravaginal or transdermal. The preferred mode of administration is left to the discretion of the practitioner, and will depend in part upon the site of the medical condition (such as the site of cancer). In a more preferred embodiment, the compound of formula I or a pharmacologically acceptable salt thereof is administered intravenously.

The liquid compound of formula I or a pharmacologically acceptable salt thereof or medicament comprising the same for use in the methods of treating Hodgkin lymphoma of the present invention or in the combination of the third aspect of the present invention or in the kit according to the fourth aspect of the present invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A parenteral combination or composition can be enclosed in an ampoule, a disposable syringe or a multiple-dose vial made of glass, plastic or other material. Physiological saline is a preferred adjuvant.

The compound of formula I or a pharmacologically acceptable salt thereof or medicament comprising the same for use in the method of treating Hodgkin lymphoma of the present invention can be administered by any convenient route, for example by infusion or bolus injection, by absorption through epithelial or mucocutaneous linings, and preferably by bolus injection.

EXAMPLES

In the following examples, the compound having the following formula I is referred to as EDO-S101.

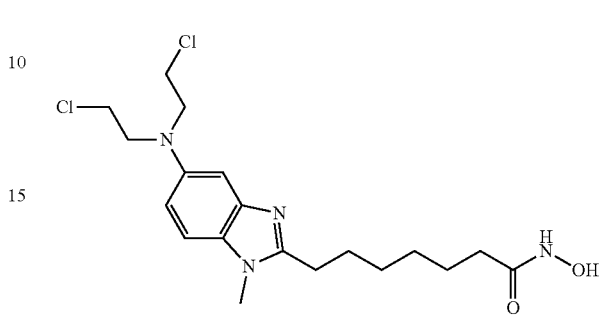

EDO-S101 may be prepared as described in Example 6 of WO-A-2010/085377.

Example 1 Hodgkin Lymphoma Cell Lines

In all examples, the human Hodgkin lymphoma-derived cell lines L428, L428-c, KMH2, L591, L540, L1236, HDLM2 and SUP-HD were obtained from Dr Steffen Junker (Aarhus University Denmark). All cell lines were cultured in Gibco RPMI 1640 medium supplemented with Glutamax, 10% FBS and antibiotics at 37° C. Some cell lines exhibited higher growth and others relatively slow growth. The immunophenotype, P53 status and MSI characterization of the Hodgkin lymphoma cell lines was determined using anti-CD30, CD15, CD20 and CD14 antibodies.

Table 1 below shows the origin and histological type of the cell lines. Five cell lines were nodular sclerosis Hodgkin lymphoma cell lines and two cell lines were mixed cellularity Hodgkin lymphoma cell lines, thus covering the two most common forms of Hodgkin lymphoma.

TABLE 1

| Cell line | Origin | Histology Type | EBV status | Derived patients (age) |
|---|---|---|---|---|
| KMH2 | B-cell | mixed cellularity | – | Male (37) |
| L1236 | B-cell | mixed cellularity | – | Male (34) |
| L428 | B-cell | nodular sclerosis | – | Female (37) |
| SUP-HD1 | B-cell | nodular sclerosis | – | Male (33) |
| L591 | B-cell | nodular sclerosis | + | Female (31) |
| HDLM2 | T-cell | nodular sclerosis | – | Male (74) |
| L540 | T-cell | nodular sclerosis | – | Female (20) |

EBV status = indication of presence or otherwise of the Epstein-Barr virus genome.

To determine the functional status of p53, a functional yeast assay was performed as described in Flaman et al., Proc. Natl. Acad. Sci. USA 1995 Apr. 25, 92 (9), 3963-3967. This analysis showed the showed presence of 100% yeast colonies of red color in three cell lines, indicating nonfunctional status of p53. Sequencing of p53 cDNA confirmed the presence of mutations in L428 (exon 4), L1236 (exon 10-11) and HDLM2 (exon 8-11) (see Table 2 below).

TABLE 2

| Cell line | P53 mutated | Microsatellite (MSI) |
|---|---|---|
| KMH2 | − | 3/5 |
| L1236 | + (exon10-11) | 0/5 |
| L428 | + (exon4) | 4/5 |
| SUP-HD1 | − | NA |
| L591 | − | 1/5 |
| HDLM2 | + (exon 8-11) | 3/5 |
| L540 | − | 1/5 |

Microsatellite instability (MSI) is the condition of genetic hypermutability that results from impaired DNA Mismatch Repair. In other words, microsatellite instability is the phenotypic evidence that Mismatch Repair is not functioning normally. DNA Mismatch Repair corrects errors that spontaneously occur during DNA replication like single base mismatches or short insertions and deletions. The proteins involved in Mismatch Repair form a complex that binds to the mismatch, identifies the correct strand of DNA, then subsequently excises the error and repairs the mismatch. Cells with abnormally functioning Mismatch Repair tend to accumulate errors rather than correcting those errors. As a result, gene sequences are not preserved faithfully through DNA replication, and novel microsatellite fragments are created. Microsatellite instability is detected by PCR based assays that reveal these novel microsatellites.

Microsatellites are repeated sequences of DNA. These sequences can be made of repeating units of 1-6 base pairs in length. Although the length of these microsatellites is highly variable from person to person (part of DNA "fingerprint"), each individual has microsatellites of a set length. The most common microsatellite in humans is a dinucleotide repeat of CA, which occurs tens of thousands of times across the genome. Microsatellites are also known as simple sequence repeats (SSRs).

Example 2 Clonogenic Survival of Hodgkin Lymphoma Cell Lines Treated by EDO-S101

This test was performed on four Hodgkin lymphoma cell lines (L428, L428s, KMH2 and L540). Each was cultured with EDO-S101 at doses of 0, 0.1, 0.5, 1, 10 and 20 μmol in DMSO. The cell lines were cultured in methylcellulose (Stem cell Technologies) at a concentration of $10^5$/ml at 37° C. and 5% $CO_2$. The surviving fraction was determined by measuring the viability of colonies generated before and after exposure. Only colonies with more than 50 cells were counted. The results are shown in FIG. 1. Each data point represents the average and SD from three independent experiments performed in triplicate.

No clone was observed for the L540 cell line following treatment at any dose indicating a high sensitivity of this cell line to EDO-S101 treatment.

Similarly, the KMH2 cell line exhibited a high sensitivity, as only a few clones, characterized by their large size, were observed at the lowest doses of EDO-101 tested (0.1 and 0.5 μmol).

L428 and L428s also exhibited a high sensitivity, with only macrophagic clones being observed after exposure to very low doses (0.1 and 0.5 μmol).

It can further be seen that both p53 positive and negative cell lines were sensitive to EDO-S101 treatment. This is important as it is known from the art (e.g. see Wilson et al, Blood, 89, 2, 1997, 601-609) that the p53 gene plays a part in clinical drug resistance in Hodgkin lymphoma. The fact that EDO-S101 is active against both p53+ and p53− Hodgkin cell lines is strongly suggestive that it may be active in the treatment of relapsed/refractory Hodgkin lymphoma.

Example 3 Mitotic Index and Induced Chromosomal Aberrations After EDO-S101 Treatment The mitotic index and chromosomal aberrations for each of the cell lines were evaluated after treatment with either 20 μmol or 10 μmol EDO-S101 in DMSO. Each cell line was cultured at 37° C. in the presence of RPMI 1640 supplemented with 10% FCS and antibiotics. Colcemid (0.1 ug/ml) was added 2 h before harvesting and slides with chromosomes in metaphase were prepared following the standard methanol/acetic acid (3/1, v/v) procedure. The slides were stored at −20° C. until use.

FISH was performed using a combination of standard procedures from the recommended protocols for chromosome analysis, following telomere and centromere staining, using PNA probes. In all, 100 metaphases were scored per in vitro dose exposure.

No metaphases were observed following the 20 μmol EDO-S101 treatment for any cell line and only a few metaphases of poor quality were observed following 10 μmol EDO-S101 treatment. The metaphase of the KMH2 cell line exhibited numerous chromosomal aberrations (detected using telomere and centromere staining).

Figure 2:
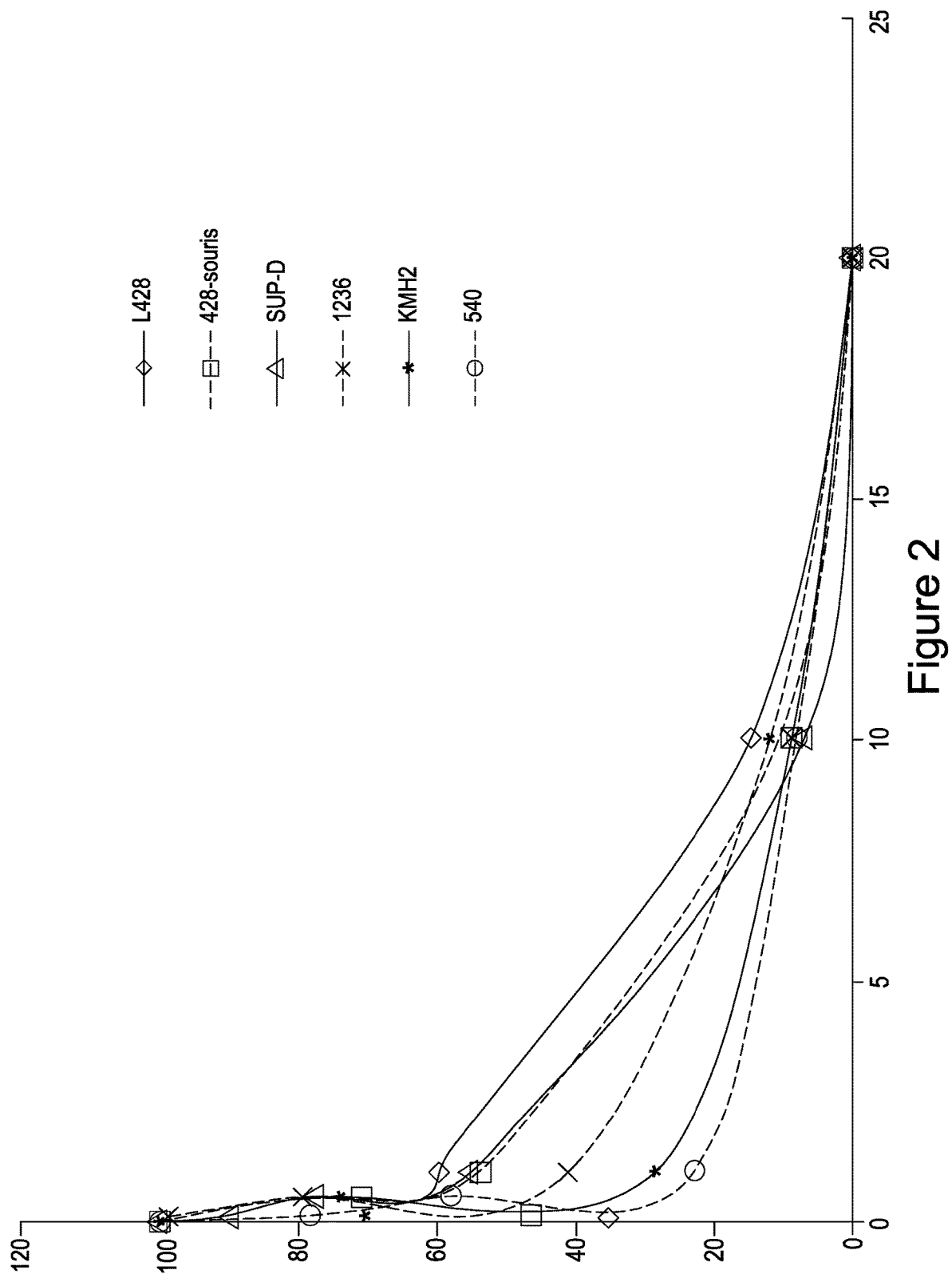
FIG. 2 is a plot of the mitotic index for six different Hodgkin lymphoma cell lines observed after culturing with the compound of formula I.
Figure 3A:
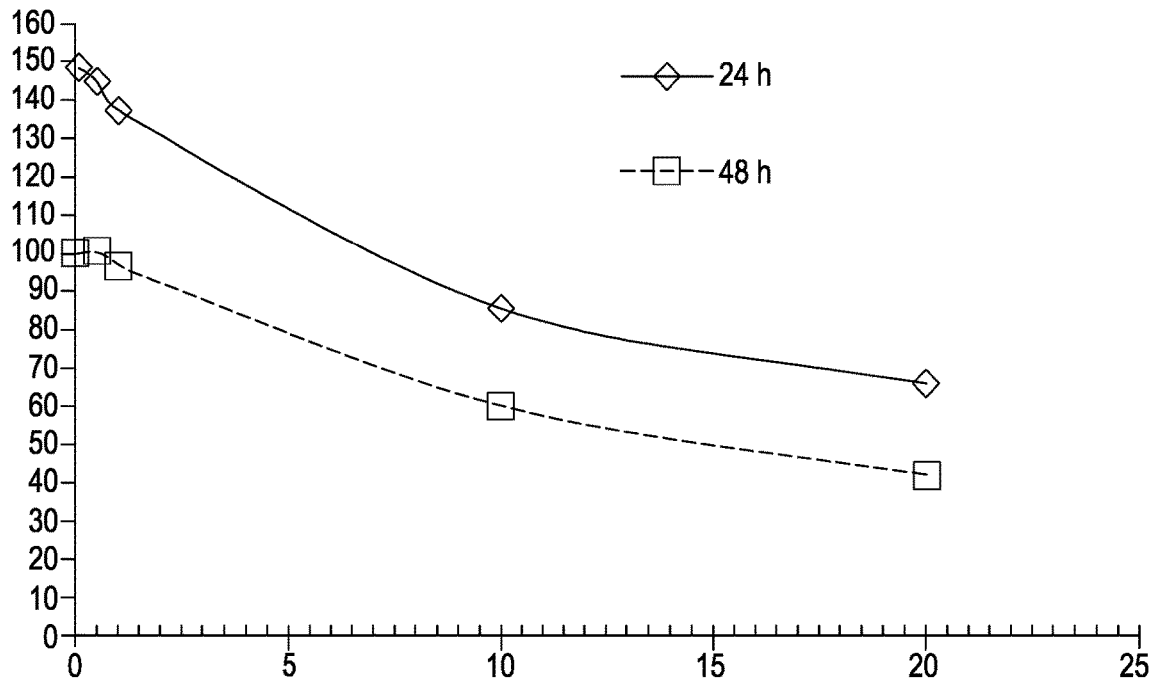
FIGS. 3a to 3i are plots of cell proliferation for nine different Hodgkin lymphoma cell lines against concentration of the compound of formula I administered after culturing said cell line with said compound for 24 hours and 48 hours.
Figure 3B:
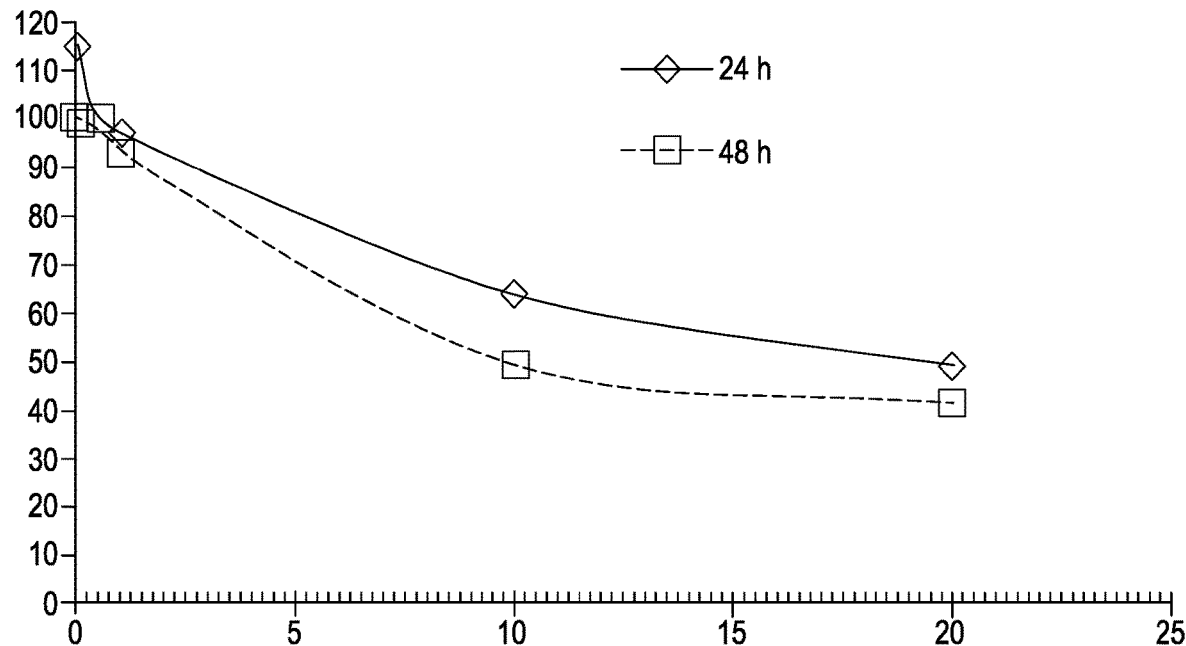
Figure 3C:
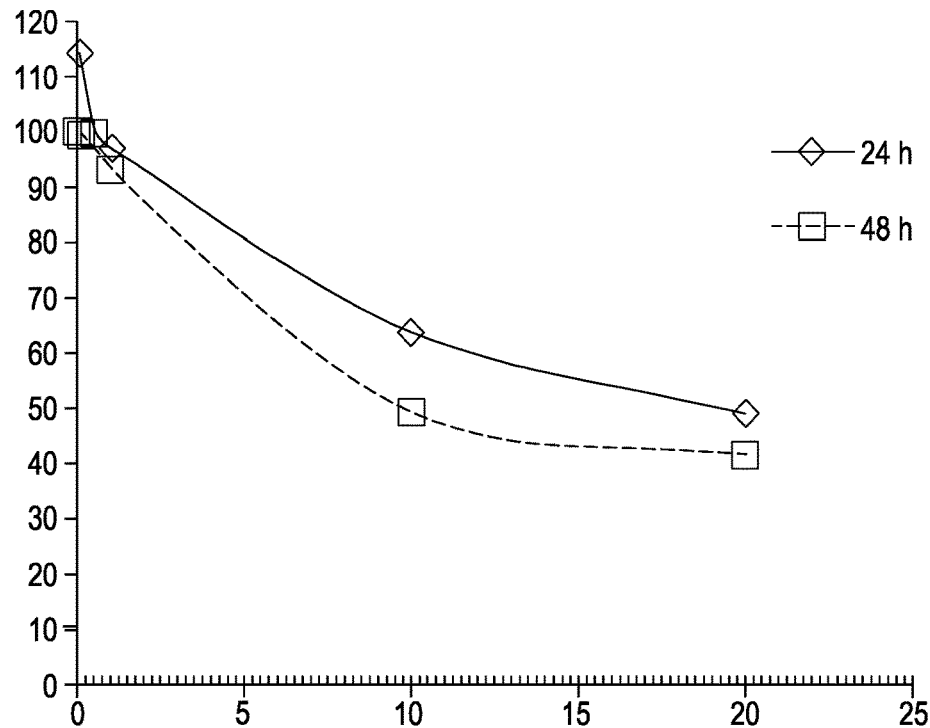
Figure 3D:
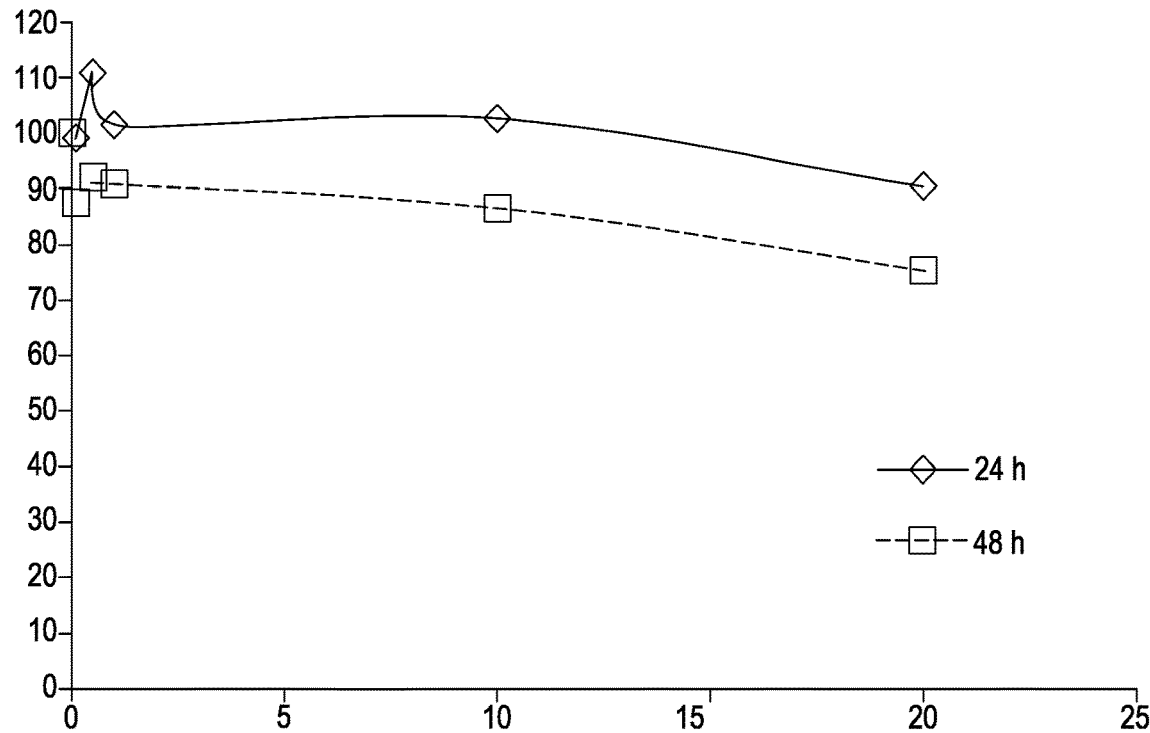
Figure 3E:
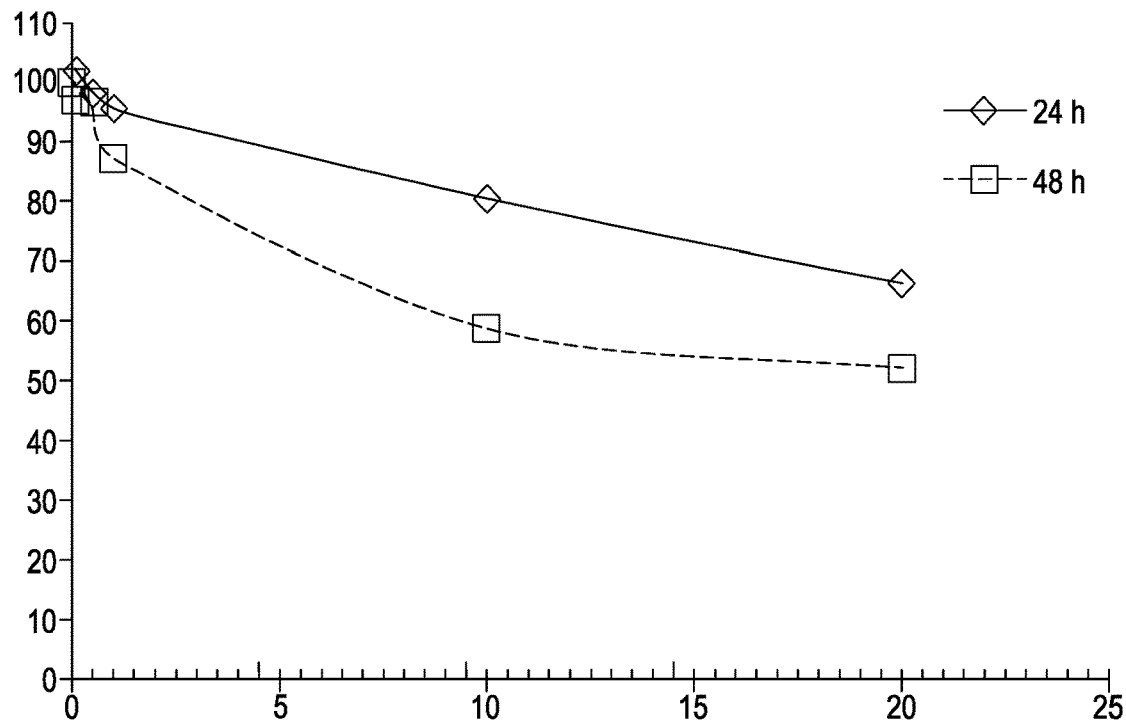
Figure 3F:
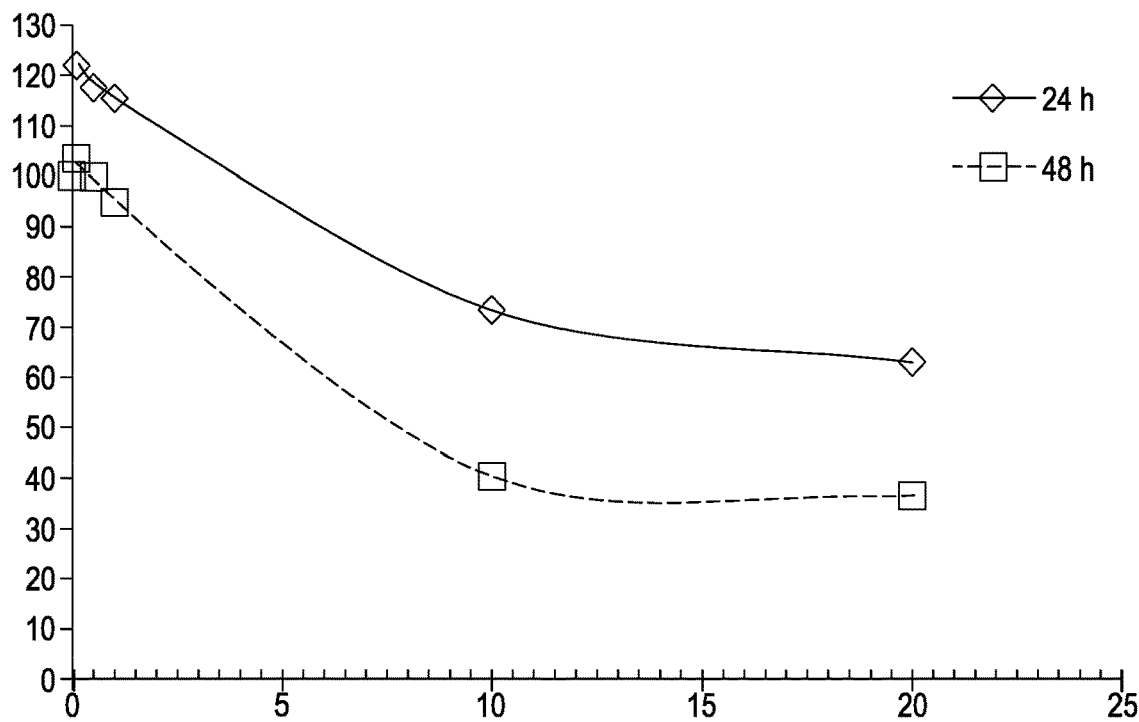
Figure 3G:
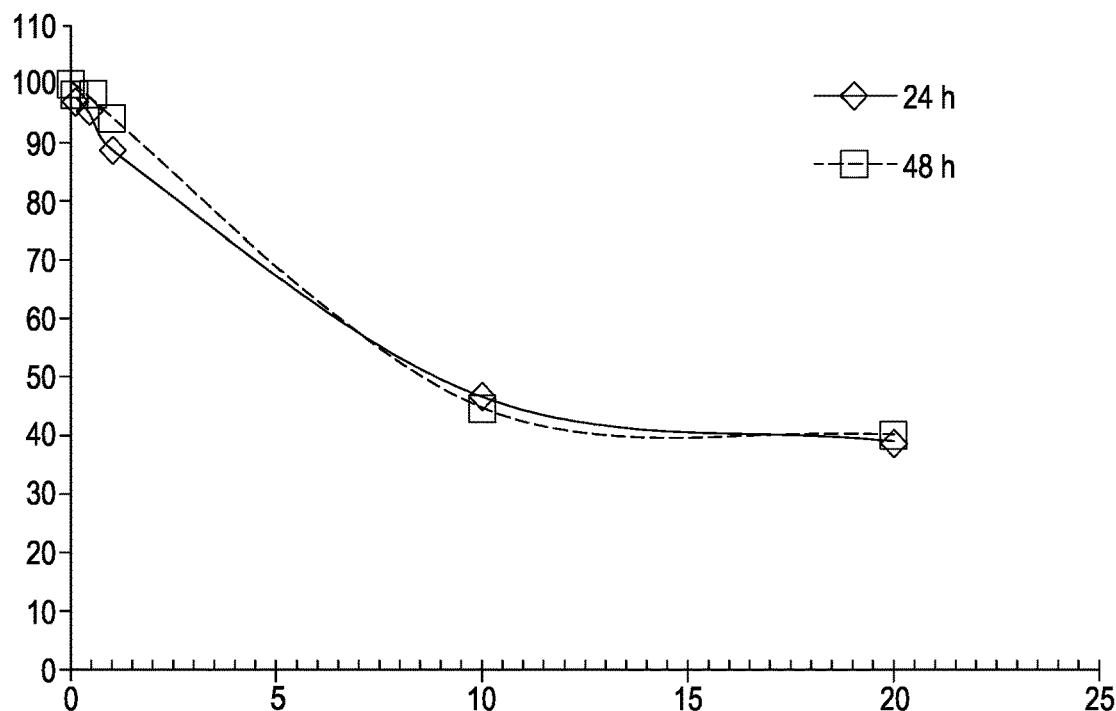
Figure 3H:
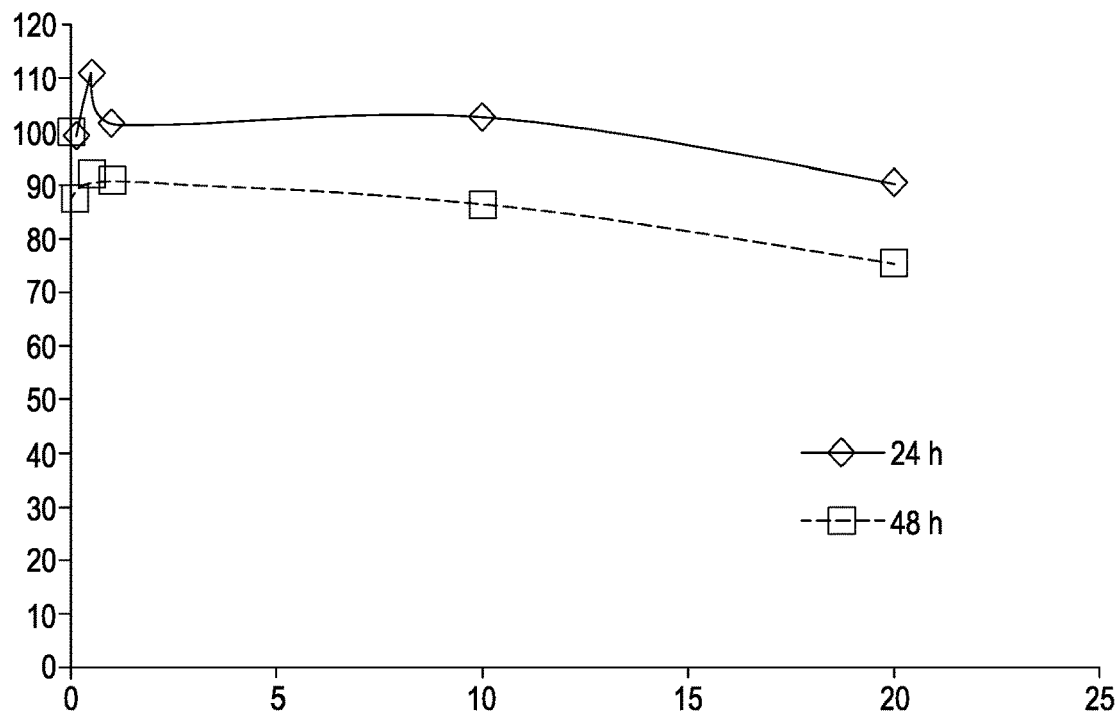
Figure 3I:
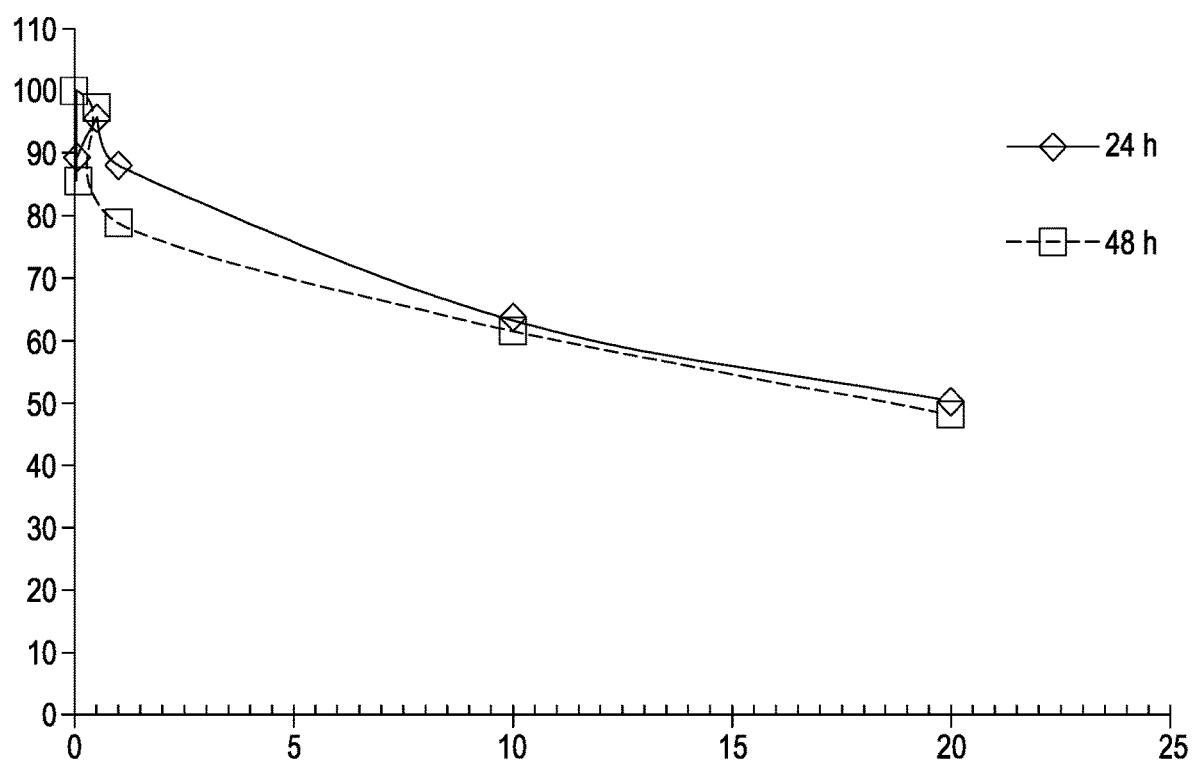
Figure 4A:
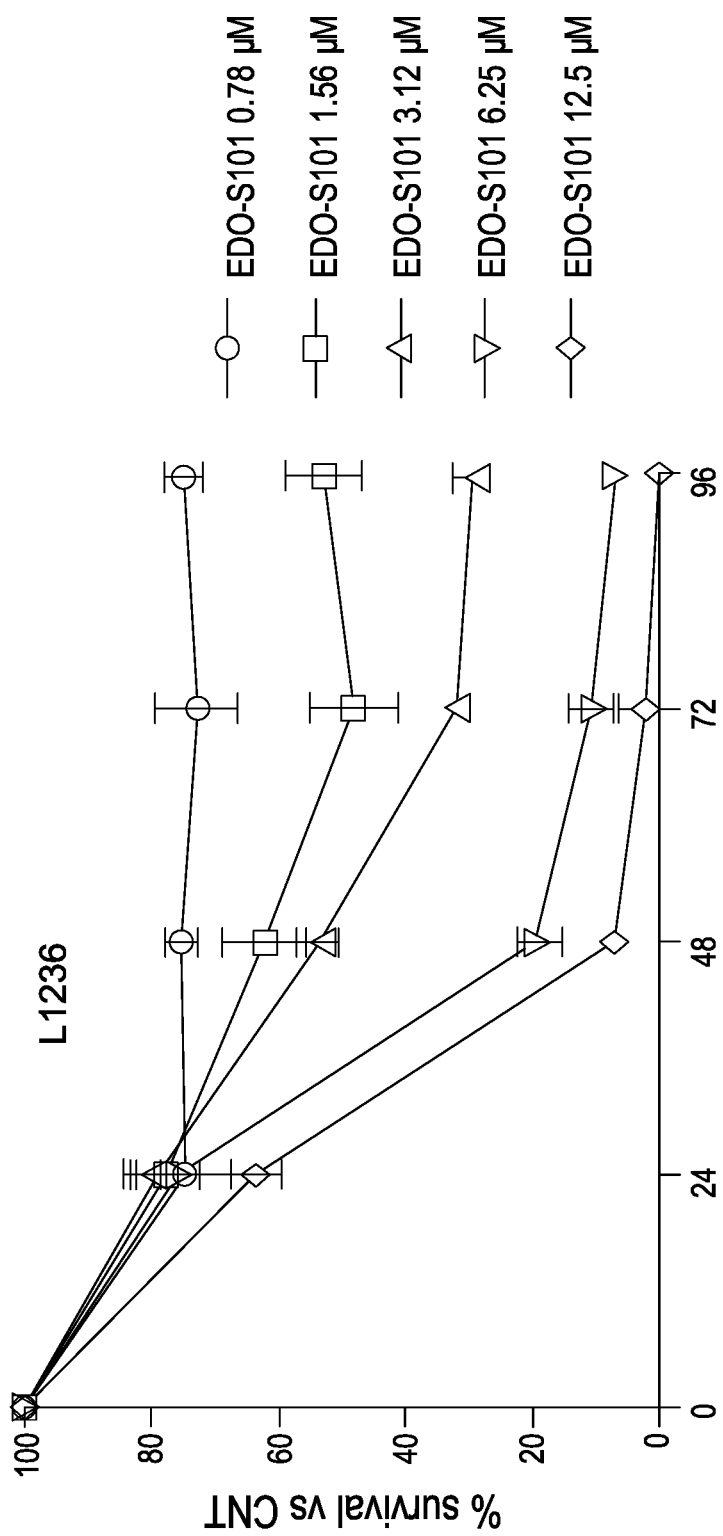
FIGS. 4a to 4e are plots of % survival of five different cell lines 0, 24, 48, 72 and 96 hours after administration of varying concentrations of the compound of formula I to said cell lines.
Figure 4B:
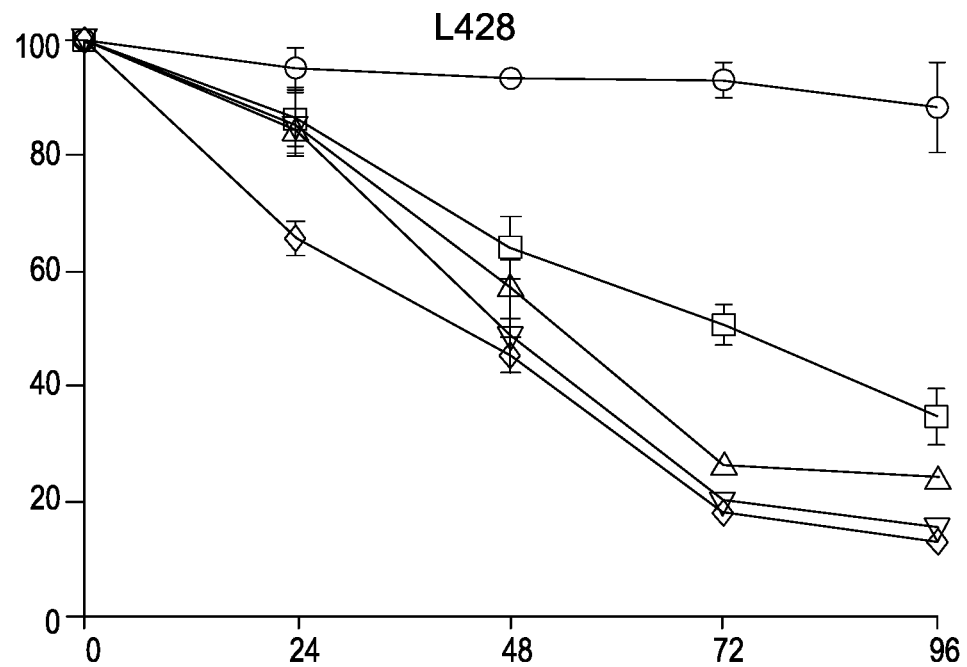
Figure 4C:
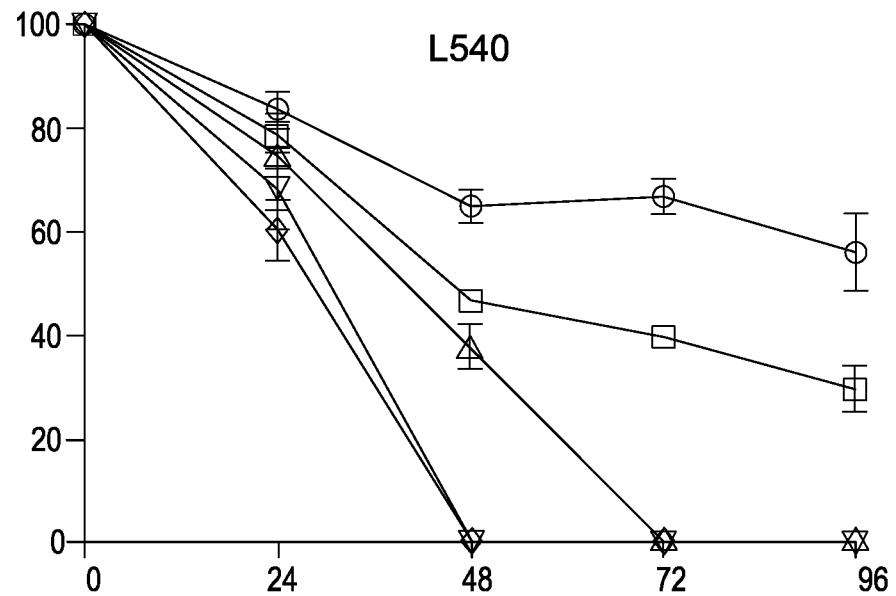
Figure 4D:
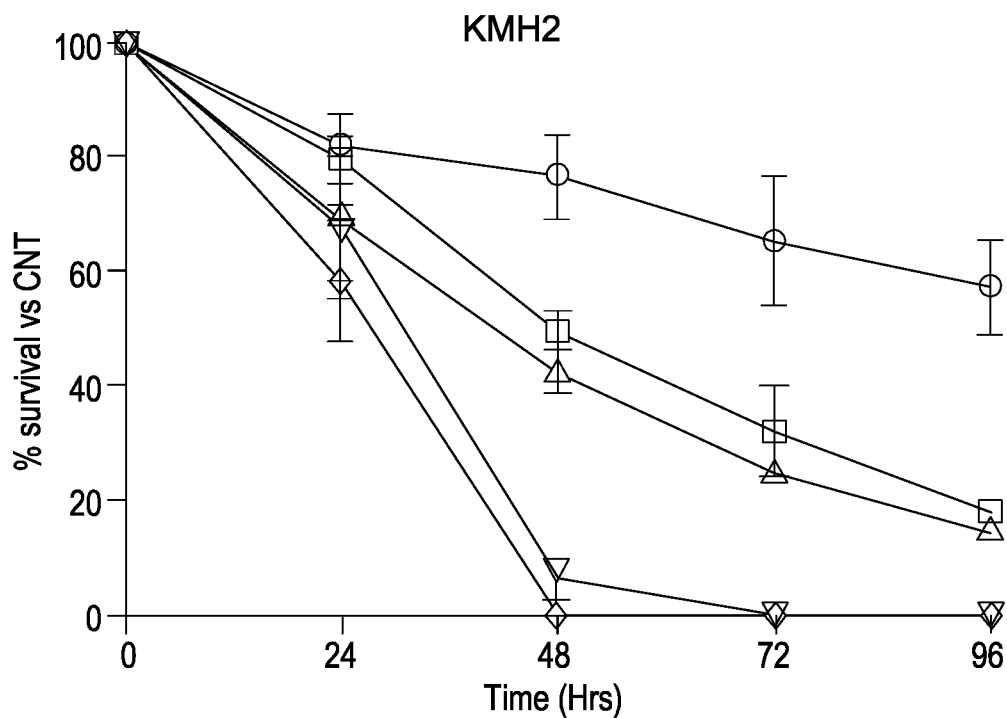
Figure 4E:
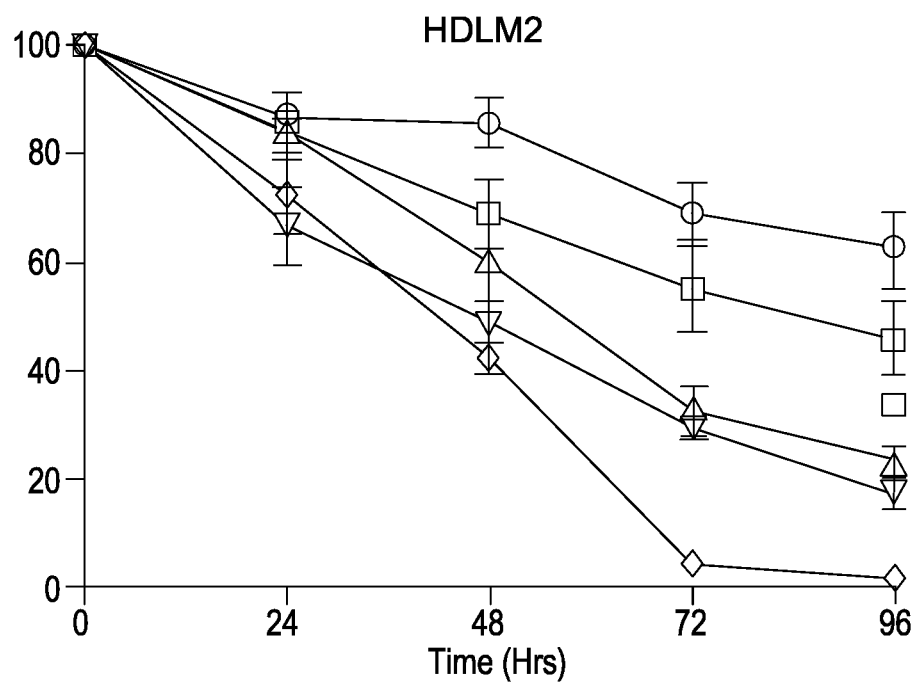

Of note, the L540 and KMH2 cell lines exhibited a very low mitotic index. The mitotic index assay, the results of which are shown in FIG. 2, demonstrated a remarkably high sensitivity of all Hodgkin lymphoma cell lines to EDO-S101 after only 24 h of treatment. The mitotic index was determined by measurement of the sum of all cells in prophase, metaphase, anaphase and telophase divided by the total number of cells.

Example 4 Proliferation and IC50 Determination

Nine Hodgkin lymphoma cell lines were cultured at 37° C. in 24-well plates at a concentration of $0.3 \times 10^6$ cells/ml in the presence of EDO-S101 at concentrations of 0, 5, 10, 15 and 20 μmol in DMSO for 24 hours and 48 hours and the proliferation of the cells was determined using a non-radioactive cell proliferation MTS assay with CellTiter 96® Aqueous One solution reagent obtained from Promega® (this is a colorimetric method for determining the number of viable cells in a proliferation comprising a tetrazolium compound [3-(4,5-dimethylthiazol-2-yl)-5-(3-carboxymethoxyphenyl)-2-(4-sulfophenyl)-2H-tetrazolium, inner salt; MTS). The proliferation was plotted against concentration of EDO-S101 for treatment after both 24 and 48 hours. As can be seen from FIGS. 3a to 3i and Table 3 below, EDO-S101 showed very strong anti-proliferative activity against all the Hodgkin lymphoma cell lines, with the IC50 ranging between 6.3 μM and 1.6 μM at 48 h following manual counting using Trypan blue.

TABLE 3

| Cell Lines | Cell Lines |
|---|---|
| L428 | L428 |
| L428-S | L428-S |
| L540 | L540 |
| L1236 | L1236 |
| SUP-HD | SUP-HD |

TABLE 3-continued

| Cell Lines | Cell Lines |
|---|---|
| L591 | L591 |
| HDLM2 | HDLM2 |
| KMH2 | KMH2 |

There are some difference between the results obtained using this test compared to that obtained using manual scoring or clonogenic survival. This difference was due essentially to the sensitivity and the specificity of this test. This test measured the activity of the proliferation of the Hodgkin lymphoma cells and not the proliferation in terms of cell division.

Example 5 Dose and Time-Dependent Effects of EDO-S101 on Hodgkin Lymphoma Cell Growth Five Hodgkin lymphoma cell lines (KMH2, HDML2, L540, L1236 and L426) were cultured in the presence of EDO-S101 dissolved in DMSO at concentrations of 0.78 µM, 1.56 µM, 3.12 µM, 6.25 µM and 12.5 µM at 37° C. Control cells were cultured in the same final concentration of DMSO. The cell viability, calculated as the % cell survival vs. control (CNT) was assessed at 24, 48, 72 and 96 hours through a Countess™ automated cell counter (Invitrogen), each experiment being repeated three times and the results given being the mean of the three results±SD. The results are shown in FIGS. 4a to 4e.

Figure 5:
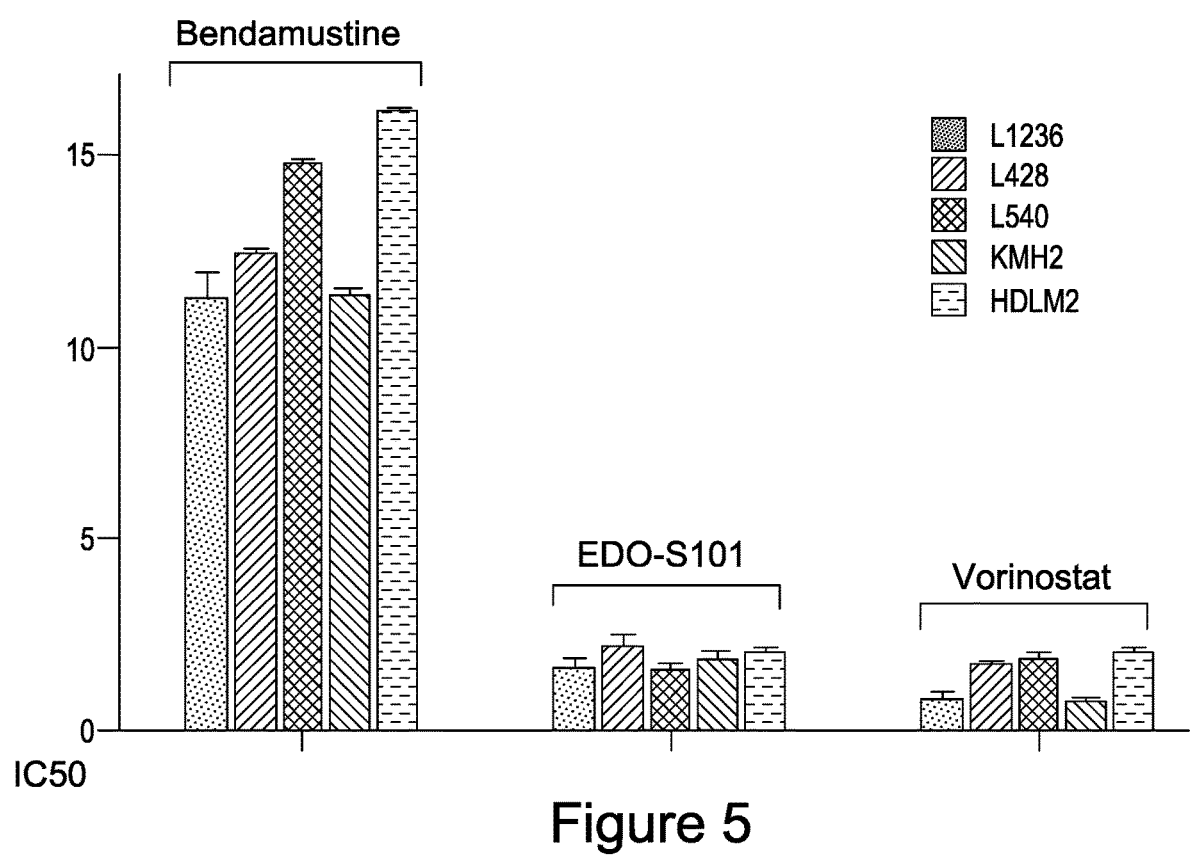
FIG. 5 shows the IC50 values for bendamustine, the compound of formula I and vorinostat against five different Hodgkin lymphoma cell lines.

Example 6 Comparison of IC50s and Anti-Proliferative Effects of Bendamustine, Vorinostat and EDO-S101 Against Hodgkin Lymphoma Cell Lines (a) Five Hodgkin lymphoma cell lines (KMH2, HDML2, L540, L1236 and L426) were cultured separately in the presence of bendamustine, vorinostat and EDO-S101 dissolved in DMSO at 37° C. L1236-derived Hodgkin lymphoma cell lines were selected as they have an acquired stable resistance to bendamustine (R100) or an ability to display continuous growth upon extended exposure to sub-lethal concentrations of bendamustine (R25, R50 and R75). A detailed description of the L1236-R Hodgkin lymphoma cell lines is disclosed in De Filippi et al, ASH 2015, Abstract. # 2479. In these tests, the L1236-100R bendamustine resistant strain was used. As can be seen from FIG. 5, the IC50 values for all cell lines cultured with bendamustine were high, ranging between 11 and 17 µM. On the other hand, the IC50 values for all Hodgkin lymphoma cell lines tested, including the bendamustine resistant cell line L1236-R were of an order of magnitude lower for EDO-S101, in the range 1 to 2 µM and similar to the known anti-lymphoma agent vorinostat.

(b) The bendamustine-resistant Hodgkin lymphoma cell line L1236-R100, non-resistant L1236 Hodgkin lymphoma cell line cultured in DMSO L1236/DMSO and L1236 was cultured in the presence of EDO-S101 dissolved in DMSO at concentrations of 0.78 µM, 1.56 µM, 3.12 µM, 6.25 µM and 12.5 µM. Control cells were cultured in the same final concentration of DMSO. The number of viable cells was assessed at 24, 48 and 72 hours through a Countess™ automated cell counter (Invitrogen), each experiment being repeated three times and the results given being the mean of the three results±SD. These results were used to produce a plot of the number of viable cells against time at 24, 48 and 72 hours for each of the three cell lines after treating with bendamustine, EDO-S101 and vorinostat (see FIG. 6a for the R100 cell line) and the IC50 (µM) for each of bendamustine, EDO-S101 and vorinostat against each of the three Hodgkin lymphoma cell lines tested (se FIG. 6b).

As will be immediately apparent, and as would be expected, the IC50 values for bendamustine against the R100 cell line are very high indeed, in the region of 140 µM, while it also shows high IC50 values against the non-resistant L1236 Hodgkin lymphoma cell lines. Thus, the anti-proliferative activity of bendamustine is quite low. Surprisingly, however, EDO-S101 showed remarkable anti-proliferative activity against all Hodgkin lymphoma cell lines tested, including the R100 cell line, with IC50 values in the range of approximately 1 to 3 µM, approximately two orders of magnitude greater than for bendamustine.

Figure 6A:
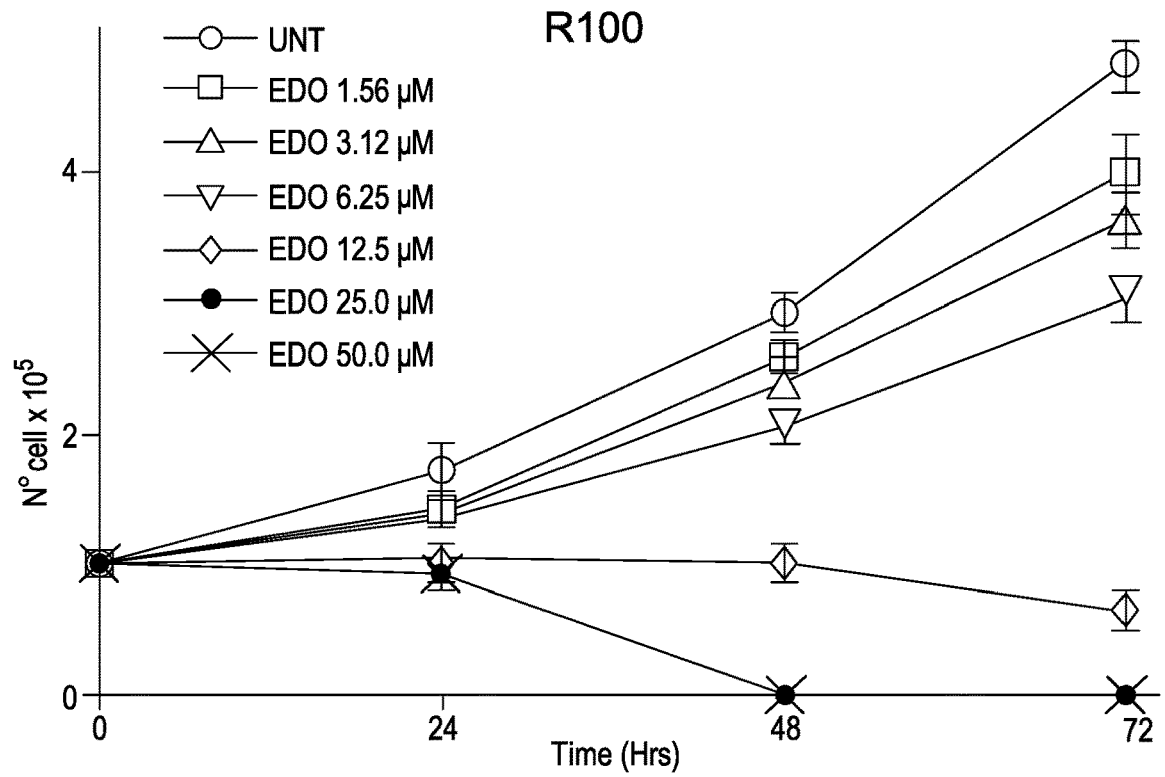
FIG. 6a is a plot of the number of cells for the bendamustine resistant cell line R100 against different concentrations of the compound of formula I measured 24, 48 and 72 hours after treatment with said compound.
Figure 6B:
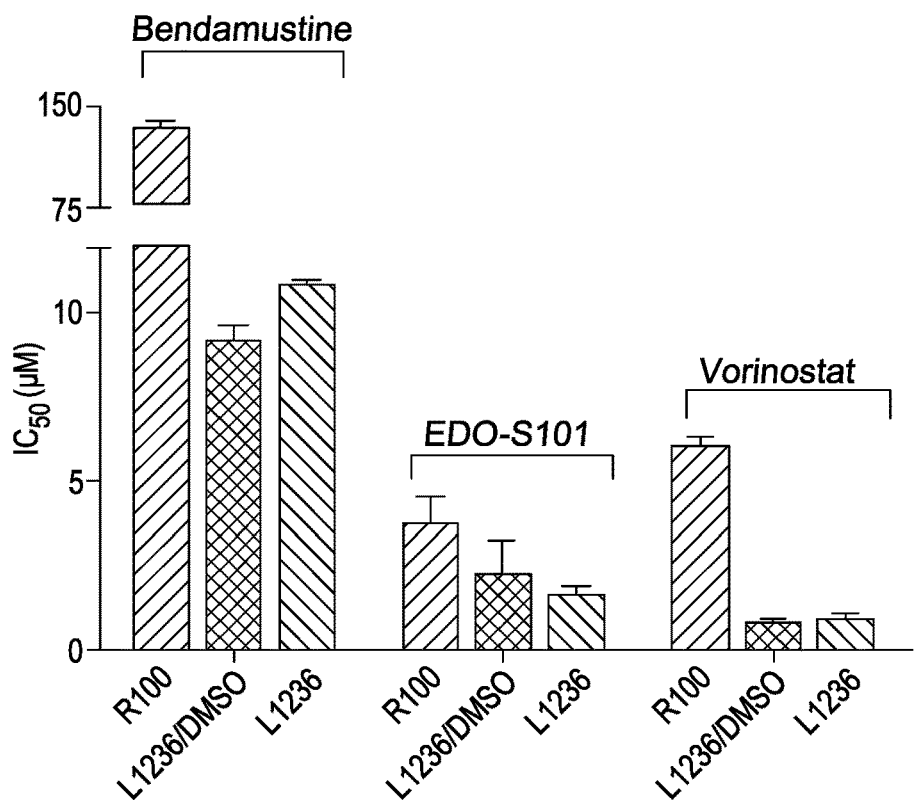
FIG. 6b shows the IC50 values for bendamustine, the compound of formula I and vorinostat against three different Hodgkin lymphoma cell lines.

It can also be seen from FIG. 6a that at the higher concentrations of EDO-S101 the number of viable cells after exposure to the compound tails off rapidly, with no viable cells being observed 48 hours after treatment with 50 µM EDO-S101. It is also noteworthy that the anti-proliferative activity of EDO-S101 against the bendamustine-resistant Hodgkin lymphoma cell line R100 is greater than that of vorinostat. The evidence of this example provides strong proof of the anti-proliferative activity of EDO-S101 against Hodgkin lymphoma cell lines that have to date proven difficult to treat, making it a promising candidate for the treatment of Hodgkin lymphoma.

Example 7 Assessment of Apoptosis Induced by EDO-S101

This assay was performed on 7 cell lines (HDLM2 was excluded due to the low number of available cells) at 24 h and 48 h following EDO-S101 treatment (5 µM, DMSO). Control cells were cultured in the same final concentration of DMSO. Only viable cells (using Hoechst staining) were focused on, and all necrotic cells were excluded. Apoptosis was determined using annexin V-FITC and Hoechst (33342) double staining according to the manufacturer's instructions (BD Biosciences). Cell-cycle fractions were determined by Hoechst nuclear staining. Briefly, cells were harvested, washed in PBS, incubated with annexin V-FITC and Hoechst solution for 30 minutes at room temperature. Data were collected using a FACSCalibur flow cytometer (BD Biosciences) and analyzed with FlowJo Version 7.5.5 obtainable from FlowJo, LLC. Results represent the mean value of 3 independent experiments.

All cells exhibited high sensitivity to EDO-S101 for apoptosis reflecting the major DNA repair deficiency. L540 cell exhibited a higher sensitivity as well as all others cell lines independent of P53 status.

Example 8 Development of a Xenograft Model of Hodgkin Lymphoma

The human HL-derived cell lines L428, KMH2, L591, HDLM2, L540, SUP-HD and L1236 were cultured in Gibco RPMI 1640 medium supplemented with Glutamax and 10% FBS and 1% antibiotics at 37° C. The different cell lines exhibited varying division rates.

Immunodeficient NOD-SCID-gammac−/− (NSG) mice aged 5 to 6 weeks were purchased from Charles River (NOD.Cg-Prkdcscid Il2rgtm1Wjl/SzJ). The mice arrived two weeks before the beginning of the experiments and were housed in micro-isolator cages during the entire course of the study. Immediately prior to the injection of Hodgkin lymphoma cells, mice were exposed to 3Gy gamma irradiation using an IBL637 $^{137}$Cs irradiator at a dose rate of 0.61Gy/min. From $10^3$ to $10^6$ cells, either from the original cell lines or following amplification, were injected intravenously via the retro-orbital sinus. The mice were sacrificed by cervical dislocation and different organs were analysed and tumoural infiltration examined using multiple techniques.

The injected L428-s cell line served as a control for all experiments.

The first step of the in vivo study consisted of the injection of $10^6$ cells of L428-c, KMH2-c, L591 and L1236 per NSG mouse. Of note, while 100% of the mice injected with L428-c displayed tumour infiltration, this was true for only 66% of those injected with KMH2-c. There was a high level of infiltration of L428-c Hodgkin lymphoma cells into various organs of the mice. Significant infiltration was observed in liver, spleen and bone morrow in addition to parotid salivary glands, the eyes and harderrun gland related to the site of injection of the cells. Histological analyses of tumours grown in NSG mice showed the presence of large multinucleate CD30 positive cells as observed for human Hodgkin lymphoma. Of note, granuloma like Hodgkin lymphoma human lymph nodes were not observed because of the nature (immunodeficiency) of the mice used. In addition, because of the high number of cells injected, the survival of the mice did not exceed 6 weeks.

Unfortunately, no FDG up-take was observed in the liver tumour in mice. Some assays were performed using [18F] FDG PET/CT to image and quantify in vivo infiltration of tumour cells.

Despite this limitation in the PET/CT and given the high level of tumour infiltration in NSG mice, L428-c was considered to be the most suitable candidate for the establishment of this animal model for Hodgkin lymphoma and reproducibility and viability studies were performed.

Figure 7:
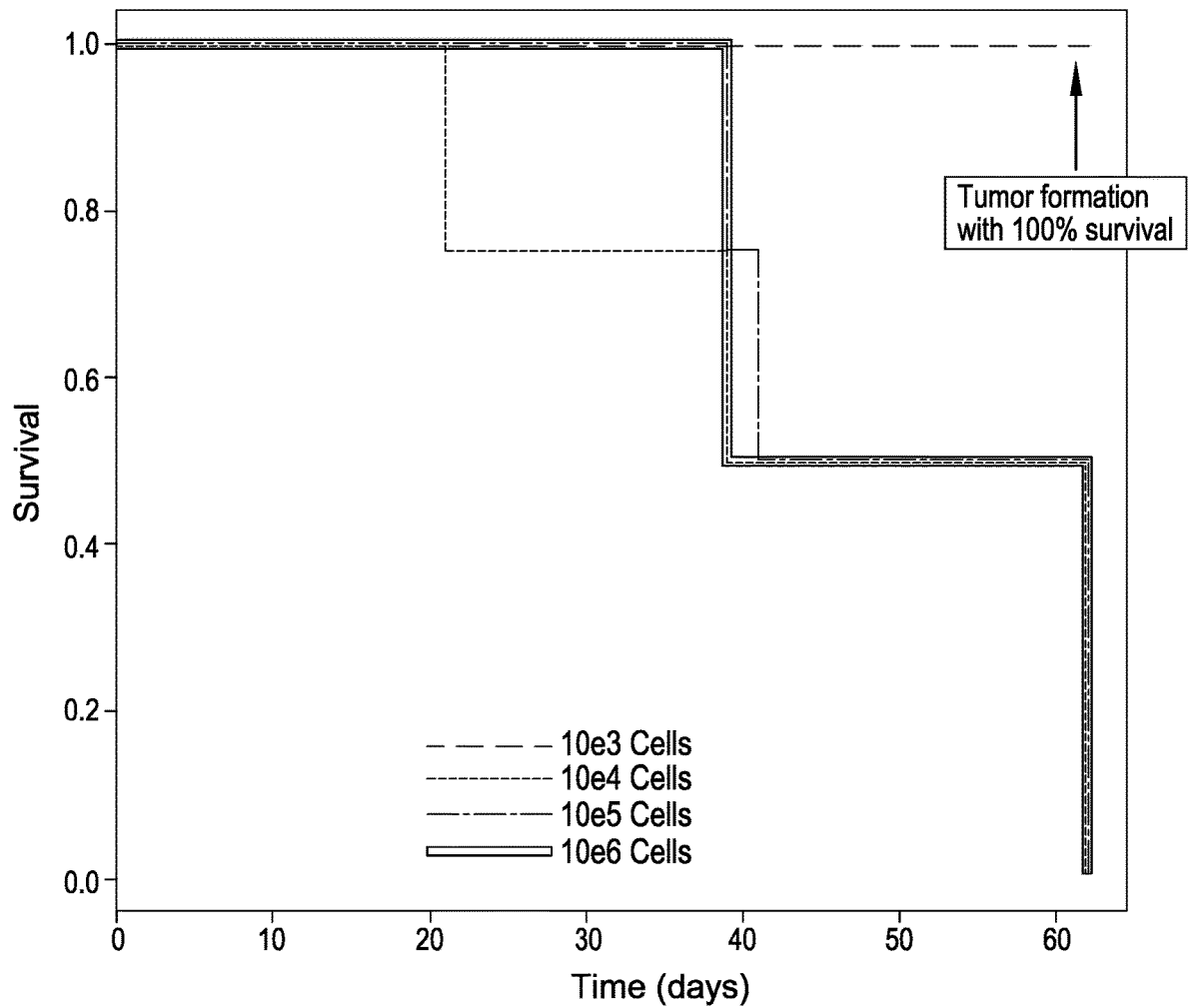
FIG. 7 shows a plot of survival of fraction of surviving mice against time after injection with varying concentrations of Hodgkin lymphoma L428s cells.

FIG. 7 shows the number of days of survival for this model after injection of from $10^3$ up to $10^6$ Hodgkin lymphoma cells, thus demonstrating the reproducibility of the model as well as the effect of reducing the number of injected cells, resulting in low toxicity and better compatibility with the viability of the mice.

Example 9 Antitumour Effects of EDO-S101 on NOD/SCID Gamma-/- Mice with Hodgkin Lymphoma Cell Line Xenografts Experimental Procedure Two independent experiments were performed to investigate the dose-effect of EDO-S101 in NSG mice eight weeks after xenografting with L428 cells as in Example 8. Two different doses were tested, 60 mg/kg and 80 mg/kg, according to the protocol shown in FIG. 8a. The aim of the protocol shown in FIG. 8b was to evaluate the effect of sequential treatment with a moderate dose of 60 mg/kg given at an interval of three weeks.

The mice were sacrificed by cervical dislocation. The sampled organs consisted of the eyes (site of injection), liver, spleen and bone marrow. Following dissection of different organs, including tumours, the first portion was used for flow cytometry (FACS) and cytogenetic analyses while the second was fixed in 4% paraformaldehyde (PFA) for immunohistochemistry (IHC). To obtain a single cell suspension, the tissues were first cut into pieces. Thereafter, the cells were physically disaggregated using an 80 µm nylon cell strainer and filtered a second time through a 70 µm nylon cell strainer (BD Biosciences, Erembodegem, Belgium).

The organs were conducted to histopathological analysis, flow cytometry analyses and immunofluorescence and cytogenetic analyses according to the following procedures.

Immunohistochemistry Analysis

Organs were fixed in 4% PFA, trimmed and post-fixed in 70° ethanol. They were then briefly processed using a vacuum inclusion processor and paraffin blocks were prepared. Five micrometer-thick sections were cut from these blocks and the resulting sections were stained with hemotoxylin-eosine (H&E) for histopathological analysis. In addition, IHC was carried out on of the totality of liver and spleen specimens for confirmation of the spread of engrafted cells. The search for single cells or small groups of grafted Hodgkin lymphoma cells was performed using an anti-CD30 antibody (DAKO, France; 1:40, EDTA pH9 pretreatment) and the Ventana Discovery XT IHC system. Apoptosis and tumour necrosis were analysed.

Microscopic findings were assigned a severity score based upon the following scale: "0"=within physiological limits, "1"=minimal, "2"=mild, "3"=moderate, "4"=marked, "5"=severe. This severity score was attributed according to the size and number of observed lesions.

Flow Cytometry

Cells were gated to exclude apoptotic or necrotic cells and sorted into CD30-/CD15- and CD30+ and CD15+/CD30+ fractions by gating on the lowest and highest 5% PE-expressing cells, respectively. Following sorting, the CD30-/CD15- cell fractions were analyzed using a FACScan flow cytometer (Becton Dickinson) and found to be more than 98% pure. For phenotypic analyses of cell lines or sorted cells, cells were prepared as described, and then stained with mouse anti-human CD30-phycoerthrin (PE), CD15-fluorescein isothyocyanate (FITC), CD14-APC-cyanine 7 (Cy7) and CD45-APC (all antibodies from BD PharMingen, San Diego, Calif.). Staining for aldehyde dehydrogenase (ALDH) activity was performed using the Aldefluor reagent (StemCell Technologies, Vancouver, BC) according to the manufacturer's instructions. Cells were subsequently analysed using a FACS LSRII (Becton Dickinson, Franklin Lakes, N.J.). The injected Hodgkin lymphoma L428-s cell line served as a control for all experiments.

Immunofluorescence for Measuring CD30

Cells were cytospun onto poly-L-lysine-coated glass slides at 700 rpm for 4 min, fixed with 10% formalin for 10 min, and treated with 0.25% Triton X-100 solution for 10 min. After blocking with 5% bovine serum albumin (Sigma), the cells were incubated with an anti-CD30 antibody (DAKO A/S, Glostrup, Denmark). Then, cells were treated with Cyanine 3 anti-mouse IgG (Invitrogen, Carlsbad, Calif.). As a negative control, staining was carried out in the absence of primary antibody. The L428-s cell line served as positive control.

Cytogenetic Analysis

Separated cells were cultured in the presence of RPMI 1640 supplemented with 10% Fetal Calf Serum (FCS) and antibiotics, colcemid (0.1 µg/ml) added 2h before harvesting, and the slides with metaphase chromosomes prepared following the standard methanol/acetic acid (3/1, v/v) procedure.

Four new cell lines were generated after one month of in vitro culture following 24 hour of exposure to EDO-S101. Fluorescence in situ hybridysation (FISH) was performed using a combination of standard procedures from the recommended protocols for chromosomal analysis, following telomere and centromere staining, using peptide nucleic acid (PNA) probes in order to detect unstable chromosomal aberrations and to delimit the chromosome territory. M-FISH was performed using multi-FISH probes (Metasystems GmbH, Altlussheim, Germany), according to the manufacturer's recommendations on the same slide. Images of hybridized metaphases were captured using a charge coupled device camera (Zeiss, Thornwood, N.Y.) coupled to a Zeiss Axioplan microscope and processed using ISIS software (Metasystems).

Results (i) Phenotype of mice treated with EDO-S101

(a) Effect of EDO-S101 Administration on the Weight of the Mice

Figure 9A:
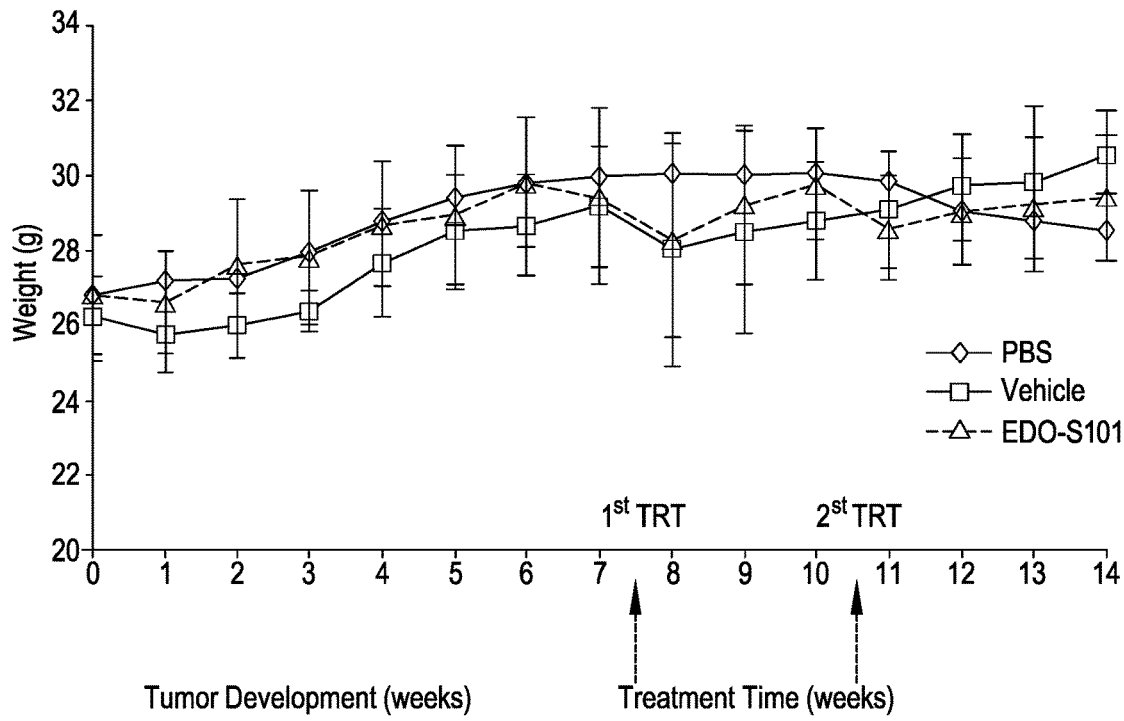
FIG. 9 is a plot of weight of mice against treatment time before and after treatment with the compound of formula I, vehicle and PBS.

The evaluation of the mice treated sequentially with two doses of 60 mg/kg EDO-S101 three weeks apart demonstrated weight loss following each administration which was regained after several weeks (see FIG. 9a). This weight loss was also observed in mice treated with the vehicle. In contrast, the weight of the control mice receiving only freshly prepared phosphate buffered saline (PBS) buffered to 7.3-7.4 increased up to 11 weeks and then started to decrease.

Figure 9B:
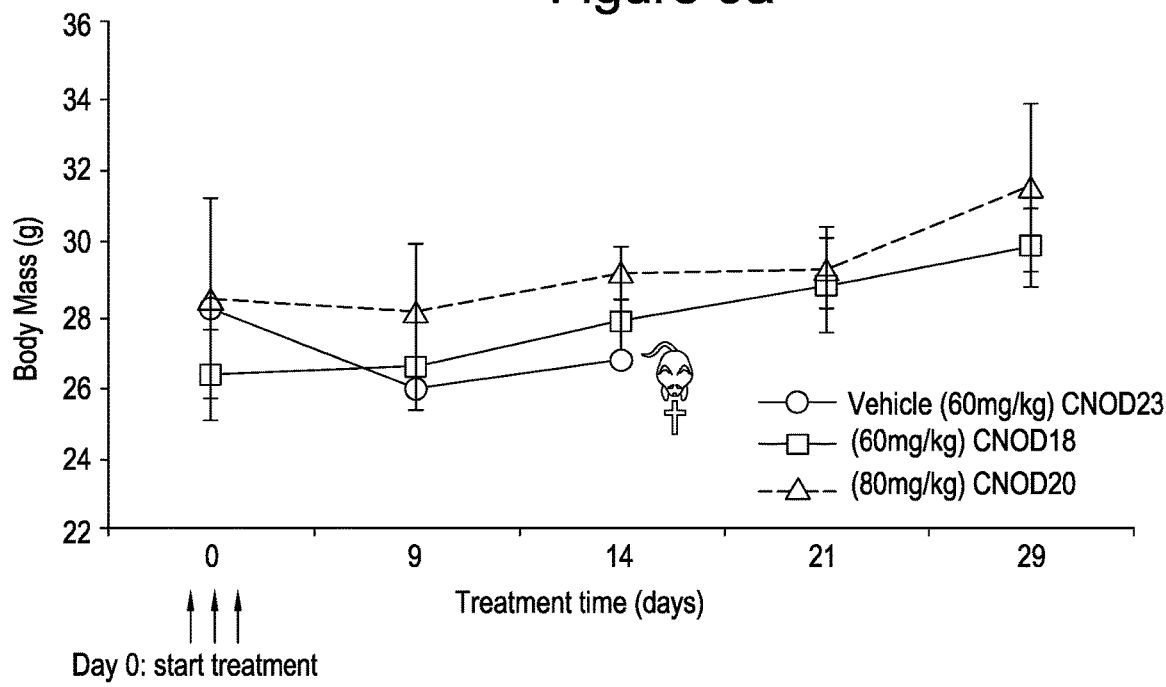

The toxicity of the dose of 80 mg/kg compared to 60 mg/kg was investigated, as compared to the control groups vehicle and PBS. As shown in FIG. 9b, no significant difference was observed between the weight losses following treatment with 60 mg/kg or 80 mg/kg whereas mice treated with vehicle did not survive beyond 14 days.

(b) Regression of the Orbital Tumour Mass Following EDO-S101 Treatment

Some mice developed an orbital tumour mass at the site of the injection. After EDO-S101 injection, signification regression of this tumour was observed. In one mouse only that was treated with two doses of 60 mg/kg of EDO-S101, a regression of the orbital tumour was initially observed followed by re-establishment of the orbital mass 3 weeks later. However, this was the only instance observed of re-establishment of the orbital mass after treatment with EDO-S101 at either concentration.

(ii) Effect of Dose

Figure 10A:
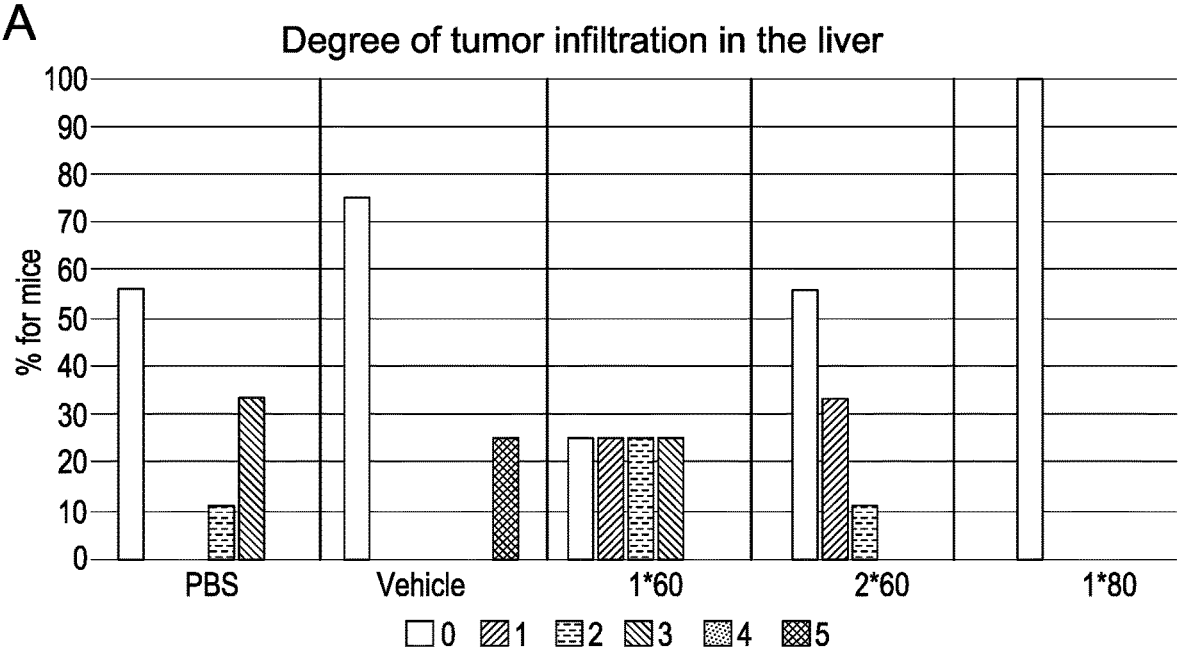
FIG. 10a shows the incidence of lesions of different degrees of severity and the % of mice in which they occurred for each test group of mice treated with one 60 mg/kg dose EDO-S101, two 60 mg/kg doses of the compound of formula I separated by 3 weeks, an 80 mg/kg dose of the compound of formula I, vehicle and PBS as measured using immunohistochemistry.
Figure 10B:
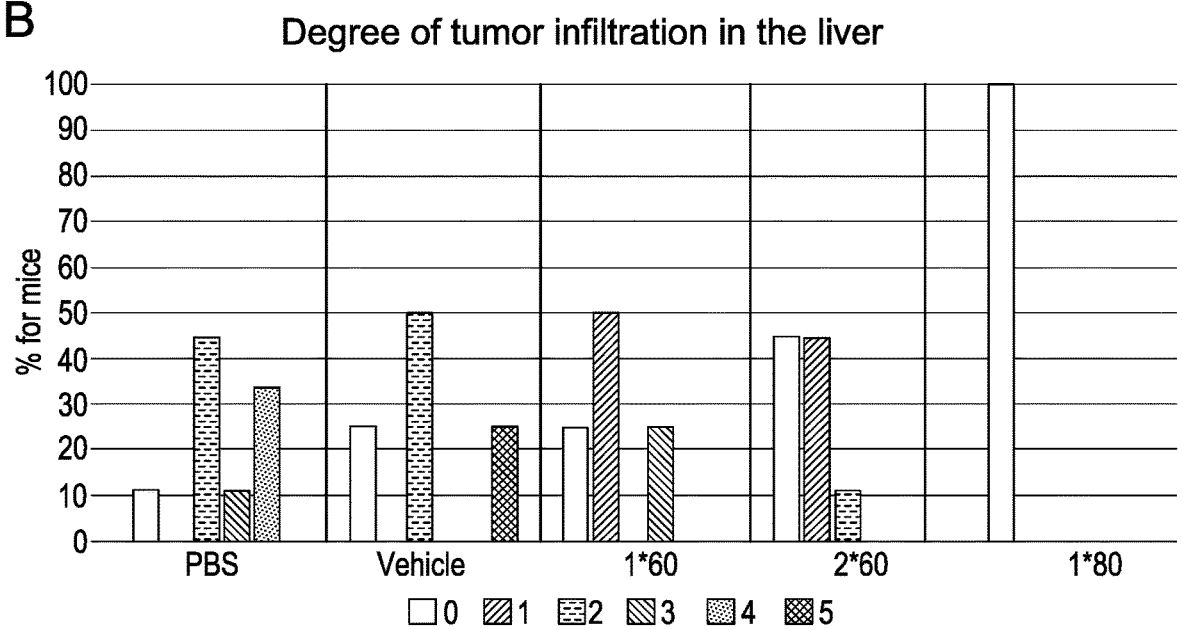
FIG. 10b shows the incidence of lesions of different degrees of severity and the % of mice in which they occurred for each test group of mice treated with one 60 mg/kg dose of the compound of formula I, two 60 mg/kg doses of the compound of formula I separated by 3 weeks, an 80 mg/kg dose of the compound of formula I, vehicle and PBS as measured using immunofluorescence CD30 staining.

Tables 4, 5, 6 and 7 summarise the results obtained for the different treatments and doses as well as the analysed organs and the lesions detections observed following immunohistochemistry and immunofluorescence using CD30. No tumour masses were observed in the liver, nor was infiltration observed into the other organs following treatment with a dose of 80 mg/kg EDO-S101. FIG. 10a shows the absence of tumour cells in the liver following treatment with a single dose of 80 mg/kg by immunohistochemistry after HE staining. FIG. 10b shows the absence of tumour cells in the liver following treatment with a single dose of 80 mg/kg by immunofluorescence using CD30 on cytospin slides. No tumour cells were observed in any organs (liver, spleen, bone marrow).

Even after treatment with a single dose of 60 mg/kg, evidence of significant tumour regression was observed. Only one mouse had moderate tumour lesions, while the other mice had either no tumours or minimal lesions.

Individual microscopic findings following immunohistochemistry: "0"=within physiological limits, "1"=minimal, "2"=mild, "3"=moderate, "4"=marked, "5"=severe.

TABLE 4

| Histology number | Animal number | Group | Liver, Tumor cell infiltration, focal/multifocal | Liver, Tumor cell necrosis/ Apoptosis | Tumor tissue, without connection to other organs | Eye and/or periocular mucosa, periocular tumor cell infiltration, focal/multifocal/diffuse |
|---|---|---|---|---|---|---|
| 14-056 | cnod 10 | PBS | 0 | | | |
| 14-057 | cnod 11 | PBS | 4 | 1 | | |
| 14-058 | cnod 13 | PBS | 3 | 1 | | |
| 14-059 | cnod 14 | PBS | 0 | | | |
| 14-066 | cnod 23 | PBS | 4 | 3 | yes | |
| 14-083 | cnod 31 | PBS | 4 | 2 | yes | |
| 14-085 | cnod 34 | PBS | 0 | | | |
| 14-086 | cnod 36 | PBS | 0 | | yes | |
| 14-106 | cnod 46 | PBS | 0 | | | |
| 14-084 | cnod 32 | Veh | 5 | 5 | | |
| 14-087 | cnod 37 | Veh | 0 | | | |
| 14-102 | cnod 38 | Veh | 0 | | | 1 |
| 14-103 | cnod 39 | Veh | 0 | | | |
| 14-060 | cnod 16 | 1*60 mg/kg | 2 | 0 | | 5 |
| 14-061 | cnod 18 | 1"60 mg/kg | 1 | 0 | | 4 |
| 14-062 | cnod 19 | 1"60 mg/kg | 0 | | | 3 |
| 14-067 | cnod 17 | 1*60 mg/kg | 3 | 0 | | 4 |
| 14-063 | cnod 20 | 1*80 mg/kg | 0 | | | |
| 14-064 | cnod 21 | 1*80 mg/kg | 0 | | | 5 |
| 14-065 | cnod 22 | 1"80 mg/kg | 0 | | | |
| 14-088 | cnod 41 | 2*60 mg/kg | 0 | | | |
| 14-089 | cnod 42 | 2*60 mg/kg | 0 | | | |
| 14-090 | cnod 45 | 2*60 mg/kg | 1 | 0 | yes | |
| 14-091 | cnod 49 | 2*60 mg/kg | 0 | | | 4 |
| 14-104 | cnod 43 | 2*60 mg/kg | 0 | | | |

TABLE 4-continued

| | | | | | |
|---|---|---|---|---|---|
| 14-105 | cnod 44 | 2*60 mg/kg | 1 | 0 | |
| 14-107 | cnod 47 | 2*60 mg/kg | 0 | | |
| 14-108 | cnod 48 | 2*60 mg/kg | 1 | 0 | yes |
| 14-109 | cnod 50 | 2*60 mg/kg | 2 | 0 | |

| Histology number | Tumor/Eye, Tumor cell necrosis/ appotosis | Lung, alveolar histiocytosis | Spleen, red pulp activation, diffuse | Kidney, cortex, tubular degeneration, vacuolar, acute, bilateral focal/ multifocal/diffuse |
|---|---|---|---|---|
| 14-056 | | | | |
| 14-057 | | | | |
| 14-058 | | 2 | 2 | |
| 14-059 | | | | |
| 14-066 | 4 | | 1 | 3 |
| 14-083 | 3 | | | |
| 14-085 | | | | |
| 14-086 | 3 | | 1 | |
| 14-106 | | | | |
| 14-084 | | | 2 | |
| 14-087 | | | | |
| 14-102 | 0 | | 2 | |
| 14-103 | | | | |
| 14-060 | 0 | | | |
| 14-061 | 0 | | | |
| 14-062 | 1 | 1 | | |
| 14-067 | 1 | | | |
| 14-063 | | | | |
| 14-064 | 1 | | | |
| 14-065 | | 1 | | |
| 14-088 | | | | |
| 14-089 | | | | |
| 14-090 | 4 | | | |
| 14-091 | 2 | | | |
| 14-104 | | | | |
| 14-105 | | | 3 | |
| 14-107 | | | | |
| 14-108 | 2 | | | |
| 14-109 | | | | |

Incidence of tumour cell infiltration using HE staining and immunohistochemistry

TABLE 5

| | PBS | | Veh | | 1*60 mg/kg | | 2*60 mg/kg | | 80 mg/kg | |
|---|---|---|---|---|---|---|---|---|---|---|
| | n | % | n | % | n | % | n | % | n | % |
| Total number of mice | 9 | 100.0 | 4 | 100.0 | 4 | 100.0 | 9 | 100.0 | 5 | 100.0 |
| Tumour presence | | | | | | | | | | |
| Overall | 5 | 55.6 | 2 | 50.0 | 4 | 100.0 | 5 | 55.6 | 1 | 33.3 |
| Animals with tumour infiltration in liver and in the injection area | 2 | 22.2 | 0 | 0.0 | 3 | 75.0 | 0 | 0.0 | 0 | 0.0 |
| Liver: Tumour infiltration | | | | | | | | | | |
| Overall | 4 | 44.4 | 1 | 25.0 | 3 | 75.0 | 4 | 44.4 | 0 | 0.0 |
| No | 5 | 55.6 | 3 | 75.0 | 1 | 25.0 | 5 | 55.6 | 3 | 100.0 |
| Minimal | 0 | 0.0 | 0 | 0.0 | 1 | 25.0 | 3 | 33.3 | 0 | 0.0 |
| Mild | 0 | 0.0 | 0 | 0.0 | 1 | 25.0 | 1 | 11.1 | 0 | 0.0 |
| Moderate | 1 | 11.1 | 0 | 0.0 | 1 | 25.0 | 0 | 0.0 | 0 | 0.0 |
| Marked | 3 | 33.3 | 0 | 0.0 | 0 | 0.0 | 0 | 0.0 | 0 | 0.0 |
| Severe | 0 | 0.0 | 1 | 25.0 | 0 | 0.0 | 0 | 0.0 | 0 | 0.0 |
| Liver: Tumour cell necrosis/apoptosis | | | | | | | | | | |
| Overall | 4 | 100.0 | 1 | 100.0 | 0 | 0.0 | 0 | 0.0 | NA | NA |
| No | 0 | 0.0 | 0 | 0.0 | 3 | 100.0 | 4 | 100.0 | NA | NA |
| Minimal | 2 | 50.0 | 0 | 0.0 | 0 | 0.0 | 0 | 0.0 | NA | NA |
| Mild | 1 | 25.0 | 0 | 0.0 | 0 | 0.0 | 0 | 0.0 | NA | NA |
| Moderate | 1 | 25.0 | 0 | 0.0 | 0 | 0.0 | 0 | 0.0 | NA | NA |
| Marked | 0 | 0.0 | 0 | 0.0 | 0 | 0.0 | 0 | 0.0 | NA | NA |
| Severe | 0 | 0.0 | 1 | 100.0 | 0 | 0.0 | 0 | 0.0 | NA | NA |

TABLE 5-continued

|  | PBS | | Veh | | 1*60 mg/kg | | 2*60 mg/kg | | 80 mg/kg | |
| --- | --- | --- | --- | --- | --- | --- | --- | --- | --- | --- |
|  | n | % | n | % | n | % | n | % | n | % |
| Injection site: Tumour infiltration | | | | | | | | | | |
| Overall | 3 | 33.3 | 1 | 25.0 | 4 | 100.0 | 1 | 11.1 | 1 | 33.3 |
| No | 0 | 0.0 | 0 | 0.0 | 0 | 0.0 | 0 | 0.0 | 0 | 0.0 |
| Minimal | 0 | 0.0 | 1 | 25.0 | 0 | 0.0 | 0 | 0.0 | 0 | 0.0 |
| Mild | 0 | 0.0 | 0 | 0.0 | 0 | 0.0 | 0 | 0.0 | 0 | 0.0 |
| Moderate | 0 | 0.0 | 0 | 0.0 | 1 | 25.0 | 0 | 0.0 | 0 | 0.0 |
| Marked | 0 | 0.0 | 0 | 0.0 | 2 | 50.0 | 1 | 11.1 | 0 | 0.0 |
| Severe | 3 | 33.3 | 0 | 0.0 | 1 | 25.0 | 0 | 0.0 | 1 | 33.3 |
| Injection site: Tumour cell necrosis/apoptosis | | | | | | | | | | |
| Overall | 3 | 100.0 | 0 | 0.0 | 4 | 100.0 | 3 | 100.0 | 1 | 100.0 |
| No | 0 | 0.0 | 1 | 100.0 | 2 | 50.0 | 0 | 0.0 | 0 | 0.0 |
| Minimal | 0 | 0.0 | 0 | 0.0 | 2 | 50.0 | 0 | 0.0 | 0 | 0.0 |
| Mild | 0 | 0.0 | 0 | 0.0 | 0 | 0.0 | 2 | 66.7 | 0 | 0.0 |
| Moderate | 2 | 66.7 | 0 | 0.0 | 0 | 0.0 | 0 | 0.0 | 0 | 0.0 |
| Marked | 1 | 33.3 | 0 | 0.0 | 0 | 0.0 | 1 | 33.3 | 0 | 0.0 |
| Severe | 0 | 0.0 | 0 | 0.0 | 0 | 0.0 | 0 | 0.0 | 0 | 0.0 |

Individual microscopic findings following immunofluorescence CD30 staining of cytopsin slides: "0" = without any staining; "1" = minimal, <1% staining; "2" = mild, 1% staining; "3" = moderate, <10% staining; "4" = marked, 10-40% staining; "5" = severe, >40% of cells staining.

TABLE 6

| Histology number | Animal number | Group | Liver, Tumour cell infiltration | Eye and/or periocular mucosa, periocular tumour cell infiltration, focal/multifocal/diffuse | Bone marrow | Spleen, red pulp activation, diffuse |
| --- | --- | --- | --- | --- | --- | --- |
| 14-030 | cnod 10 | PBS | 2 |  | 1 | 1 |
| 14-032 | cnod 11 | PBS | 4 |  | 2 | 1 |
| 14-033 | cnod 13 | PBS | 3 | 3 | 2 | 2 |
| 14-024 | cnod 14 | PBS | 2 |  | 1 | 1 |
| 14-023 | cnod 23 | PBS | 4 | 4 | 2 | 1 |
| 14-001 | cnod 31 | PBS | 4 | 3 | 1 | 0 |
| 14003 | cnod 34 | PBS | 2 |  | 0 | 0 |
| 14-007 | cnod 36 | PBS | 2 | 3 | 1 | 1 |
| 14-013 | cnod 46 | PBS | 0 |  |  |  |
| 14-002 | cnod 32 | Veh | 5 |  | 2 | 2 |
| 14009 | cnod 37 | Veh | 0 |  |  |  |
| 14-016 | cnod 38 | Veh | 2 | 3 |  | 0 |
| 14-010 | cnod 39 | Veh | 2 |  | 1 | 1 |
| 14-016 | cnod 16 | 1*60 mg/kg | 1 | 4 |  | 0 |
| 14-021 | cnod 18 | 1*60 mg/kg | 1 | 4 |  |  |
| 14-019 | cnod 19 | 1*60 mg/kg | 0 | 3 | 1 |  |
| 14-018 | cnod 17 | 1*60 mg/kg | 3 | 4 |  |  |
| 14-020 | cnod 20 | 1*80 mg/kg | 0 |  | 0 | 0 |
| 14-021 | cnod 21 | 1*80 mg/kg | 0 | 2 |  |  |
| 14-022 | cnod 22 | 1*80 mg/kg | 0 |  | 1 |  |
| 14-006 | cnod 41 | 2*60 mg/kg | 0 |  | 0 |  |
| 14-005 | cnod 42 | 2*60 mg/kg | 0 |  |  |  |
| 14-004 | cnod 45 | 2*60 mg/kg | 1 |  | 1 | 0 |
| 14-008 | cnod 49 | 2*60 mg/kg | 1 | 2 | 1 | 1 |
| 14-011 | cnod 43 | 2*60 mg/kg | 0 |  | 0 |  |
| 14-012 | cnod 44 | 2*60 mg/kg | 1 |  | 1 | 1 |
| 14-014 | cnod 47 | 2*60 mg/kg | 0 |  | 1 | 1 |
| 14-015 | cnod 48 | 2*60 mg/kg | 1 |  |  |  |
| 14-017 | cnod 50 | 2*60 mg/kg | 2 |  | 1 | 1 |

Incidence of tumour cell infiltration following CD30 immunofluorescence staining of cytopsin slides.

tumours were observed in any organs (liver, spleen, bone marrow), as can be seen from Tables 4 to 7.

TABLE 7

|  | PBS | | Veh | | 1*60 mg/kg | | 2*60 mg/kg | | 80 mg/kg | |
| --- | --- | --- | --- | --- | --- | --- | --- | --- | --- | --- |
|  | n | % | n | % | n | % | n | % | n | % |
| Total number of mice | 9 | 100.0 | 4 | 100.0 | 4 | 100.0 | 9 | 100.0 | 3 | 100.0 |
| *Tumour presence* | | | | | | | | | | |
| Overall | 8 | 88.9 | 3 | 75.0 | 4 | 100.0 | 6 | 66.7 | 2 | 66.7 |
| *Liver: Tumour infiltration* | | | | | | | | | | |
| Overall | 8 | 88.9 | 3 | 75.0 | 3 | 75.0 | 5 | 55.6 | 0 | 0.0 |
| No | 1 | 11.1 | 1 | 25.0 | 1 | 25.0 | 4 | 44.4 | 3 | 100.0 |
| Minimal | 0 | 0.0 | 0 | 0.0 | 2 | 50.0 | 4 | 44.4 | 0 | 0.0 |
| Mild | 4 | 44.4 | 2 | 50.0 | 0 | 0.0 | 1 | 11.1 | 0 | 0.0 |
| Moderate | 1 | 11.1 | 0 | 0.0 | 1 | 25.0 | 0 | 0.0 | 0 | 0.0 |
| Marked | 3 | 33.3 | 0 | 0.0 | 0 | 0.0 | 0 | 0.0 | 0 | 0.0 |
| Severe | 0 | 0.0 | 1 | 25.0 | 0 | 0.0 | 0 | 0.0 | 0 | 0.0 |
| *Spleen: Tumour infiltration* | | | | | | | | | | |
| Overall | 6 | 66.7 | 2 | 50.0 | 0 | 0.0 | 4 | 44.4 | 0 | 0.0 |
| No | 2 | 22.2 | 1 | 25.0 | 1 | 25.0 | 1 | 11.1 | 1 | 33.3 |
| Minimal | 5 | 55.6 | 1 | 25.0 | 0 | 0.0 | 4 | 44.4 | 0 | 0.0 |
| Mild | 1 | 11.1 | 1 | 25.0 | 0 | 0.0 | 0 | 0.0 | 0 | 0.0 |
| Moderate | 0 | 0.0 | 0 | 0.0 | 0 | 0.0 | 0 | 0.0 | 0 | 0.0 |
| Marked | 0 | 0.0 | 0 | 0.0 | 0 | 0.0 | 0 | 0.0 | 0 | 0.0 |
| Severe | 0 | 0.0 | 0 | 0.0 | 0 | 0.0 | 0 | 0.0 | 0 | 0.0 |
| *Bone Marrow: Tumour infiltration* | | | | | | | | | | |
| Overall | 7 | 77.8 | 2 | 50.0 | 1 | 25.0 | 5 | 55.6 | 1 | 33.3 |
| No | 1 | 11.1 | 0 | 0.0 | 0 | 0.0 | 2 | 22.2 | 1 | 33.3 |
| Minimal | 4 | 44.4 | 1 | 25.0 | 1 | 25.0 | 5 | 55.6 | 1 | 33.3 |
| Mild | 3 | 33.3 | 1 | 25.0 | 0 | 0.0 | 0 | 0.0 | 0 | 0.0 |
| Moderate | 0 | 0.0 | 0 | 0.0 | 0 | 0.0 | 0 | 0.0 | 0 | 0.0 |
| Marked | 0 | 0.0 | 0 | 0.0 | 0 | 0.0 | 0 | 0.0 | 0 | 0.0 |
| Severe | 0 | 0.0 | 0 | 0.0 | 0 | 0.0 | 0 | 0.0 | 0 | 0.0 |
| *Injection site: Tumour infiltration* | | | | | | | | | | |
| Overall | 4 | 44.4 | 1 | 25.0 | 4 | 100.0 | 1 | 11.1 | 1 | 33.3 |
| No | 0 | 0.0 | 0 | 0.0 | 0 | 0.0 | 0 | 0.0 | 0 | 0.0 |
| Minimal | 0 | 0.0 | 0 | 0.0 | 0 | 0.0 | 0 | 0.0 | 0 | 0.0 |
| Mild | 0 | 0.0 | 0 | 0.0 | 0 | 0.0 | 1 | 11.1 | 1 | 33.3 |
| Moderate | 3 | 33.3 | 1 | 25.0 | 1 | 25.0 | 0 | 0.0 | 0 | 0.0 |
| Marked | 1 | 11.1 | 0 | 0.0 | 3 | 75.0 | 0 | 0.0 | 0 | 0.0 |
| Severe | 0 | 0.0 | 0 | 0.0 | 0 | 0.0 | 0 | 0.0 | 0 | 0.0 |

These results clearly show the effect of single doses of EDO-S101 at both 60 mg/kg and 80 mg/kg in comparison with the control (PBS or vehicle). There was a remarkable effect on the tumour cell infiltration. No tumour masses were observed in the liver, nor was infiltration observed into the other organs following treatment at the higher dose of 80 mg/kg EDO-S101. At the lower dose of 60 mg/kg only one mouse had moderate tumour lesions, while the other mice had either no tumours or minimal lesions.

Evaluation of tumour cell degeneration (necrosis/apoptosis) based on morphology of the cells was also performed as part of the histopathological evaluation. No cell necerosis was observed following treatment with either 80 mg/kg or 60 mg/kg of EDO-S101. As can be seen from Tables 4 and 5, the PBS control group presented larger tumours compared to the 60 mg/kg EDO-S101 group and they showed a higher degree of necrosis/apoptosis.

A study of the effect of sequential treatment with two doses of 60 mg/kg EDO-S101 three weeks apart was also performed. Signficant tumour regression was observed following two administrations of 60 mg/kg EDO-S101 compared with the control group and with the single dose of 60 mg/kg EDO-S101 (see FIGS. 10a and 10b). Only one mouse exhibited a moderate level of infiltration in the liver. No tumours were observed in any organs (liver, spleen, bone marrow), as can be seen from Tables 4 to 7.

(iii) Cytogenic Investigations

The ocular tumour masses were harvested, as well as cells which infiltrated the liver. Five new cell lines were established from ocular tumours and the livers of both control mice (PBS or vehicle). Cytogenic characterisation using the M-FISH technique was performed and the karyotype was established in L428, L428-s and in new cell lines established from liver tumours of the mice. The presence of small (<46 chromosomes) metaphases was found only in L428-s and cell lines established from liver tumours of the mice. Typical chromosomal abnormalities were found in the cell lines.

For treated mice, it was not possible to obtain either metaphases from direct culture or establish cell lines following the culture of mouse cells treated with different doses of EDO-S101, including a single dose of 60 mg/kg. The few cells present on cytogenic slides showed centromere staining that was abnormal, which could be an indicator of their poor viability.

(iv) Presence of Macrophages

Novel biomarkers CD68 and CD14 which are expressed by tumour associated macrophages and myeloid derived suppressor cells respectively in the microenvironment have recently been reported to affect the prognosis of Hodgkin lymphoma (Haematologica, 2011 February; 96 (2): 186-189). The presence of the CD14-positive cells following administration of a single dose of EDO-S101 (60 mg/kg or 80 mg/kg) and after two administrations of EDO-S101 at 60 mg/kg was evaluated using flow cytometry with anti CD14 antibodies.

Figure 11:
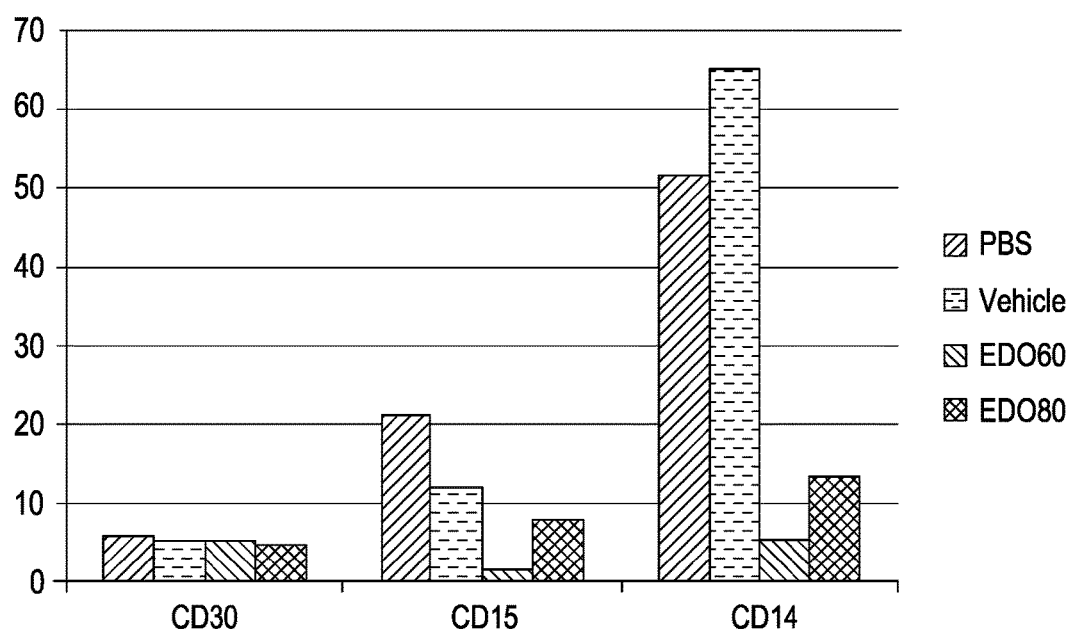
FIG. 11 shows a plot of the frequency of CD14 cells in mice after treatment with PBS, vehicle, one dose of 60 mg/kg of the compound of formula I and one dose of 80 mg/kg of the compound of formula I (plot A) and a plot of the frequency of CD14 cells in mice after treatment with PBS, vehicle and two doses of 60 mg/kg of the compound of formula I.
Figure 11:
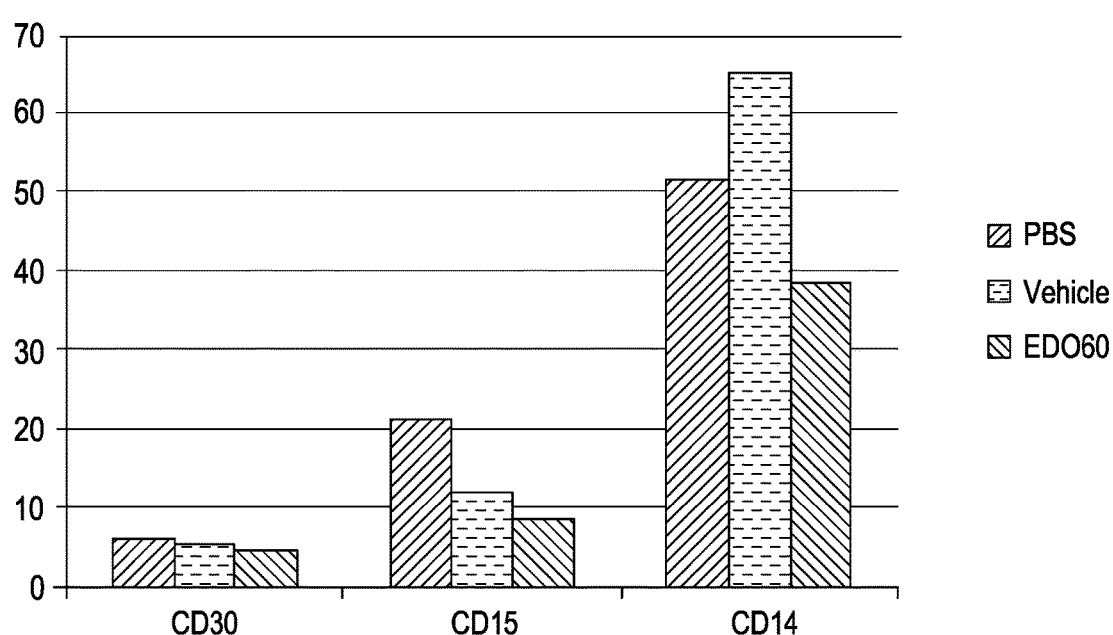

FIG. 11 shows the significantly higher frequency of CD14 cells in untreated mice compared to treated mice, especially at the higher dose of 80 mg/kg EDO-S101. Graph A of FIG. 11 shows the frequency of CD14 cells after treatment with a single dose of EDO-S101 at 60 mg/kg while graph B shows the frequency of CD14 cells after two administrations of EDO-S101 of EDO-S101 at 60 mg/kg. These CD14 cells cells were found at a higher frequency following treatment with 2×60 mg/kg than treatment with a single dose of 80 mg/kg.

The in vitro results demonstrate clearly the sensitivity of all Hodgkin lymphoma cell lines used to treatment with the compound of formula I according to the present invention. This sensitivity implicates different mechanisms including chromosomal aberrations, micronucleus and protein expression.

These in vitro experiments demonstrate that monotherapy with the compound of formula I or a pharmaceutically acceptable salt thereof of the present invention displays a striking time and dose-dependent cytotoxic activity towards all Hodgkin lymphoma cell lines. The IC50s of the compound of formula I or a pharmaceutically acceptable salt thereof of the present invention are about ten-fold lower than those of bendamustine towards tumour cells of Hodgkin lymphoma. In bendamustine-naive Hodgkin lymphoma cells (L1236) the compound of formula I or a pharmaceutically acceptable salt thereof of the present invention has been demonstrated to activate cell cycle check point proteins and induce cellular and gene expression changes compatible with triggering of apoptosis. In bendamustine-resistant Hodgkin lymphoma cells (L1236 R100) the compound of formula I or a pharmaceutically acceptable salt thereof of the present invention has been demonstrated to downregulate activated cell cycle checkpoints and mitotic catastrophe genes and upregulate proapoptotic genes. It also corrects the constitutive ATM/ATR unbalance by upregulating ATR and lowering ATM transcripts in bendamustine-resistant Hodgkin lymphoma cells L1236 R100.

These results are backed up by the in vivo results in the NOD/SCID mice xenografted with the Hodgkin lymphoma cell line 428-s. Using either a single injection of the compound of formula I (60 mg/kg or 80 mg/kg) or two injections three weeks apart (each at 60 mg/kg) a significant decrease in the severity of tumoural cell infiltration after treatment was observed, especially at the single dose of 80 mg/kg (although all dosage regimes were effective). All mice were observed to determine the inter-mouse variation with respect to the organ and the level of infiltration, but in all treated mice a high level of infiltration was not observed demonstrating the efficacy of the compound of formula I or a pharmaceutically acceptable salt thereof.

The absence of necrotic cells in treated mice and the absence of cell degeneration compared to the situation observed in untreated mice could be correlated with the anti-tumoural effect of the compound of formula I or a pharmaceutically acceptable salt thereof. The necrotic cells observed in untreated mice could be related to spontaneous apoptosis. No significant difference was observed for the weight of the mice or the different organs. Additionally, the weight of the liver in the different mice shows a high degree of heterogeneity in the control mice (PBS or vehicle) but the liver remained homogeneous in the mice treated with the compound of formula I or a pharmaceutically acceptable salt thereof.

In conclusion, the compound of formula I or a pharmaceutically acceptable salt thereof according to the present invention is a very active molecule in these in vitro and in vivo pre-clinical models of Hodgkin lymphoma. This includes tumour cells that have previously been very difficult to treat including bendamustine-resistant Hodgkin lymphomas such as the L1236 R100 cell line. The compound of formula I or a pharmaceutically acceptable salt thereof of the present invention has unique and particularly effective combined function in a single molecule of a bifunctional alkylator and a pan-HDAC inhibitor. Following a strong DNA-damage response, triggering of apoptosis and/or mitotic catastrophe may take place in Hodgkin lymphoma cells according to their sensitivity to bendamustine. The compound of formula I or a pharmaceutically acceptable salt thereof represents an agent of great potential advantage in the treatment of Hodgkin lymphoma based on the presented data.

Figure 12A:
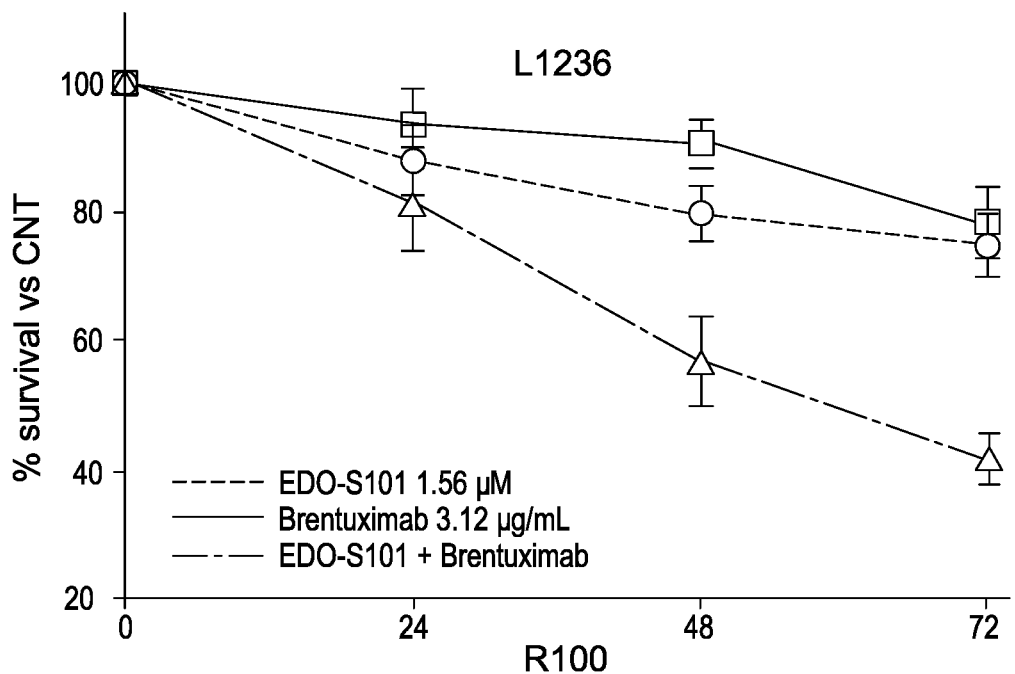
FIG. 12a shows a plot of % survival of L1236 bendamustine-naive cells against time for EDO-S101 alone, Brentuximab Vedotin alone, and the two in combination.
Figure 12B:
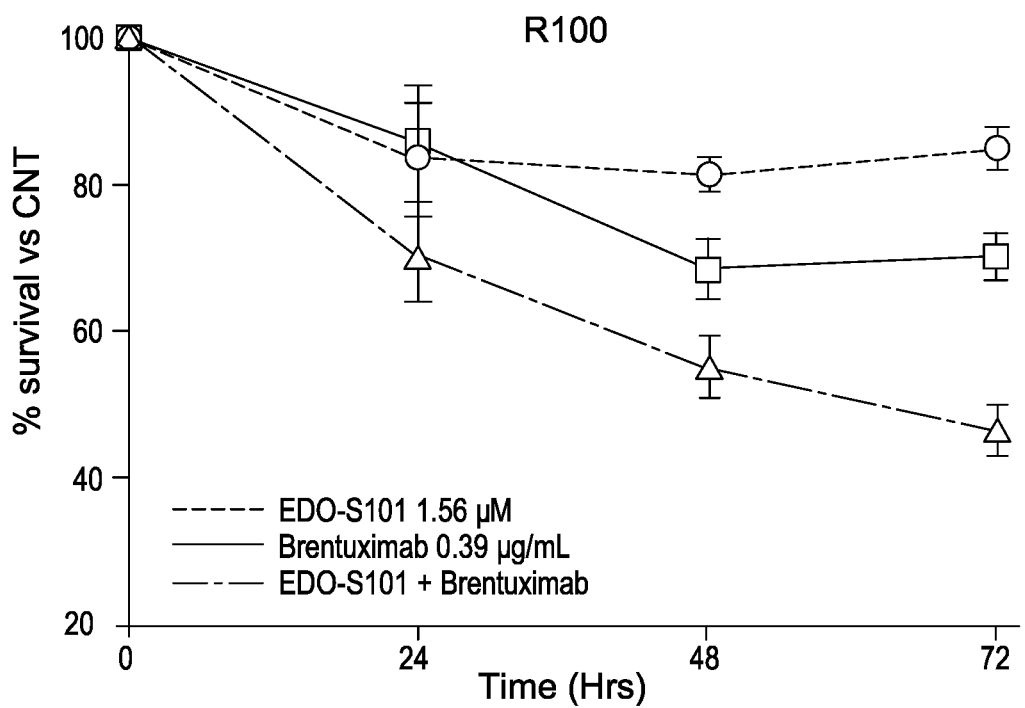
FIG. 12b shows a plot of % survival of R100 bendamustine-resistant cells against time for EDO-S101 alone, Brentuximab Vedotin alone, and the two in combination.

Example 10 Combination Therapy with Brentuximab Vedotin 1.56 μM of EDO-S101 was administered to two Hodgkin lymphoma cell lines, the bendamustine naïve cell line L1236 and the bendamustine resistant cell line R100. In a second experiment, Brentuximab Vedotin was administered at a concentration of 3.12 μg/ml to the L1236 cell line and at a concentration of 0.39 μg/ml to the R100 cell line. Finally, in a third experiment EDO-S101 and Brentuximab Vedotin were administered in combination to each of the two cell lines at the same concentrations that they were administered in the monotherapy experiments. The results showing % survival of the lymphoma cell lines against a control versus times are as shown in FIGS. 12a and 12b.

In the naïve L1236 cell line, EDO-S101 alone activated cell cycle checkpoint proteins and induced cellular and gene expression changes compatible with the triggering of apoptosis. In the bendamustine resistant R100 cell line, EDO-S101 alone was found to correct the constitutive ATM/ATR unbalance by upregulating ATR and downregulating ATM transcripts.

Most importantly, it was found that EDO-S101 at sub-IC50 levels is synergistic with Brentuximab Vedotin in inducing cell death of L1236 cells and furthermore that at sub-IC concentrations EDO-S101 allows low doses of Brentuximab Vedotin (typically 10-fold lower than IC50) to exert a considerable cyctotoxic effect on bendamustine resistant R100 cells.

The invention claimed is:

1. A method of treating Hodgkin lymphoma in a patient in need thereof comprising administering to said patient an effective amount of said compound of formula I or a pharmacologically acceptable salt thereof:

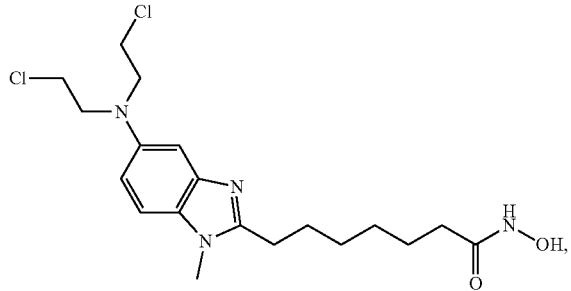

I wherein the Hodgkin lymphoma is relapsed/refractory Hodgkin lymphoma.

2. The method according to claim 1, wherein the pharmacologically acceptable salt of the compound of formula I is the hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, oxalate, succinate, fumarate, tartrate, tosylate, mandelate, salicylate, lactate, p-toluenesulfonate, naphthalenesulfonate or acetate salt.

3. The method according to claim 1, wherein the Hodgkin lymphoma is classical Hodgkin lymphoma.

4. The method according to claim 1, wherein the Hodgkin lymphoma is lymphocyte predominant Hodgkin lymphoma, nodular sclerosis classical Hodgkin lymphoma, mixed cellularity classical Hodgkin lymphoma, lymphocyte-depletion classical Hodgkin lymphoma, lymphocyte-rich classical Hodgkin lymphoma, or nodular lymphocyte predominant Hodgkin lymphoma.

5. The method according to claim 1, wherein the Hodgkin lymphoma is bendamustine-resistant.

6. The method according to claim 1, wherein the compound of formula I or a pharmacologically acceptable salt thereof is administered intravenously to the patient in need thereof at a dosage level of from 20 mg/m$^2$ to 150 mg/m$^2$ body surface area of the patient; or from 40 mg/m$^2$ to 100 mg/m$^2$ body surface area of the patient; or 80 mg/m$^2$ body surface area of the patient; or 60 mg/m$^2$ body surface area of the patient; or 100 mg/m$^2$ body surface area of the patient.

7. The method according to claim 1, wherein the compound of formula I or a pharmacologically acceptable salt thereof is administered intravenously to the patient in need thereof on day 1 of a 21 day treatment cycle.

8. The method according to claim 1, wherein the compound of formula I or a pharmacologically acceptable salt thereof is administered intravenously to the patient in need thereof on days 1 and 22 of the treatment cycle, for 3 to 12 cycles of treatment.

9. The method according to claim 1, wherein the compound of formula I or a pharmacologically acceptable salt thereof is administered intravenously to the patient in need thereof at a dosage level of from 40 mg/m$^2$ to 100 mg/m$^2$ body surface area of the patient on day 1 of a 21 day treatment cycle.

10. The method according to claim 1, wherein the compound of formula I or a pharmacologically acceptable salt thereof is administered intravenously to the patient in need thereof at a dosage level of from 40 mg/m$^2$ to 100 mg/m$^2$ body surface area of the patient on days 1 and 22 of a treatment cycle, for 6 to 12 consecutive cycles.

11. The method according to claim 1, wherein the Hodgkin lymphoma is p53$^-$ (p53-negative).

12. The method according to claim 1, wherein the Hodgkin lymphoma is p53$^+$ (p53-positive).

13. The method according to claim 1, further comprising administering to the patient Brentuximab Vedotin.

14. The method according to claim 11, wherein the Hodgkin lymphoma is bendamustine-resistant.

15. The method according to claim 12, wherein the Hodgkin lymphoma is bendamustine-resistant.

16. The method according to claim 13, wherein the Hodgkin lymphoma is bendamustine-resistant.

17. The method according to claim 14, further comprising administering to the patient Brentuximab Vedotin.

18. The method according to claim 15, further comprising administering to the patient Brentuximab Vedotin.

* * * * *